United States Patent
Schnell et al.

(10) Patent No.: US 9,238,042 B2
(45) Date of Patent: Jan. 19, 2016

(54) ANTISENSE MODULATION OF INTERLEUKINS 17 AND 23 SIGNALING

(75) Inventors: Frederick J. Schnell, Corvallis, OR (US); Patrick L. Iversen, Corvallis, OR (US); Dan V. Mourich, Albany, OR (US); Gunnar J. Hanson, Bothell, WA (US)

(73) Assignee: Sarepta Therapeutics, Inc., Corvallis, OR (US)

( * ) Notice: Subject to any disclaimer, the term of this patent is extended or adjusted under 35 U.S.C. 154(b) by 92 days.

(21) Appl. No.: 13/107,528

(22) Filed: May 13, 2011

(65) Prior Publication Data

US 2011/0289608 A1    Nov. 24, 2011

Related U.S. Application Data

(60) Provisional application No. 61/334,516, filed on May 13, 2010.

(51) Int. Cl.
| | |
|---|---|
| *A61K 49/00* | (2006.01) |
| *C12Q 1/70* | (2006.01) |
| *A61K 31/713* | (2006.01) |
| *C12N 15/113* | (2010.01) |
| *A01K 67/027* | (2006.01) |
| *G01N 33/50* | (2006.01) |
| *G01N 33/569* | (2006.01) |
| *G01N 33/68* | (2006.01) |

(52) U.S. Cl.
CPC ............. *A61K 31/713* (2013.01); *A01K 67/027* (2013.01); *C12N 15/1136* (2013.01); *C12N 15/1138* (2013.01); *G01N 33/5041* (2013.01); *G01N 33/56983* (2013.01); *G01N 33/6893* (2013.01); *A01K 2267/03* (2013.01); *C12N 2310/11* (2013.01); *C12N 2310/3233* (2013.01); *C12N 2310/3513* (2013.01); *C12N 2320/33* (2013.01); *G01N 2333/005* (2013.01); *G01N 2333/54* (2013.01); *G01N 2500/00* (2013.01)

(58) Field of Classification Search
USPC ............. 435/6, 91.1, 91.31, 455, 5, 6.1, 375; 514/1, 2, 44; 536/23.1, 24.5; 424/9.1, 424/9.2

See application file for complete search history.

(56) References Cited

U.S. PATENT DOCUMENTS

| | | | |
|---|---|---|---|
| 2006/0127981 A1* | 6/2006 | Bergman et al. ............. | 435/69.1 |
| 2008/0267978 A1* | 10/2008 | Zutter ........................ | 424/174.1 |
| 2010/0021456 A1 | 1/2010 | Miossec et al. | |
| 2011/0118334 A1* | 5/2011 | Iversen ........................ | 514/44 A |
| 2012/0141463 A1* | 6/2012 | Wu et al. ..................... | 424/131.1 |
| 2013/0005792 A1* | 1/2013 | Haining et al. .............. | 514/44 A |
| 2013/0045202 A1* | 2/2013 | Irving et al. ................. | 424/133.1 |
| 2013/0089517 A1* | 4/2013 | Brady et al. .................. | 424/85.2 |

FOREIGN PATENT DOCUMENTS

| | | |
|---|---|---|
| EP | 1 938 802 A1 | 7/2008 |
| WO | WO 02/38764 A2 | 5/2002 |
| WO | WO 2005/010044 A2 | 2/2005 |
| WO | WO 2006/047683 A2 | 5/2006 |
| WO | WO 2006/088833 A2 | 8/2006 |
| WO | WO 2008/036127 A2 | 3/2008 |
| WO | WO 2009/026412 A1 | 2/2009 |

OTHER PUBLICATIONS

Carlson et al., Blood, vol. 113, No. 6, pp. 1365-1374 (2009).*
Rangachari et al., J. Experimental Med., vol. 203, No. 8, pp. 2009-2019 (2006).*
Abes et al., "Arginine-rich cell penetrating peptides: Design, structure-activity, and applications to alter pre-mRNA splicing by steric-block oligonucleotides," *J Pept Sci 14*: 455-460, 2008.
Abes et al., "Delivery of steric block morpholino oligomers by (R-X-R)$_4$ peptides: structure-activity studies," *Nucleic Acids Research 36*(20): 6343-6354, Sep. 16, 2008.
Abes et al., "Vectorization of morpholino oligomers by the (R-Ahx-R)$_4$ peptide allows efficient splicing correction in the absence of endosomolytic agents," *Journal of Controlled Release 116*: 304-313, 2006.
Egholm et al., "PNA hybridizes to complementary oligonucleotides obeying the Watson-Crick hydrogen-bonding rules," *Nature 365*: 566-568, Oct. 7, 1993.
Jearawiriyapaisarn et al., "Sustained Dystrophin Expression Induced by Peptide-conjugated Morpholino Oligomers in the Muscles of *mdx* Mice," *Mol Ther 16*(9): 1624-1629, Sep. 2008.
Lebleu et al., "Cell penetrating peptide conjugates of steric block oligonucleotides," *Advanced Drug Delivery Reviews 60*: 517-529, 2008.
Marshall et al., "Arginine-rich cell-penetrating peptides facilitate delivery of antisense oligomers into murine leukocytes and alter pre-mRNA splicing," *Journal of Immunological Methods 325*: 114-126, 2007.
Moskophidis et al., "Resistance of Lymphocytic Choriomeningitis Virus to Alpha/Beta Interferon and to Gamma Interferon," *Journal of Virology 68*(3): 1951-1955, Mar. 1994.
Moskophidis et al., "Role of virus and host variables in virus persistence or immunopathological disease caused by a non-cytolytic virus," *Journal of General Virology 76*: 381-391, 1995.
Moulton et al., "Cellular Uptake of Antisense Morpholino Oligomers Conjugated to Arginine-Rich Peptides," *Bioconjugate Chem 15*: 290-299, 2004.
Park et al., "Peroxisome Proliferator-Activated Receptor γ Agonist Down-Regulates IL-17 Expression in a Murine Model of Allergic Airway Inflammation," *The Journal of Immunology 183*: 3259-3267, 2009.

(Continued)

*Primary Examiner* — Jane Zara
(74) *Attorney, Agent, or Firm* — Seed IP Law Group PLLC

(57) ABSTRACT

Provided are antisense oligonucleotides and other agents that target and modulate IL-17 and/or IL-23 signaling activity in a cell, compositions that comprise the same, and methods of use thereof. Also provided are animal models for identifying agents that modulate 17 and/or IL-23 signaling activity.

24 Claims, 12 Drawing Sheets

(56) References Cited

OTHER PUBLICATIONS

Spence et al., "Generation of cellular immunity to lymphocytic choriomeningitis virus is independent of CD1d1 expression," *Immunology 104*: 168-174, 2001.

Summerton et al., "Morpholino Antisense Oligomers: Design, Preparation, and Properties," *Antisense & Nucleic Acid Drug Development 7*: 187-195, 1997.

Wright et al., "The Human IL-17F/IL-17A Heterodimeric Cytokine Signals through the IL-17RA/IL-17RC Receptor Complex," *The Journal of Immunology 181*: 2799-2805, 2008.

Wu et al., "Effective rescue of dystrophin improves cardiac function in dystrophin-deficient mice by a modified morpholino oligomer," *PNAS 105*(39): 14814-14819, Sep. 30, 2008.

Yauch and Shresta, "Mouse models of dengue virus infection and disease," *Antiviral Research 80*: 87-93, 2008.

Zhou et al., "IL-17A versus IL-17F induced intracellular signal transduction pathways and modulation by IL-17RA and IL-17RC RNA interference in AGS gastric adenocarcinoma cells," *Cytokine 38*: 157-164, 2007.

* cited by examiner

IL17RC-SD12 is SEQ: 12 Conjugated to SEQ ID NO: 18

FVB and C57BL/6 mice were infected with LCMV Cl 13

FVB and C57BL/6 mice were infected with LCMV Cl 13, Naive are uninfected FVB

ANTISENSE MODULATION OF INTERLEUKINS 17 AND 23 SIGNALING

CROSS-REFERENCE TO RELATED APPLICATIONS

This application claims the benefit under 35 U.S.C. §119 (e) of U.S. Application No. 61/334,516 filed on May 13, 2010, which is incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 120178_486a_SEQUENCE_LISTING_txt. The text file is about 10 KB, was created on Aug. 3, 2011, and is being submitted electronically via EFS-Web.

BACKGROUND OF THE INVENTION

1. Technical Field

The present invention relates generally to compositions and methods for inhibiting IL-17 and IL-23 signaling pathways and for treating or preventing diseases mediated by interleukin-17 and interleukin-23, such as immune-related and inflammatory diseases.

2. Background

Immune-related and inflammatory diseases often involve multistep pathways and multiple biological systems. Intervention at critical points in one or more of these pathways can have an ameliorative or therapeutic effect. Therapeutic intervention can occur by either antagonizing a detrimental process or pathway, or by stimulating a beneficial process or pathway. The T helper (Th) cell paradigm is widely accepted to explain how the different adaptive immune responses (cellular and humoral) are generated to appropriately respond to diverse types of microbial pathogens. The processes that lead to the differentiation of naive T cells to either IFN-gamma producing Th1 or IL-4 producing Th2 cells were elucidated through the study of the T helper system (Mossman & Coffman) Recently however, several newly discovered members of the Th differentiation pathway have been described. Among these are the TGF-b or IL-10 producing T regulatory cells (Treg or Tr-1, respectively) and IL-17 producing Th17 cells (reviewed in Korn and Gaffen). All of these Th cell types play significant and distinct roles in controlling different infectious agents, tolerance, response resolution and maintenance of immune homeostasis. Differentiation of naive T cells into one specific Th cell type and engagement of effector activity is a highly regulated process where the outcome is determined by a combination of pathogen-derived stimuli and host-derived environmental factors including autocrine and paracrine cytokine profiles that produce positive and negative feedback signals so as to have one type of response predominate (Zhou). The expanded understanding of different Th types has introduced a new paradigm that suggests it is the appropriateness and not the overall magnitude of an immune response that determines the pathogenesis of an organism or its subsequent clearance.

Protracted inflammation brought about by T cell dysregulation is common to various autoimmune diseases. Initially, it was thought that Th1 cells, which mediate responses to intracellular pathogens (e.g. viruses), were responsible for the pathogenesis of various chronic inflammatory diseases, including psoriasis, inflammatory bowel disease, arthritis, autoimmune myocarditis or multiple sclerosis via macrophage activation, excessive cytokine production and induction of self-reactive cytotoxic T lymphocytes (CTL). However, with the recent discovery of IL-23, the role of Th1 cells in autoimmune pathogenesis was brought into question. Th17 cells were first discovered when IL-23-deficient mice (lacking expression of the p19 portion of the heterodimeric cytokine) were shown to be resistant to various models of organ-specific autoimmune disease and exhibited a dramatic diminution in IL-17 expression in a distinct subpopulation of CD4+ T cells. Thus, it was established that Th17 cells and IL-23 fell within an axis of immunity capable of causing tissue destructive responses including recent observations of severe cutaneous, pulmonary and myocardial manifestations in animal models (Rangachari, Mauermann et al. 2006; Carlson, West et al. 2009).

Many immune-related diseases are known and have been extensively studied. There remains a need for therapies where none exists and more effective therapies than those currently available. Such diseases include immune-mediated inflammatory diseases such as asthma, allergic asthma, chronic inflammatory disease (including inflammatory bowel disease, ulcerative colitis, Crohn's disease, arthritis, atopic dermatitis or psoriasis); acute inflammatory disease (e.g. endotoxemia, septicemia, toxic shock syndrome or infectious disease), rheumatoid arthritis, hepatobiliary disease, atherosclerosis, promotion of tumor growth, degenerative joint disease, immune mediated renal disease, adult respiratory disease (ARD), septic shock, multiple organ failure, inflammatory lung injury, chronic obstructive pulmonary disease (COPD), airway hyper-responsiveness, chronic bronchitis, allergic asthma, bacterial pneumonia, psoriasis, eczema, systemic lupus erythematosus (SLE), multiple sclerosis, systemic sclerosis, nephrotic syndrome, organ allograft rejection, graft vs. host disease (GVHD), kidney, lung, heart, etc. transplant rejection, streptococcal cell wall (SCW)-induced arthritis, osteoarthritis, gingivitis/periodontitis, herpetic stromal keratitis, cancers including prostate, renal, colon, ovarian, cervical, leukemia, angiogenesis, restenosis and Kawasaki disease.

There also remains a need for animal models that allow development of therapies for many immune-related diseases. Many infectious disease agents manifest disease not directly from the pathogen but from the host response to the pathogen. In many infectious diseases the "cytokine storm" associated with clearing the infectious agent is responsible for disease manifestation. One such category of infectious agents are those that cause hemorrhagic fever including members of the Arenaviridae, Flaviviridae, Filoviridae, Togaviridae, Arteriviridae, and Bunyaviridae viral families. Animal models that replicate human disease are often not available or perform poorly. For instance, viral replication in an animal model without the associated immunological sequelae seen in infected humans is a poor model for human disease caused by the virus. Animal models that allow perturbation of the IL-23/17 signaling pathways in the context of an infectious disease are particularly needed. Further, animal models that more accurately mimic the human condition will allow development of immunomodulatory therapies that target immune-related diseases, including those beyond the context of infectious diseases.

BRIEF DESCRIPTIONS OF THE DRAWINGS

FIGS. 1D-G show the repeating subunit segment of exemplary morpholino oligonucleotides, designated D through G.

Figure 2:
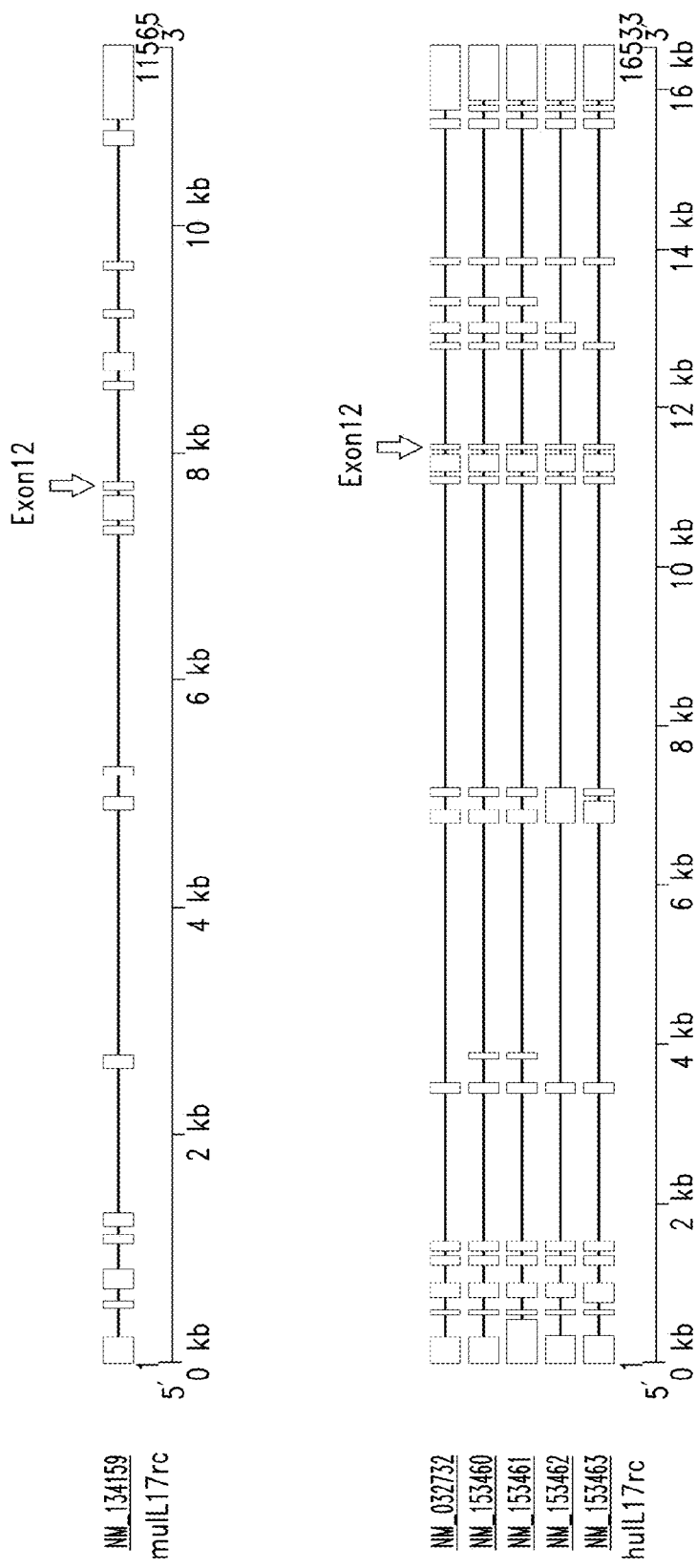

FIG. 2 shows the exon structure of the murine and human IL-17RC genes with the location of exon 12 in both genes noted.

Figure 3:
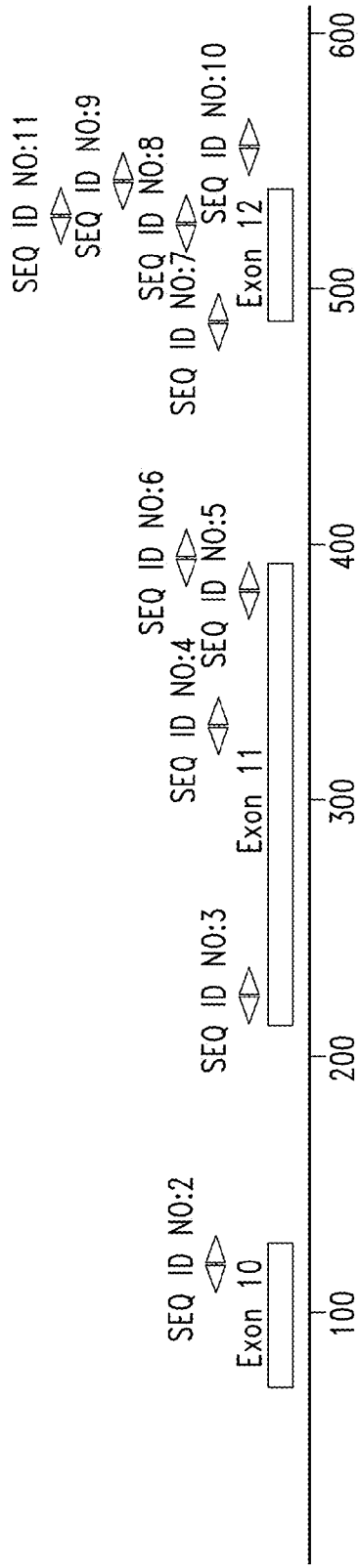

FIG. 3 shows the location of the exemplary human IL-17RC targeting sequences relative to exons 10-12.

Figure 4A:
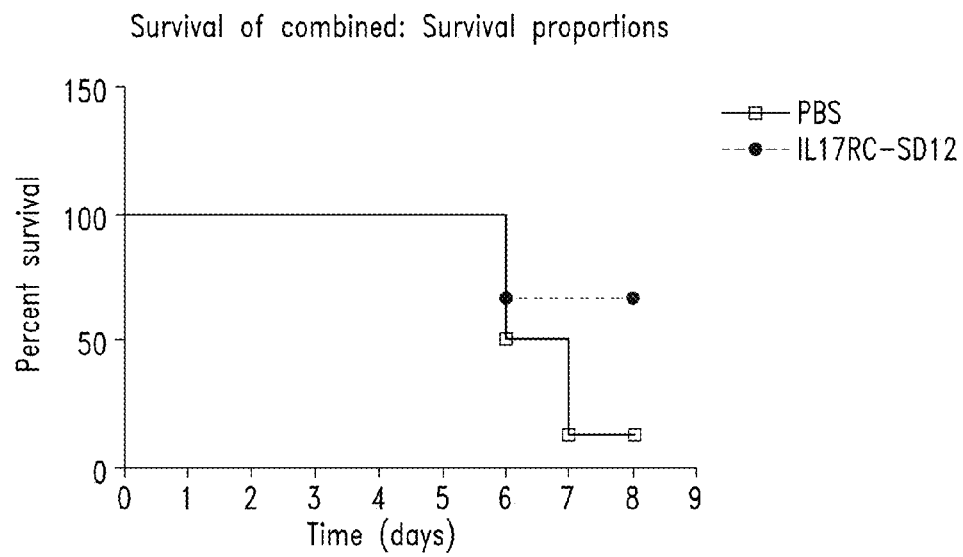
Figure 4B:
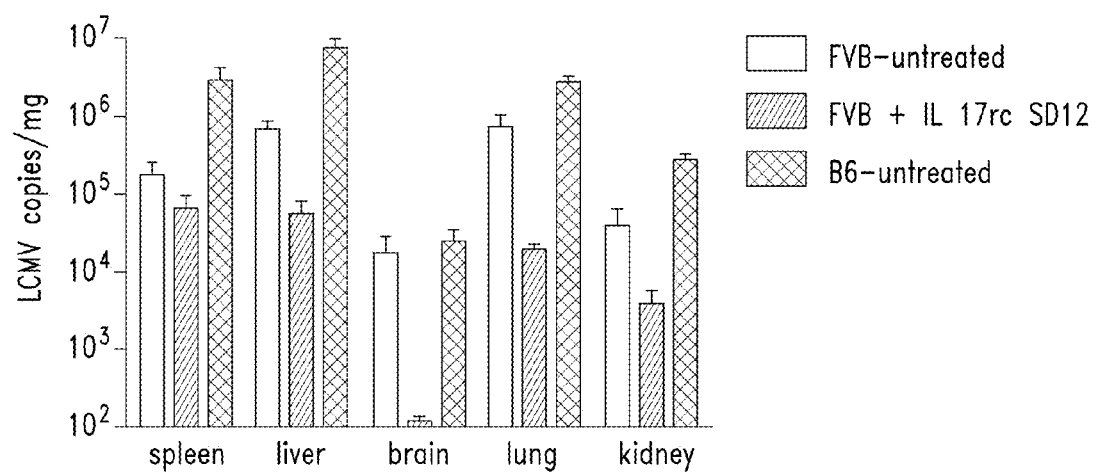

FIG. 4A shows the survival of FVB mice infected with LCMV Cl 13 (LCMV) and treated with muIL-17RC SD12 as described in Example 2. FIG. 4B shows LCMV viral RNA copy numbers after treatment with IL17RC-SD12.

Figure 5:
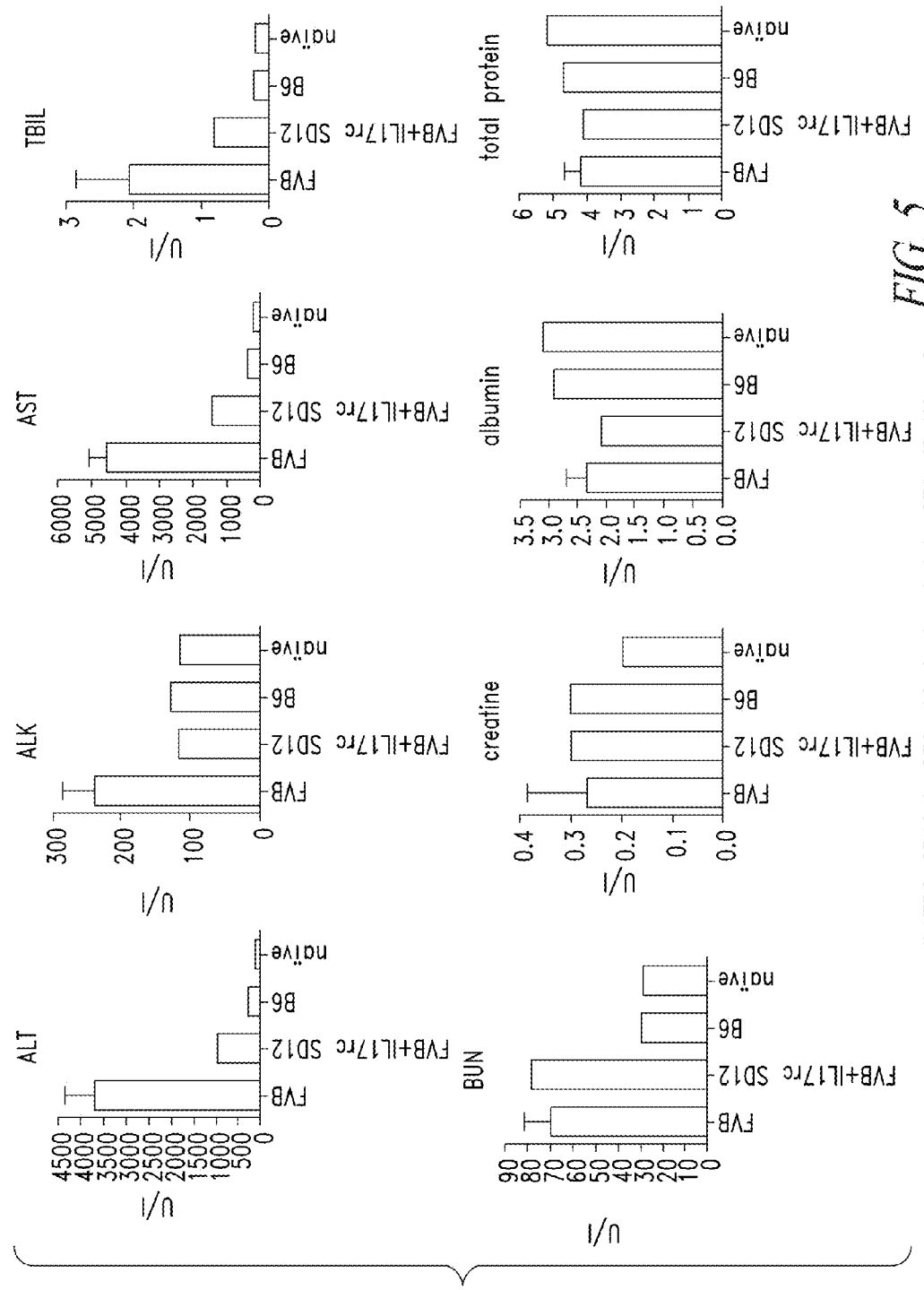

FIG. 5 shows the blood chemistry results from LCMV-infected FVB mice treated with muIL-17RC SD12 compared to LCMV infected but untreated FVB and B6 mice.

Figure 6:
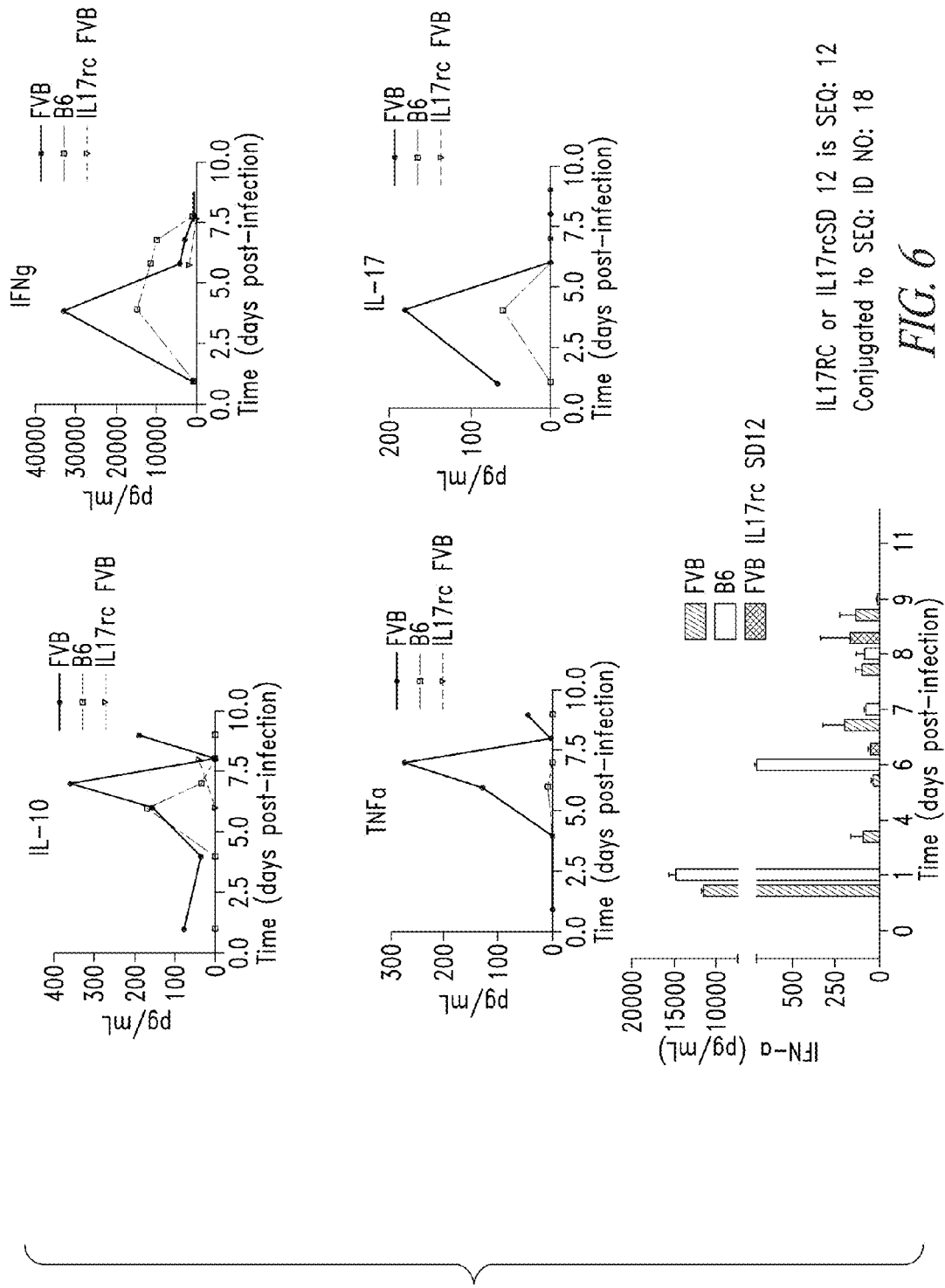

FIG. 6 shows the levels of IL-10, IFNgamma, TNFalpha, IL-17 and IFNalpha in IL-17RC-SD12 treated, LCMV-infected FVB mice compared to untreated and infected FVB and B6 mice.

Figures 7A, 7B:
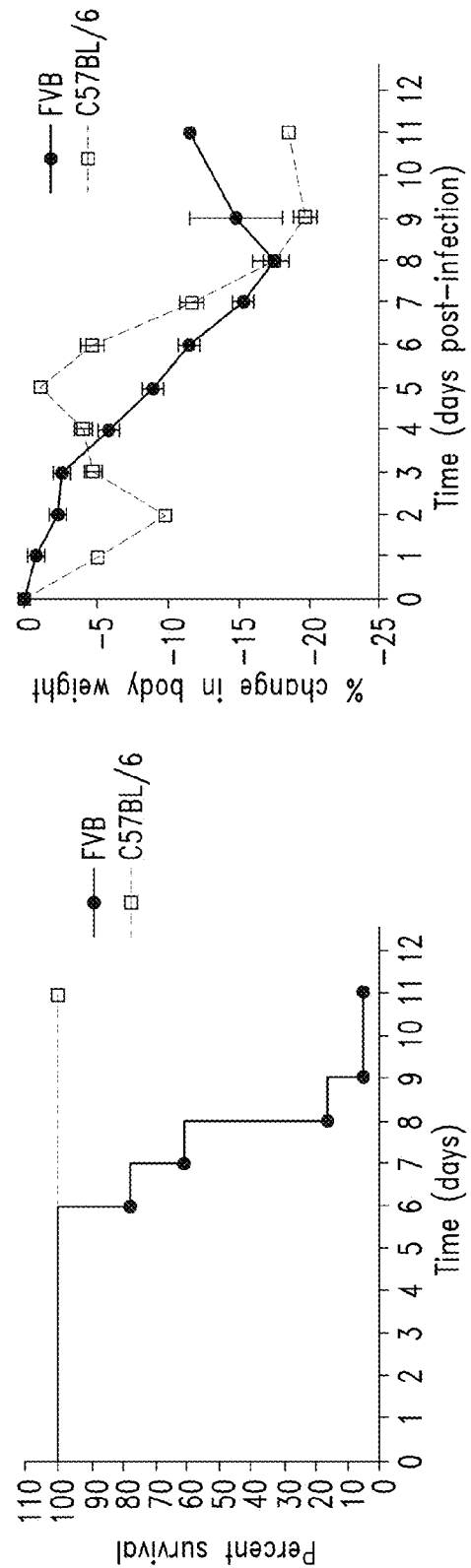
Figure 8B:
Figure 8C:
Figure 8E:
Figure 8A:
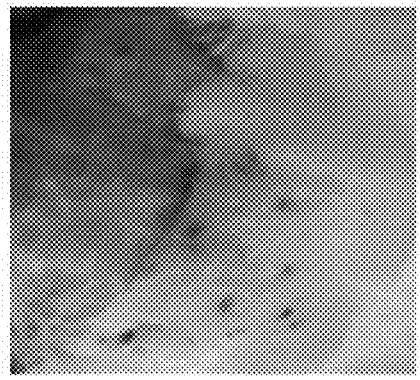
Figure 8D:
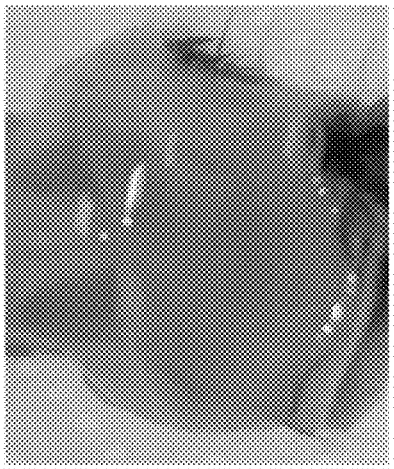

FIGS. 7A and 7B show the lethality and weight loss, respectively, of LCMV-infected FVB mice compared to LCMV-infected C57BL/6 mice.

FIGS. 8A-8E show the hemorrhagic symptoms displayed by LCMV-infected FVB mice (8A-8C) compared to LCMV-infected C57BL/6 or naïve FVB mice (8D & 8E, respectively).

Figure 9:
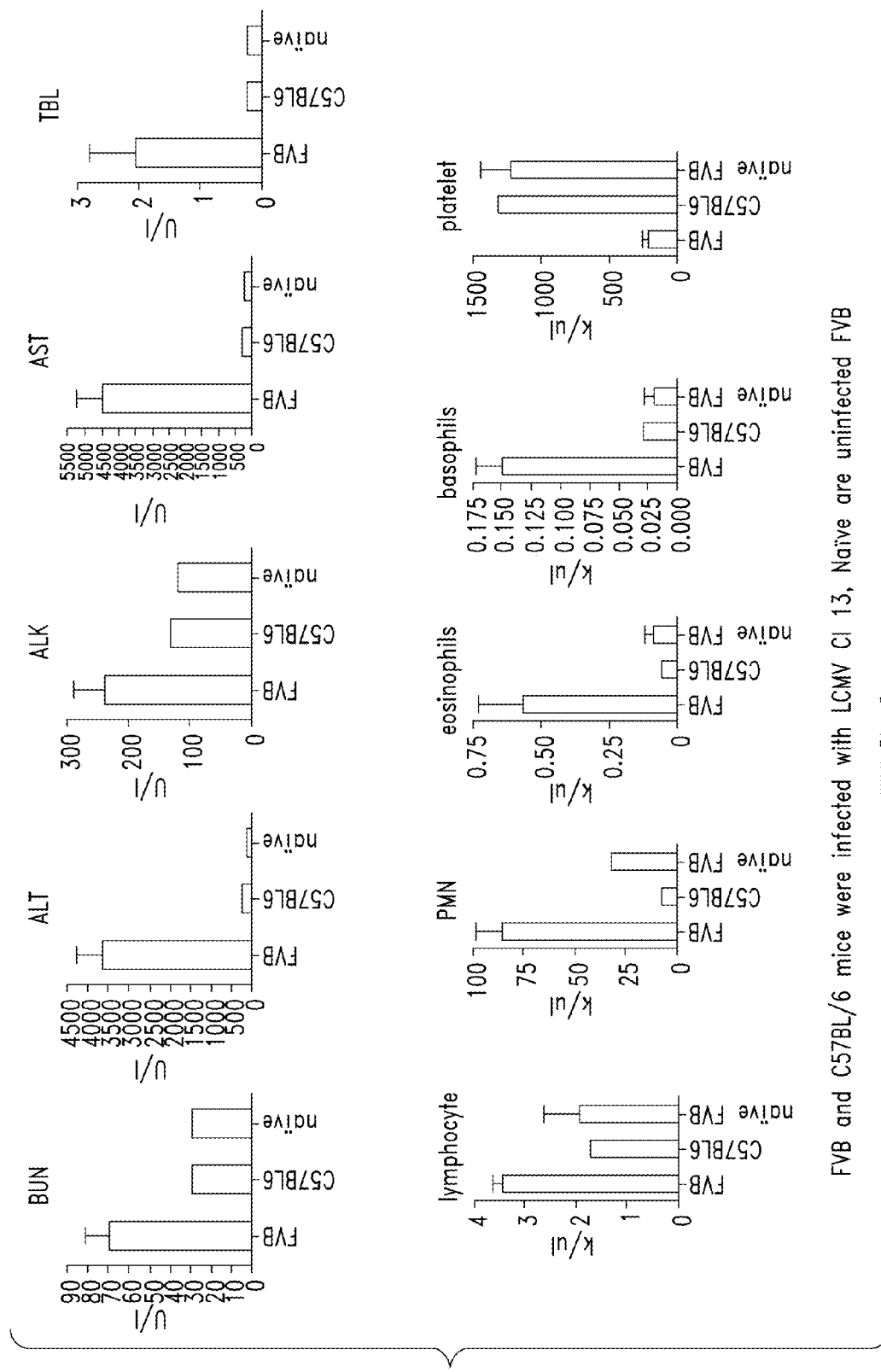

FIG. 9 shows the blood chemistry and hematological profile of LCMV-infected FVB mice compared to LCMV-infected C57BL/6 or naïve FVB mice.

Figure 10:
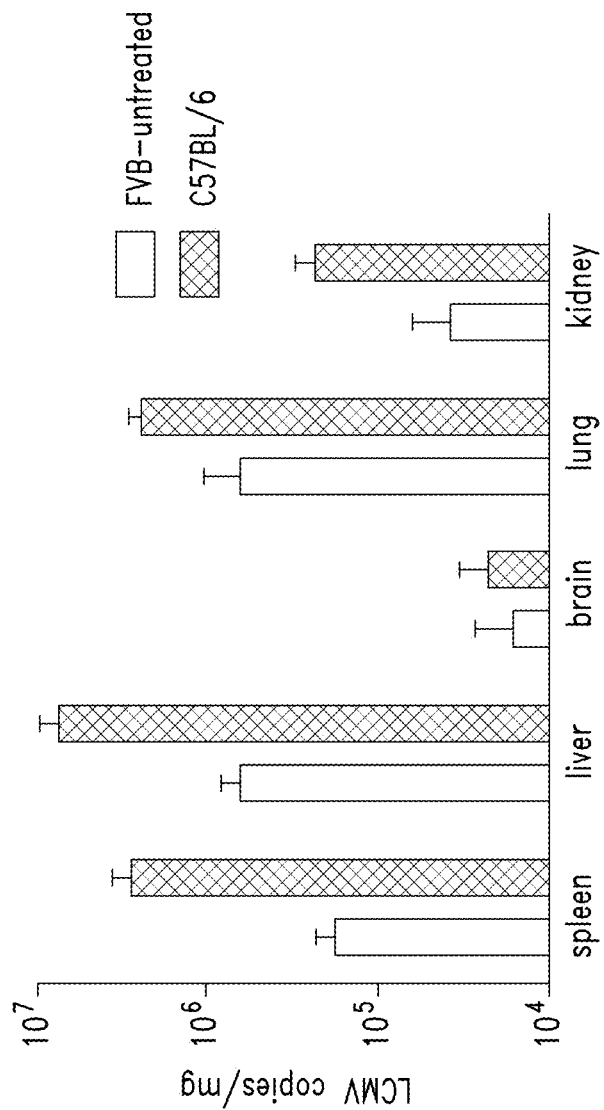

FIG. 10 shows the LCMV viral RNA copy number within various tissues taken from LCMV-infected FVB mice compared to LCMV-infected C57BL/6 mice.

BRIEF SUMMARY OF THE INVENTION

The present invention relates to antisense oligomers targeted to the IL-23/17 signaling pathways. There are several antisense or RNA interference chemistries available and known to those skilled in the art. One important feature of certain antisense chemistries is the ability to hybridize to a target RNA without causing degradation of the target by RNase H, as with 2'-deoxy oligonucleotides ("antisense oligonucleotides" hereafter "AON"). Such compounds may also be referred to as splice-switching oligomers (SSOs) if they alter pre-mRNA splicing and translation suppressing oligomers (TSOs) if they block mRNA translation. Those skilled in the art will appreciate that TSOs and SSOs include, but are not limited to, 2' O-modified oligonucleotides and ribonucleosidephosphorothioates as well as peptide nucleic acids (PNA), morpholinos, locked nucleic acids (LNA), and other polymers lacking ribofuranosyl-based linkages.

Embodiments of the present invention therefore include methods of modulating IL-17 and/or IL-23 signaling activity in a cell, comprising contacting the cell with an antisense oligomer composed of morpholino subunits linked by phosphorus-containing intersubunit linkages joining a morpholino nitrogen of one subunit to a 5' exocyclic carbon of an adjacent subunit, wherein the oligonucleotide contains between 10-40 bases and a targeting sequence of at least 10 contiguous bases complementary to a target sequence, wherein the target sequence is a pre-mRNA transcript of a protein selected from IL-17, IL-23, IL-17RA, IL-17RC and IL-23R, thereby modulating IL-17 and/or IL-23 signaling activity in the cell. In certain embodiments, the oligomer alters splicing of the pre-mRNA transcript and increases expression of a variant at least one of IL-17, IL-23, IL-17RA, IL-17RC or IL-23R.

In certain embodiments, the oligomer induces full or partial exon-skipping of one or more exons of the pre-mRNA transcript. In some embodiments, the one or more exons encode at least a portion of a ligand-binding domain of the protein, and the variant is a ligand independent form of the protein. In particular embodiments, the one or more exons encode at least a portion of a transmembrane domain of the protein, and the variant has reduced membrane binding, increased solubility, or both. In other embodiments, the one or more exons encode at least a portion of a signaling domain of the protein, and the variant has altered IL-17 and/or IL-23 signaling activity.

In certain embodiments, the targeting sequence is complementary to at least a portion of exon 1, 2, or 3 of human IL-17 (e.g., IL-17A, IL-17B, IL-17C, IL-17D, IL-17E and IL-17F), or a proximal intronic sequence. In certain embodiments, the targeting sequence is complementary to at least a portion of exon 1, 2, 3, or 4 of human IL-23, or a proximal intronic sequence.

In certain embodiments, the targeting sequence is complementary to at least a portion of exon 1, 2, 3, 4, 5, 6, 7, 8, 9, 10, 11, 12, or 13 of human IL-17RA, or a proximal intronic sequence. In certain embodiments, the targeting sequence is complementary to at least a portion of exon 1, 2, 3, 4, 5, 6, 7, 8, 9, 10, 11, 12, 13, 14, 15, 16, 17, 18, or 19 of human IL-17RC, or a proximal intronic sequence. In specific embodiments, the targeting sequence is complementary to at least a portion of exon 10, 11, or 12 of human IL-17RC. In particularly embodiments, the targeting sequence is complementary to a splice junction of exon 10, 11, or 12 of human IL-17RC. In certain embodiments, the targeting sequence is complementary to an entirely intra-exonic sequence of exon 10, 11, or 12 of human IL-17RC. In specific embodiments, the targeting sequence is selected from SEQ ID NOS:2-14.

In certain embodiments, the targeting sequence is complementary to at least a portion of exon 1, 2, 3, 4, 5, 6, 7, 8, 9, 10, or 11 of IL-23R. In certain embodiments, the oligomer agonizes an IL-17 and/or IL-23 signaling activity of the protein. In other embodiments, the oligomer antagonizes an IL-17 and/or IL-23 signaling activity of the protein.

In some embodiments, the cell is in a subject. Certain embodiments include reducing inflammation or an inflammatory response in the subject. Other embodiments include increasing inflammation or an inflammatory response in the subject. In specific embodiments, the subject has viral hemorrhagic fever (VHF).

Also included are substantially uncharged antisense oligomers, composed of morpholino subunits linked by phosphorus-containing intersubunit linkages joining a morpholino nitrogen of one subunit to a 5' exocyclic carbon of an adjacent subunit, wherein the oligonucleotide contains between 10-40 bases and a targeting sequence of at least 10 contiguous bases complementary to a target sequence, wherein the target sequence is a pre-mRNA transcript of a protein selected from IL-17, IL-23, IL-17RA, IL-17RC and IL-23R. In certain embodiments, the oligomer contains about 5%-50% intersubunit cationic linkages. In certain embodiments, the oligomer comprises an arginine-rich carrier peptide.

In certain embodiments, the peptide is linked at its C-terminus to the 5' end of the oligonucleotide through a one- or two-amino acid linker. In other embodiments, the peptide is linked at its C-terminus to the 3' end of the oligonucleotide through a one- or two-amino acid linker. In specific embodiments, the linker is AhxβAla, wherein Ahx is 6-amino hexanoic acid and βAla is β-alanine. In certain embodiments, the peptide is selected from SEQ ID NOS:18-26.

In some embodiments, the morpholino subunits in the oligonucleotide are joined by phosphorodiamidate linkages, in accordance with the structure:

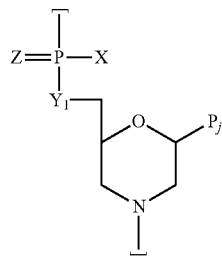

wherein Z is S or O,
X=NR$^1$R$^2$ or OR$^6$,
Y=O or NR$^7$,
and each said linkage is selected from:
(a) uncharged linkage (a), wherein each of R$^1$, R$^2$, R$^6$, and R$^7$ is independently selected from hydrogen and lower alkyl;
(b1) cationic linkage (b1), wherein X=NR$^1$R$^2$ and Y=O, and NR$^1$R$^2$ represents an optional substituted piperazino group, such that R$^1$R$^2$=—CHRCHRN(R$^3$)(R$^4$)CHRCHR—, wherein
each R$^4$ is H, CH$_3$ or null, and
R3 is selected from H, lower alkyl, C(=NH)NH$_2$, Z-L-NHC(=NH)NH$_2$, and
[C(O)CHR'NH]$_m$H, wherein where Z is carbonyl (C(O)) or a direct bond, L is an optional linker up to 18 atoms in length having bonds selected from alkyl, alkoxy, and alkylamino, R' is a side chain of a naturally occurring amino acid or a one- or two-carbon homolog thereof, and m is 1 to 6;
(b2) cationic linkage (b2), wherein X=NR$^1$R$^2$ and Y=O, R$^1$=H or CH$_3$, and R$^2$=LNR$^3$R$^4$R$^5$, wherein L, R$^3$, and R$^4$ are defined as above, and R$^5$ is H, lower alkyl, or lower (alkoxy) alkyl; and
(b3) cationic linkage (b3), wherein Y=NR$^7$ and X=OR$^6$, and R7=LNR$^3$R$^4$R$^5$. wherein L, R$^3$, and R$^4$ and R$^5$ are defined as above, and R$^6$ is H or lower alkyl; and at least one said linkage is selected from cationic linkages (b1), (b2), and (b3).

In certain embodiments, each of R$^1$ and R$^2$, in linkages of type (a), is methyl. In some embodiments, at least one linkage is of type (b1), where each R is H, R$^4$ is H, CH$_3$, or an electron pair, and R$^3$ is selected from H, CH$_3$, C(=NH)NH$_2$, and C(O)-L-NHC(=NH)NH$_2$. In certain embodiments, at least one linkage is of type (b1), where each R is H, R$^4$ is an electron pair, and R$^3$ is selected from C(=NH)NH$_2$ and C(O)-L-NHC(=NH)NH$_2$. In certain embodiments, at least one linkage is of type (b1), where each R is H, R$^4$ is an electron pair, and R$^3$ is selected from C(=NH)NH$_2$ and C(O)-L-NHC(=NH)NH$_2$. In certain embodiments, R$^3$ is C(O)-L-NHC(NH)NH2, and L is a hydrocarbon having the structure —(CH$_2$)$_n$—, where n is 1 to 12. In certain embodiments, at least one linkage is of type (b1), where each R is H, and each of R$^3$ and R$^4$ is independently H or CH$_3$.

Also included are methods of modulating inflammation in a subject, comprising administering to the subject an antisense oligomer composed of morpholino subunits linked by phosphorus-containing intersubunit linkages joining a morpholino nitrogen of one subunit to a 5' exocyclic carbon of an adjacent subunit, wherein the oligonucleotide contains between 10-40 bases and a targeting sequence of at least 10 contiguous bases complementary to a target sequence, wherein the target sequence is a pre-mRNA transcript of a protein selected from IL-17, IL-23, IL-17RA, IL-17RC and IL-23R, thereby modulating inflammation in the subject. Particular embodiments include treating viral hemorrhagic fever (VHF). In certain embodiments, the VHF is caused by a virus selected from the Arenaviridae, Flaviviridae, Filoviridae, Togaviridae, Arteriviridae and Bunyaviridae viral families.

Some embodiments include reducing an acute inflammatory response, reducing a chronic inflammatory response, or both. Other embodiments include increasing an acute inflammatory response, increasing a chronic inflammatory response, or both. Certain embodiments include modulating the activation, inflammatory molecule secretion, proliferation, activity, migration, or adhesion of one or more immune cells or vascular cells. Particular embodiments include modulating the levels or activity of one or more inflammatory molecules. In certain embodiments, the one or more inflammatory molecules comprise plasma-derived inflammatory molecules of any one or more of the complement system, kinin system, coagulation system, or fibrinolysis system. In certain embodiments, the one or more inflammatory molecules comprise cell-derived inflammatory molecules of any one or more of lysosome granules, vasoactive amines, eicosanoids, cytokines, acute-phase proteins, or nitric oxide.

Certain embodiments include modulating an inflammatory response or inflammatory condition associated with one or more tissues, tissue systems, or organs selected from skin, hair follicles, nervous system, auditory system or balance organs, respiratory system, gastroesophogeal tissues, gastrointestinal system, vascular system, liver, gallbladder, lymphatic/immune system, uro-genital system, musculoskeletal system, adipose tissue, mammaries, and endocrine system.

Some embodiments relate to treating inflammation associated with hypersensitivity, an auto-inflammatory condition, cancer, systemic inflammatory response syndrome (SIRS), or cytokine storm. Some embodiments include treating inflammation associated with any one or more of granulomatous inflammation, fibrinous inflammation, purulent inflammation, serous inflammation, or ulcerative inflammation. Certain embodiments comprise treating inflammation associated with one or more wounds. Specific embodiments relate to treating inflammation associated with chronic obstructive pulmonary disorder (COPD). Certain embodiments include increasing the inflammatory response to treat a primary or secondary immunodeficiency.

Some embodiments relate to pharmaceutical compositions, comprising an antisense oligomer described herein and a pharmaceutically acceptable carrier.

Also included are methods of identifying a compound that modulates IL-17 and/or IL-23 signaling activity, comprising (a) contacting a lymphocytic choriogenic meningitis virus (LCMV)-infected FVB mouse with a test compound; (b) measuring one or more symptoms of hemorrhagic fever in the FVB mouse, wherein a difference of one or more symptoms compared to control FVB mouse or a pre-determined value indicates that the test compound modulates IL-17 and/or IL-23 signaling, thereby identifying the compound that modulates IL-17 and/or IL-23 signaling activity.

In certain embodiments, the test compound is an antisense oligonucleotide, an RNAi agent, an antibody or antigen-binding fragment thereof, a soluble receptors, an adnectin, a peptide, a peptide mimetic, an aptamer, or a small molecule. In certain embodiments, the one or more symptoms are selected from cutaneous hemorrhaging, mucosal hemorrhaging, dizziness, liver petechiae, hypovolemic shock, leukopenia, thrombocytopenia, and death. In some embodiments, the compound is for treatment of a disease or condition associated with IL-17 and/or IL-23 signaling. In certain embodiments, the diseases or condition is an inflammatory disease or condition. In certain embodiments, the inflammatory disease or condition is selected from viral hemorrhagic fever, asthma, allergic asthma, inflammatory bowel disease, ulcerative colitis, Crohn's disease, arthritis, atopic dermatitis or psoriasis, endotoxemia, septicemia, toxic shock syndrome, rheumatoid arthritis, hepatobiliary disease, atherosclerosis, promotion of tumor growth, degenerative joint disease, immune mediated renal disease, adult respiratory disease (ARD), septic shock, multiple organ failure, inflammatory lung injury, chronic obstructive pulmonary disease (COPD), airway hyper-responsiveness, chronic bronchitis, allergic asthma, bacterial pneumonia, psoriasis, eczema, systemic lupus erythematosus (SLE), multiple sclerosis, systemic sclerosis, nephrotic syndrome, organ allograft rejection, graft vs. host disease (GVHD), kidney, lung, heart, etc. transplant rejection, streptococcal cell wall (SCW)-induced arthritis, osteoarthritis, gingivitis/periodontitis, herpetic stromal keratitis, cancers including prostate, renal, colon, ovarian, cervical, leukemia, angiogenesis, restenosis and Kawasaki disease.

Also included are methods of identifying a compound for the treatment of viral hemorrhagic fever (HFV), comprising (a) contacting an LCMV-infected FVB mouse with a test compound; (b) measuring one or more symptoms of hemorrhagic fever in the FVB mouse, wherein a difference of one or more symptoms compared to a control FVB mouse or a pre-determined value indicates that the test compound treats VHF, thereby identifying the compound for the treatment of VHF.

In certain embodiments, the test compound is an antisense oligonucleotide, an RNAi agent, an antibody or antigen-binding fragment thereof, a soluble receptors, an adnectin, a peptide, a peptide mimetic, an aptamer, or a small molecule. In certain embodiments, the one or more symptoms are selected from cutaneous hemorrhaging, mucosal hemorrhaging, dizziness, liver petechiae, hypovolemic shock, leukopenia, thrombocytopenia, viral load, and death. In specific embodiments, VHF is caused by a virus selected from the Arenaviridae, Flaviviridae, Filoviridae, Togaviridae, Arteriviridae and Bunyaviridae viral families.

Also included are animal models for identifying an agent that modulates IL-17 and/or IL-23 signaling activity, comprising a lymphocytic choriogenic meningitis virus (LCMV)-infected FVB mouse, and a test compound that modulates IL-17 and/or IL-23 signaling activity, and/or reduces LCMV replication. In certain embodiments, the test compound is an antisense oligonucleotide, an RNAi agent, an antibody or antigen-binding fragment thereof, a soluble receptors, an adnectin, a peptide, a peptide mimetic, an aptamer, or a small molecule. In certain embodiments, the test compound specifically binds to any one or more of IL-17, IL-23, IL-17RA, IL-17RC and IL-23R. In other embodiments, the test compound is an antisense oligonucleotide that contains between 10-40 bases and a targeting sequence of at least 10 contiguous bases complementary to a target sequence, wherein the target sequence is a pre-mRNA transcript of a protein selected from IL-17, IL-23, IL-17RA, IL-17RC and IL-23R.

DETAILED DESCRIPTION OF THE INVENTION

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length.

An "agonist" refers to an agent that intensifies or mimics a selected biological activity of IL-17 or IL-23. Examples of such biological activities include transactivation and transrepression. Included are partial and full agonists.

The term "antagonist" refers to an agent that inhibits or attenuates a selected biological activity of IL-17 or IL-23. Examples of such biological activities include transactivation and transrepression. Included are partial and full antagonists.

By "coding sequence" is meant any nucleic acid sequence that contributes to the code for the polypeptide product of a gene. By contrast, the term "non-coding sequence" refers to any nucleic acid sequence that does not contribute to the code for the polypeptide product of a gene.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. While perfect complementarity is often desired, some embodiments can include one or more but preferably 6, 5, 4, 3, 2, or 1 mismatches with respect to the target RNA. Variations at any location within the oligomer are included. In certain embodiments, variations in sequence near the termini of an oligomer are generally preferable to variations in the interior, and if present are typically within about 6, 5, 4, 3, 2, or 1 nucleotides of the 5' and/or 3' terminus.

The terms "cell penetrating peptide" or "CPP" are used interchangeably and refer to cationic cell penetrating peptides, also called transport peptides, carrier peptides, arginine-rich delivery peptides, or peptide transduction domains. The peptides, as shown herein, have the capability of inducing cell penetration within 30%, 40%, 50%, 60%, 70%, 80%, 90%, or 100% of cells of a given cell culture population, including all integers in between, and allow macromolecular translocation within multiple tissues in vivo upon systemic administration.

The terms "antisense oligomer" or "antisense compound" or "antisense oligonucleotide" or "oligonucleotide" are used interchangeably and refer to a sequence of cyclic subunits, each bearing a base-pairing moiety, linked by intersubunit linkages that allow the base-pairing moieties to hybridize to a target sequence in a nucleic acid (typically an RNA) by Watson-Crick base pairing, to form a nucleic acid:oligomer heteroduplex within the target sequence. The cyclic subunits may be based on ribose or another pentose sugar or, in certain embodiments, a morpholino group (see description of morpholino oligomers below). Also contemplated are peptide nucleic acids (PNAs), locked nucleic acids (LNAs), 2'-O-Methyl oligonucleotides and RNA interference agents (siRNA agents), and other antisense agents known in the art.

Such an antisense oligomer can be designed to block or inhibit translation of mRNA or to inhibit natural pre-mRNA splice processing, or induce degradation of targeted mRNAs, and may be said to be "directed to" or "targeted against" a target sequence with which it hybridizes. In certain embodiments, the target sequence includes a region including an AUG start codon of an mRNA, a 3' or 5' splice site of a pre-processed mRNA, a branch point. The target sequence may be within an exon or within an intron. The target sequence for a splice site may include an mRNA sequence having its 5' end 1 to about 25 base pairs downstream of a normal splice acceptor junction in a preprocessed mRNA (pre-mRNA). A preferred target sequence for a splice is any region of a preprocessed mRNA that includes a splice site or is contained entirely within an exon coding sequence or spans a splice acceptor or donor site. An oligomer is more generally said to be "targeted against" a biologically relevant target, such as an IL-17, IL-23, IL-17RA, IL-17RC or IL-23R mRNA or pre-mRNA, when it is targeted against the nucleic acid of the target in the manner described above.

The "IL-23/17 signaling pathway" describes the functioning cytokine and cytokine receptor proteins encoded by the IL-17, IL-23, IL-17RA, IL-17RC and IL-23R genes also referred to as "IL-23/17 signaling targets" or "IL-23/17 signaling genes." The term "IL-17 gene" refers to a gene family of six related but distinct genes named IL-17A, IL-17B, IL-17C, IL-17D, IL-17E and IL-17F. Preferred targets in practicing the invention are the genes encoding IL-17A and IL-17F.

Included are antisense oligonucleotides that comprise, consist essentially of, or consist of one or more of SEQ ID NOS:2-12. Also included are variants of these antisense oligomers, including variant oligomers having 80%, 85%, 90%, 95%, 97%, 98%, or 99% (including all integers in between) sequence identity or sequence homology to any one of SEQ ID NOS:2-12, and/or variants that differ from these sequences by about 1, 2, 3, 4, 5, 6, 7, 8, 9, or 10 nucleotides, preferably those variants that modulate IL-17RC expression in a cell. Also included are oligonucleotides of any one or more of SEQ ID NOS:2-12, which comprise a suitable number of charged linkages, as described herein, e.g., up to about 1 per every 2-5 uncharged linkages, such as about 4-5 per every 10 uncharged linkages, and/or which comprise an Arg-rich peptide attached thereto, as also described herein.

The terms "morpholino oligomer" or "PMO" (phosphoramidate- or phosphorodiamidate morpholino oligomer) refer to an oligonucleotide analog composed of morpholino subunit structures, where (i) the structures are linked together by phosphorus-containing linkages, one to three atoms long, preferably two atoms long, and preferably uncharged or cationic, joining the morpholino nitrogen of one subunit to a 5' exocyclic carbon of an adjacent subunit, and (ii) each morpholino ring bears a purine or pyrimidine or an equivalent base-pairing moiety effective to bind, by base specific hydrogen bonding, to a base in a polynucleotide. See, for example, the structure in FIG. 1A, which shows a preferred phosphorodiamidate linkage type. Variations can be made to this linkage as long as they do not interfere with binding or activity. For example, the oxygen attached to phosphorus may be substituted with sulfur (thiophosphorodiamidate). The 5' oxygen may be substituted with amino or lower alkyl substituted amino. The pendant nitrogen attached to phosphorus may be unsubstituted, monosubstituted, or disubstituted with (optionally substituted) lower alkyl. See also the discussion of cationic linkages below. The purine or pyrimidine base pairing moiety is typically adenine, cytosine, guanine, uracil, thymine or inosine. The synthesis, structures, and binding characteristics of morpholino oligomers are detailed in U.S. Pat. Nos. 5,698,685, 5,217,866, 5,142,047, 5,034,506, 5,166, 315, 5,521,063, and 5,506,337, and PCT Appn. Nos. PCT/US07/11435 (cationic linkages) and US08/012804 (improved synthesis), all of which are incorporated herein by reference.

The term "oligonucleotide analog" refers to an oligonucleotide having (i) a modified backbone structure, e.g., a backbone other than the standard phosphodiester linkage found in natural oligo- and polynucleotides, and (ii) optionally, modified sugar moieties, e.g., morpholino moieties rather than ribose or deoxyribose moieties. Oligonucleotide analogs support bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). Preferred analogs are those having a substantially uncharged, phosphorus containing backbone.

A substantially uncharged, phosphorus containing backbone in an oligonucleotide analog is one in which a majority of the subunit linkages, e.g., between 50-100%, typically at least 60% to 100% or 75% or 80% of its linkages, are uncharged at physiological pH, and contain a single phosphorous atom. Antisense oligonucleotides and oligonucleotide analogs may contain between about 8 and 40 subunits, typically about 8-25 subunits, and preferably about 12 to 25 subunits. In certain embodiments, oligonucleotides may have exact sequence complementarity to the target sequence or near complementarity, as defined below.

Figure 1B:
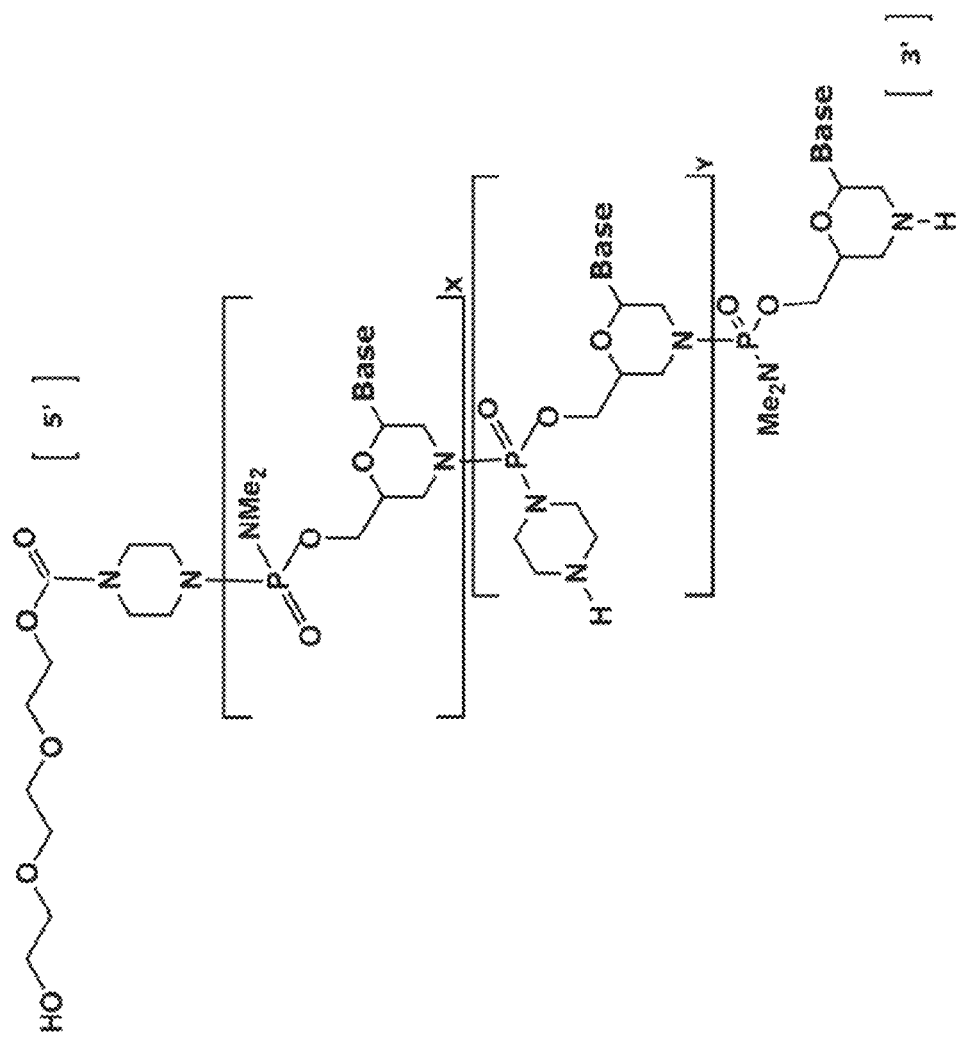
FIG. 1B shows a morpholino oligomer as in FIG. 1A, but where the backbone linkages contain one positively charged group in the form of a (piperazino) phosphorodiamidate linkage.

A "subunit" of an oligonucleotide refers to one nucleotide (or nucleotide analog) unit. The term may refer to the nucleotide unit with or without the attached intersubunit linkage, although, when referring to a "charged subunit", the charge typically resides within the intersubunit linkage (e.g., a phosphate or phosphorothioate linkage or a cationic linkage, as shown in FIG. 1B).

The purine or pyrimidine base pairing moiety is typically adenine, cytosine, guanine, uracil, thymine or inosine. Also included are bases such as pyridin-4-one, pyridin-2-one, phenyl, pseudouracil, 2,4,6-trime115thoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, quesosine, 2-thiouridine, 4-thiouridine, wybutosine, wybutoxosine, 4-acetyltidine, 5-(carboxyhydroxymethyl)uridine, 5'-carboxymethylaminomethyl-2-thiouridine, 5-carboxymethylaminomethyluridine, β-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonyhnethyluridine, 5-methyloxyuridine, 5-methyl-2-thiouridine, 2-methylthio-N6-isopentenyladenosine, β-D-mannosylqueosine, uridine-5-oxyacetic acid, 2-thiocytidine, threonine derivatives and others (Burgin et al., 1996, Biochemistry, 35, 14090; Uhlman & Peyman, supra). By "modified bases" in this aspect is meant nucleotide bases other than adenine (A), guanine (G), cytosine (C), thymine (T), and uracil (U), as illustrated above; such bases can be used at any position in the antisense molecule. Persons skilled in the art will appreciate that depending on the uses of the oligomers, Ts and Us are interchangeable. For instance, with other antisense chemistries such as 2'-O-methyl antisense oligonucleotides that are more RNA-like, the T bases may be shown as U (see, e.g., Sequence Listing).

An "amino acid subunit" or "amino acid residue" can refer to an α-amino acid residue (—CO—CHR—NH—) or a β- or other amino acid residue (e.g., —CO—$(CH_2)_n$CHR—NH—), where R is a side chain (which may include hydrogen) and n is 1 to 7, preferably 1 to 4.

The term "naturally occurring amino acid" refers to an amino acid present in proteins found in nature, such as the 20 (L)-amino acids utilized during protein biosynthesis as well as others such as 4-hydroxyproline, hydroxylysine, desmosine, isodesmosine, homocysteine, citrulline and ornithine. The term "non-natural amino acids" refers to those amino acids not present in proteins found in nature, examples include beta-alanine (β-Ala), 6-aminohexanoic acid (Ahx) and 6-aminopentanoic acid. Additional examples of "non-natural amino acids" include, without limitation, (D)-amino acids, norleucine, norvaline, p-fluorophenylalanine, ethionine and the like, which are known to a person skilled in the art.

By "isolated" is meant material that is substantially or essentially free from components that normally accompany it in its native state. For example, an "isolated polynucleotide" or "isolated oligonucleotide," as used herein, may refer to a polynucleotide that has been purified or removed from the sequences that flank it in a naturally-occurring state, e.g., a DNA fragment that has been removed from the sequences that are normally adjacent to the fragment.

An "effective amount" or "therapeutically effective amount" refers to an amount of therapeutic compound, such as an antisense oligomer or RNA interference agent (e.g., siRNA), administered to a mammalian subject, either as a single dose or as part of a series of doses, which is effective to produce a desired therapeutic effect. For an antisense oligomer, this effect is typically brought about by inhibiting translation or natural splice-processing of a selected target sequence. An "effective amount," targeted against an IL-17, IL-23, IL-17RA, IL-17RC or IL-23R transcript, also relates to an amount effective to modulate expression of the IL-23/17 signaling genes.

By "enhance" or "enhancing," or "increase" or "increasing," or "stimulate" or "stimulating," refers generally to the ability of one or antisense or RNAi compounds or compositions to produce or cause a greater physiological response (i.e., downstream effects) in a cell or a subject, as compared to the response caused by either no antisense compound or a control compound. An "increased" or "enhanced" amount is typically a "statistically significant" amount, and may include an increase that is 1.1, 1.2, 2, 3, 4, 5, 6, 7, 8, 9, 10, 15, 20, 30, 40, 50 or more times (e.g., 500, 1000 times) (including all integers and decimal points in between and above 1), e.g., 1.5, 1.6, 1.7. 1.8, etc.) the amount produced by no antisense compound (the absence of an agent) or a control compound.

The term "reduce" or "inhibit" may relate generally to the ability of one or more antisense or RNAi compounds of the invention to "decrease" a relevant physiological or cellular response, such as a symptom of a disease or condition described herein, as measured according to routine techniques in the diagnostic art. Relevant physiological or cellular responses (in vivo or in vitro) will be apparent to persons skilled in the art, and may include, for example, reductions in inflammation. A "decrease" in a response may be "statistically significant" as compared to the response produced by no antisense compound or a control composition, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers in between.

The term "target sequence" refers to a portion of the target RNA against which the oligonucleotide or antisense agent is directed, that is, the sequence to which the oligonucleotide will hybridize by Watson-Crick base pairing of a complementary sequence. In certain embodiments, the target sequence may be a contiguous region of a pre-mRNA that includes both intron and exon target sequence. In certain other embodiments, the target sequence will consist exclusively of either intron or exon sequences.

The term "targeting sequence" or "antisense targeting sequence" refers to the sequence in an oligonucleotide or other antisense agent that is complementary (meaning, in addition, substantially complementary) to the target sequence in the RNA genome. The entire sequence, or only a portion, of the antisense compound may be complementary to the target sequence. For example, in an oligonucleotide having 20-30 bases, about 6, 7, 8, 9, 10, 11, 12, 13, 14, 15, 16, 17, 18, 19, 20, 21, 22, 23, 24, 25, 26, 27, 28, or 29 may be targeting sequences that are complementary to the target region. Typically, the targeting sequence is formed of contiguous bases, but may alternatively be formed of non-contiguous sequences that when placed together, e.g., from opposite ends of the oligonucleotide, constitute sequence that spans the target sequence.

The target and targeting sequences may be selected such that binding of the antisense compound is to a region of a IL-17, IL-23, IL-17RA, IL-17RC or IL-23R pre-mRNA that causes exon skipping of one or more selected exons in those genes.

Target and targeting sequences are described as "complementary" to one another when hybridization occurs in an antiparallel configuration. A targeting sequence may have "near" or "substantial" complementarity to the target sequence and still function for the purpose of the present invention, that is, it may still be functionally "complementary." In certain embodiments, an oligonucleotide may have at most one mismatch with the target sequence out of 10 nucleotides, and preferably at most one mismatch out of 20. Alternatively, an oligonucleotide may have at least 90% sequence homology, and preferably at least 95% sequence homology, with the exemplary antisense targeting sequences described herein.

An oligonucleotide "specifically hybridizes" to a target polynucleotide if the oligomer hybridizes to the target under physiological conditions, with a Tm substantially greater than 45° C., preferably at least 50° C., and typically 60° C.-80° C. or higher. Such hybridization preferably corresponds to stringent hybridization conditions. At a given ionic strength and pH, the Tm is the temperature at which 50% of a target sequence hybridizes to a complementary polynucleotide. Again, such hybridization may occur with "near" or "substantial" complementarity of the antisense oligomer to the target sequence, as well as with exact complementarity.

"Homology" refers to the percentage number of amino acids that are identical or constitute conservative substitutions. Homology may be determined using sequence comparison programs such as GAP (Deveraux et al., 1984, *Nucleic Acids Research* 12, 387-395). In this way sequences of a similar or substantially different length to those cited herein could be compared by insertion of gaps into the alignment, such gaps being determined, for example, by the comparison algorithm used by GAP.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Terms used to describe sequence relationships between two or more polynucleotides or polypeptides include "reference sequence," "comparison window," "sequence identity," "percentage of sequence identity," and "substantial identity". A "reference sequence" is at least 8 or 10 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., "Current Protocols in Molecular Biology," John Wiley & Sons Inc, 1994-1998, Chapter 15.

A "nuclease-resistant" oligomeric molecule (oligomer) refers to one whose backbone is substantially resistant to nuclease cleavage, in non-hybridized or hybridized form; by common extracellular and intracellular nucleases in the body; that is, the oligomer shows little or no nuclease cleavage under normal nuclease conditions in the body to which the oligomer is exposed.

A "heteroduplex" refers to a duplex between an antisense oligonucleotide and the complementary portion of a target RNA. A "nuclease-resistant heteroduplex" refers to a heteroduplex formed by the binding of an antisense oligomer to its complementary target, such that the heteroduplex is substantially resistant to in vivo degradation by intracellular and extracellular nucleases, such as RNaseH, which are capable of cutting double-stranded RNA/RNA or RNA/DNA complexes.

A "base-specific intracellular binding event involving a target RNA" refers to the specific binding of an antisense oligonucleotide to a target RNA sequence inside a cell. The base specificity of such binding is sequence dependent. For example, a single-stranded polynucleotide can specifically bind to a single-stranded polynucleotide that is complementary in sequence.

As used herein, the term "body fluid" encompasses a variety of sample types obtained from a subject including, urine, saliva, plasma, blood, spinal fluid, or other sample of biological origin, such as skin cells or dermal debris, and may refer to cells or cell fragments suspended therein, or the liquid medium and its solutes.

The term "relative amount" is used where a comparison is made between a test measurement and a control measurement. The relative amount of a reagent forming a complex in a reaction is the amount reacting with a test specimen, compared with the amount reacting with a control specimen. The control specimen may be run separately in the same assay, or it may be part of the same sample (for example, normal tissue surrounding a malignant area in a tissue section).

"Treatment" of an individual or a cell is any type of intervention provided as a means to alter the natural course of a disease or pathology in the individual or cell. Treatment includes, but is not limited to, administration of, e.g., a pharmaceutical composition, and may be performed either prophylactically, or subsequent to the initiation of a pathologic event or contact with an etiologic agent. Treatment includes any desirable effect on the symptoms or pathology of a disease or condition associated with inflammation, among others described herein.

Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

An agent is "actively taken up by mammalian cells" when the agent can enter the cell by a mechanism other than passive diffusion across the cell membrane. The agent may be transported, for example, by "active transport," referring to transport of agents across a mammalian cell membrane by e.g., an ATP-dependent transport mechanism, or by "facilitated transport," referring to transport of antisense agents across the cell membrane by a transport mechanism that requires binding of the agent to a transport protein, which then facilitates passage of the bound agent across the membrane. For both active and facilitated transport, oligonucleotide analogs preferably have a substantially uncharged backbone, as defined below.

Alternatively, the antisense compound may be formulated in a complexed form, such as an agent having an anionic backbone complexed with cationic lipids or liposomes, which can be taken into cells by an endocytotic mechanism. The antisense oligonucleotide may also be conjugated, e.g., at its 5' or 3' end, to an arginine-rich peptide, such as a portion of the HIV TAT protein, polyarginine, or to combinations of arginine and other amino acids including the non-natural amino acids 6-aminohexanoic acid (Ahx) and beta-alanine (β-Ala). Exemplary arginine-rich delivery peptides are listed as SEQ ID NOs:15-32. These exemplary arginine-rich delivery peptides facilitate transport into the target host cell as described (Moulton, Nelson et al. 2004).

Hence, included are methods of treating a subject in need thereof, by administering one or more antisense oligomers of the present invention (e.g., SEQ ID NOS: 2-12, and variants thereof), optionally as part of a pharmaceutical formulation or dosage form, to a subject in need thereof. A "subject," as used herein, may include any animal that exhibits a symptom, or is at risk for exhibiting a symptom, which can be treated with an antisense compound of the invention, such as a subject that has or is at risk for having an inflammatory condition. Suitable subjects (patients) include laboratory animals (such as mouse, rat, rabbit, or guinea pig), farm animals, and domestic animals or pets (such as a cat or dog). Non-human primates and, preferably, human patients, are included.

Also contemplated are alternate methods of RNA interference (RNAi), such as those involving double stranded RNA-molecules, or dsRNA. The term "double-stranded" means two separate nucleic acid strands comprising a region in which at least a portion of the strands are sufficiently complementary to hydrogen bond and form a duplex structure. The term "duplex" or "duplex structure" refers to the region of a double stranded molecule wherein the two separate strands are substantially complementary, and thus hybridize to each other.

"dsRNA" refers to a ribonucleic acid molecule having a duplex structure comprising two complementary and antiparallel nucleic acid strands (i.e., the sense and antisense strands). Not all nucleotides of a dsRNA must exhibit Watson-Crick base pairs; the two RNA strands may be substantially complementary. The RNA strands may have the same or a different number of nucleotides. The term "dsRNA" also includes "siRNA" or short interfering RNA.

It will be understood that the term "ribonucleotide" or "nucleotide" can, in the case of a modified RNA or nucleotide surrogate, also refer to a modified nucleotide, or surrogate replacement moiety at one or more positions. Thus, the dsRNA is or includes a region which is at least partially complementary to the target RNA. In certain embodiments, the dsRNA is fully complementary to the target RNA. It is not necessary that there be perfect complementarity between the dsRNA and the target, but the correspondence must be sufficient to enable the dsRNA, or a cleavage product thereof, to direct sequence specific silencing, such as by RNAi cleavage of the target RNA. Complementarity, or degree of homology with the target strand, is most critical in the antisense strand. While perfect complementarity, particularly in the antisense strand, is often desired some embodiments can include one or more but preferably 6, 5, 4, 3, 2, or fewer mismatches with respect to the target RNA. The mismatches are most tolerated in the terminal regions, and if present are preferably in a terminal region or regions, e.g., within 6, 5, 4, or 3 nucleotides of the 5' and/or 3' terminus. The sense strand need only be substantially complementary with the antisense strand to maintain the overall double-strand character of the molecule.

As used herein, "modified dsRNA" refers to a dsRNA molecule that comprises at least one alteration that renders it more resistant to nucleases (e.g., protein kinase) than an identical dsRNA molecule that recognizes the same target RNA. Modified dsRNAs may include a single-stranded nucleotide overhang and/or at least one substituted nucleotide.

As used herein, a "nucleotide overhang" refers to the unpaired nucleotide or nucleotides that protrude from the duplex structure when a 3'-end of one RNA strand extends beyond the 5'-end of the other complementary strand, or vice versa. "Blunt" or "blunt end" means that there are no unpaired nucleotides at that end of the dsRNA, i.e., no nucleotide overhang. A "blunt ended" dsRNA is a dsRNA that is double stranded over its entire length, i.e., no nucleotide overhang at either end of the molecule.

The term "terminal base pair," as used herein, refers to the last nucleotide base pair on one end of the duplex region of a double-stranded molecule. For example, if a dsRNA or other molecule is blunt ended (i.e., has no nucleotide overhangs), the last nucleotide base pairs at both ends of the molecule are terminal base pairs. Where a dsRNA or other molecule has a nucleotide overhang at one or both ends of the duplex structure, the last nucleotide base pair(s) immediately adjacent the nucleotide overhang(s) is the terminal base pair at that end(s) of the molecule.

Also included are vector delivery systems that are capable of expressing the oligomeric, IL17/23 signaling gene-targeted exon skipping sequences of the present invention, such as vectors that express a polynucleotide sequence comprising any one or more of SEQ ID NOS:2-12, or variants thereof, as described herein, or that express a polynucleotide sequence that is complementary to any or more of the target sequences (e.g., SEQ ID NO:1).

By "vector" or "nucleic acid construct" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extra-chromosomal entity, the replication of which is independent of chromosomal replication, e.g., a linear or closed circular plasmid, an extra-chromosomal element, a mini-chromosome, or an artificial chromosome. The vector can contain any means for assuring self-replication. Alternatively, the vector can be one which, when introduced into the host cell, is integrated into the genome and replicated together with the chromosome(s) into which it has been integrated.

A vector or nucleic acid construct system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In the present case, the vector or nucleic acid construct is preferably one which is operably functional in a mammalian cell, such as a muscle cell. The vector can also include a selection marker such as an antibiotic or drug resistance gene, or a reporter gene (i.e., green fluorescent protein, luciferase), that can be used for selection or identification of suitable transformants or transfectants. Exemplary delivery systems may include viral vector systems (i.e., viral-mediated transduction) including, but not limited to, retroviral (e.g., lentiviral) vectors, adenoviral vectors, adeno-associated viral vectors, and herpes viral vectors, among others known in the art.

The term "operably linked" as used herein means placing an oligomer-encoding sequence under the regulatory control of a promoter, which then controls the transcription of the oligomer.

A wild-type gene or gene product is that which is most frequently observed in a population and is thus arbitrarily designed the "normal" or "wild-type" form of the gene.

"Alkyl" refers to a fully saturated monovalent radical containing carbon and hydrogen, which may be branched, linear, or cyclic (cycloalkyl). Examples of alkyl groups are methyl, ethyl, n-butyl, t-butyl, n-heptyl, isopropyl, cyclopropyl, cyclopentyl, ethylcyclopentyl, and cyclohexyl. Generally preferred are alkyl groups having one to six carbon atoms, referred to as "lower alkyl", and exemplified by methyl, ethyl, n-butyl, i-butyl, t-butyl, isoamyl, n-pentyl, and isopentyl. In one embodiment, lower alkyl refers to $C_1$ to $C_4$ alkyl.

"Alkenyl" refers to an unsaturated monovalent radical containing carbon and hydrogen, which may be branched, linear, or cyclic. The alkenyl group may be monounsaturated or polyunsaturated. Generally preferred are alkenyl groups having one to six carbon atoms, referred to as "lower alkenyl."

"Alkynyl" refers to an unsaturated straight or branched chain hydrocarbon radical containing from 2 to 18 carbons comprising at least one carbon to carbon triple bond. Examples include without limitation ethynyl, propynyl, isopropynyl, butynyl, iso-butynyl, tert-butynyl, pentynyl and hexynyl. The term "lower alkynyl" refers to an alkynyl group, as defined herein, containing between 2 and 8 carbons.

"Cycloalkyl" refers to a mono- or poly-cyclic alkyl radical. Examples include without limitation cyclobutyl, cycopentyl, cyclohexyl, cycloheptyl and cyclooctyl.

"Aryl" refers to a substituted or unsubstituted monovalent aromatic radical, generally having a single ring (e.g., phenyl) or two condensed rings (e.g., naphthyl). This term includes heteroaryl groups, which are aromatic ring groups having one or more nitrogen, oxygen, or sulfur atoms in the ring, such as furyl, pyrrolyl, pyridyl, and indolyl. By "substituted" is meant that one or more ring hydrogens in the aryl group is replaced with a halide such as fluorine, chlorine, or bromine; with a lower alkyl group containing one or two carbon atoms; nitro, amino, methylamino, dimethylamino, methoxy, halomethoxy, halomethyl, or haloethyl. Preferred substituents include halogen, methyl, ethyl, and methoxy. Generally preferred are aryl groups having a single ring.

"Aralkyl" refers to an alkyl, preferably lower ($C_1$-$C_4$, more preferably $C_1$-$C_2$) alkyl, substituent which is further substituted with an aryl group; examples are benzyl (—$CH_2C_6H_5$) and phenethyl (—$CH_2CH_2C_6H_5$).

"Thioalkoxy" refers to a radical of the formula —SRc where Rc is an alkyl radical as defined herein. The term "lower thioalkoxy" refers to an alkoxy group, as defined herein, containing between 1 and 8 carbons.

"Alkoxy" refers to a radical of the formula —ORda where Rd is an alkyl radical as defined herein. The term "lower alkoxy" refers to an alkoxy group, as defined herein, containing between 1 and 8 carbons. Examples of alkoxy groups include, without limitation, methoxy and ethoxy.

"Alkoxyalkyl" refers to an alkyl group substituted with an alkoxy group.

"Carbonyl" refers to the —C(=O)— radical.

"Guanidynyl" refers to the $H_2N(C=NH_2)$—NH— radical.

"Amidinyl" refers to the $H_2N(C=NH_2)CH$— radical.

"Amino" refers to the —$NH_2$ radical.

"Alkylamino" refers to a radical of the formula —NHRd or —NRdRd where each Rd is, independently, an alkyl radical as defined herein. The term "lower alkylamino" refers to an alkylamino group, as defined herein, containing between 1 and 8 carbons.

"Heterocycle" means a 5- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Preferably, the ring atoms include 3 to 6 carbon atoms. Such heterocycles include, for example, pyrrolidine, piperidine, piperazine, and morpholine.

Heterocycles include heteroaryls as defined below. Thus, in addition to the heteroaryls listed below, heterocycles also include morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydrothiophenyl, tetrahydrothiopyranyl, tetrahydropyrimidinyl, tetrahydrothiopyranyl, and the like.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, and quinazolinyl.

The term "substituted", with respect to an alkyl, alkenyl, alkynyl, aryl, aralkyl, or alkaryl group, refers to replacement of a hydrogen atom with a heteroatom-containing substituent, such as, for example, halogen, hydroxy, alkoxy, thiol, alkylthio, amino, alkylamino, imino, oxo (keto), nitro, cyano, or various acids or esters such as carboxylic, sulfonic, or phosphonic.

The term "substituted", particularly with respect to an alkyl, alkoxy, thioalkoxy, or alkylamino group, refers to replacement of a hydrogen atom on carbon with a heteroatom-containing substituent, such as, for example, halogen, hydroxy, alkoxy, thiol, alkylthio, amino, alkylamino, imino, oxo (keto), nitro, cyano, or various acids or esters such as carboxylic, sulfonic, or phosphonic. It may also refer to replacement of a hydrogen atom on a heteroatom (such as an amine hydrogen) with an alkyl, carbonyl or other carbon containing group.

In certain embodiments, the terms "optionally substituted alkyl", "optionally substituted alkenyl", "optionally substituted alkoxy", "optionally substituted thioalkoxy", "optionally substituted alkyl amino", "optionally substituted lower alkyl", "optionally substituted lower alkenyl", "optionally substituted lower alkoxy", "optionally substituted lower thioalkoxy", "optionally substituted lower alkyl amino" and "optionally substituted heterocyclyl" mean that, when substituted, at least one hydrogen atom is replaced with a substituent. In the case of an oxo substituent (=O) two hydrogen atoms are replaced. In this regard, substituents include: deuterium, optionally substituted alkyl, optionally substituted alkenyl, optionally substituted alkynyl, optionally substituted aryl, optionally substituted heterocycle, optionally substituted cycloalkyl, oxo, halogen, —CN, —ORx, NRxRy, NRxC(=O)Ry, NRxSO2Ry, —NRxC(=O)NRxRy, C(=O)Rx, C(=O)ORx, C(=O)NRxRy, —SOmRx and —SOmNRxRy, wherein m is 0, 1 or 2, Rx and Ry are the same or different and independently hydrogen, optionally substituted alkyl, optionally substituted alkenyl, optionally substituted alkynyl, optionally substituted aryl, optionally substituted heterocycle or optionally substituted cycloalkyl and each of said optionally substituted alkyl, optionally substituted alkenyl, optionally substituted alkynyl, optionally substituted aryl, optionally substituted heterocycle and optionally substituted cycloalkyl substituents may be further substituted with one or more of oxo, halogen, —CN, —ORx, NRxRy, NRxC(=O)Ry, NRxSO2Ry, —NRxC(=O) NRxRy, C(=O)Rx, C(=O)ORx, C(=O)NRxRy, —SOmRx and —SOmNRxRy.

The selection of targeting sequences capable of modulation the expression of IL-23/17 signaling pathway components is discussed below.

Targeted Genes

Embodiments of the present invention are based, in part, on the discovery that IL-17RC targeted antisense oligomers are capable of preventing death in a lethal model for hemorrhagic fever virus (HFV) infection. It is fully contemplated that similar antisense targeting strategies for other components of the IL-23/17 signaling pathway including mRNA or pre-mRNA targets for the IL-17, IL-23, IL-17RA, IL-17RC or IL-23R genes will produce similar immune modulation effects. Within the IL-17 family, IL-17A, IL-17B, IL-17C, IL-17D, IL-17E and IL-17F can be targeted. Specific embodiments target IL-17A and/or IL-17F. The pre-mRNA sequences of these target genes are known in the art. Included and described below are targets for the IL-23/17 cytokines and their receptors.

Numerous immune regulatory functions have been reported for the IL-17 family of cytokines, in part due to their ability to induce a variety of immune signaling molecules. For instance, IL-17 signaling induces proinflammatory responses, and is commonly associated with allergic responses. IL-17 signaling induces the production of a variety of cytokines, chemokines, and prostaglandins, including IL-6, G-CSF, GM-CSF, IL-1β, TGF-β, TNF-α, IL-8, GRO-α, MCP-1, and $PGE_2$, from a variety of cell types, such as fibroblasts, endothelial cells, epithelial cells, keratinocytes, and macrophages. IL-17 function is also essential to a subset of CD4+ T-cells called T helper 17 (Th17) cells. Because of these and related activities, the IL-17 family has been linked to many immune/autoimmune related diseases, including rheumatoid arthritis, asthma, lupus, allograft rejection, and anti-tumour immunity, among others described herein and known in the art.

IL-23 signaling plays a central role in the inflammatory response against infection. IL-23 signaling also promotes upregulation of the matrix metalloprotease MMP9, increases angiogenesis, reduces CD8+ T-cell infiltration, and has been implicated in the development of cancerous tumors. In conjunction with IL-6 and TGF-β1, IL-23 signaling stimulates naive CD4+ T cells to differentiate into a particular subset of cells called Th17 cells, which are distinct from the classical Th1 and Th2 cells. Th17 cells produce IL-17, a proinflammatory cytokine that enhances T cell priming and further stimulates the production of proinflammatory molecules such as IL-1, IL-6, TNF-alpha, NOS-2, and various chemokines. In these and other ways, IL-23 and IL-17 signaling pathways often work together to modulate a variety of inflammatory responses, and because of their relationship, may also contribute to a variety of dysfunctional immune states when their signaling activities are not properly regulated.

Target Selection

In certain embodiments, the genes encoding the IL-23/17 signaling targets are the antisense or RNAi targets of the present invention. An exemplary gene that forms the basis of the experimental evidence that supports this aspect of invention is the IL-17 receptor C gene (IL-17RC). The exon structure of the murine and human IL-17RC genes is shown in FIG. 2 along with the structure of the human IL-17, IL-23, IL-17RA, IL-23R and their associated GenBank accession numbers. Experiments that support the invention were conducted in mice using antisense oligonucleotides that target the exon 12 splice donor site of the murine IL-17RC pre-mRNA (muIL-17RC-SD12; SEQ ID NO:13) and listed in Table 1 as SEQ ID NO: 13. Exemplary sequences for targeting the human IL-17RC gene are listed below as SEQ ID NOs: 2-12. The location of these targeting sequences relative to the IL-17RC exons and splice junctions is shown in FIG. 3.

In certain embodiments, the exons in the carboxy-terminal half of the receptor gene are candidates for selection as targets of the invention. The exemplary target exons shown in FIG. 2 are instructive in the selection of target sequences and the design of targeting oligomers for other IL-17, IL-23, IL-17RA, IL-17RC or IL-23R genes. Listed as SEQ ID NO: 1 in the Sequence Listing is a region of human IL-17RC pre-mRNA consisting of 70 bases of intron 9 upstream of exon 10 and extending through exons 11 and 12 and 70 bases into intron 11. This is one of several preferred target sequences for practicing the invention in humans. Many target sequences in this region of IL-17RC pre-mRNA have the potential to induce exon skipping of the adjacent exon. Exemplary targeting sequences are listed in Table 1 as SEQ ID NOs 2-12. Analogous targeting sequences for other IL-23/17 signaling genes can be identified and used by skilled artisans in practicing the invention.

In certain embodiments, antisense targeting sequences are designed to hybridize to a region of one or more of the target sequences listed in Table 1, such as an exon, an intron, an exon-intron junction, or a splice junction. Certain embodiments may target proximal intronic sequences, including those sequences that are immediately adjacent to an exon (e.g., within about 10, 20, 30, 40, or 50 nucleotides of a splice junction). Certain embodiments may target entirely exonic sequences, including those exonic sequences that are proximal to splice junction (e.g., within about 10, 20, 30, 40, or 50 nucleotides of a splice junction), as well as those towards the middle of an exon. In certain embodiments, the antisense sequences are designed to skip selected exons of a IL-23/17 signaling gene, and produce an altered (typically by deletion) mRNA that can encode a protein with altered function, a non-functional protein or the altered mRNA can be degraded through nonsense mediated decay (NMD). Exemplary targets for exon-skipping include exons that encode known functional domains such as, transmembrane domains, ligand-binding domains or signaling domains, in the case of receptors and receptor binding domains in the case of IL-23/17 signaling genes. Also contemplated is the targeting of any combination of such exons or domains.

In certain embodiments, a particular function of IL-23/17 signaling genes can be modulated by such an approach. For instance, certain embodiments include the targeting of selected exons of IL-23/17 signaling genes such as IL-17RC to alter (e.g., delete) at least a portion of a domain associated with its signaling activities and thereby modulate these activities. Certain exemplary embodiments increase or agonize the signaling activities of an IL-23/17 signaling gene such as IL-17RC. Other embodiments decrease or antagonize the signaling activities of an IL-23/17 signaling gene such as IL-17RC.

In certain embodiments, the targeting sequence is complementary to at least a portion of exon 1, 2, or 3 of human IL-17, or a proximal intronic sequence. In specific embodiments, the targeting sequence is complementary to at least a portion of exon 1, 2, or 3 of IL-17A, IL-17B, IL-17C, IL-17D, IL-17E or IL-17F. In preferred embodiments, the targeting sequence is complementary to at least a portion of exon 1, 2, or 3 of IL-17A or IL-17F. In other embodiments, the targeting sequence is complementary to at least a portion of exon 1, 2, 3, or 4 of human IL-23, or a proximal intronic sequence. In certain embodiments, the targeting sequence is complementary to at least a portion of exon 1, 2, 3, 4, 5, 6, 7, 8, 9, 10, 11, 12, or 13 of human IL-17RA, or a proximal intronic sequence.

In certain embodiments, the targeting sequence is complementary to at least a portion of exon 1, 2, 3, 4, 5, 6, 7, 8, 9, 10, 11, 12, 13, 14, 15, 16, 17, 18, or 19 of human IL-17RC, or a proximal intronic sequence. In specific embodiments, the targeting sequence is complementary to at least a portion of exon 10, 11, or 12 of human IL-17RC. In more specific embodiments, the targeting sequence is complementary to a splice junction of exon 10, 11, or 12 of human IL-17RC. Also included are antisense oligomers in which the targeting sequence is complementary to an entirely intra-exonic sequence of exon 10, 11, or 12 of human IL-17RC. In specific embodiments, an antisense oligonucleotide contains or consists of a targeting sequence selected from SEQ ID NOS:2-14. In certain embodiments, the targeting sequence is complementary to at least a portion of exon 1, 2, 3, 4, 5, 6, 7, 8, 9, 10, or 11 of IL-23R, or a proximal intronic sequence.

Selected antisense targeting sequences can be made shorter, e.g., about 10-12 bases, or longer, e.g., about 40 bases, and include a small number of mismatches, as long as the sequence is sufficiently complementary to effect translation, splicing, and/or other form of inhibition upon hybridization with the target, and forms with the target RNA, a heteroduplex having a Tm of 45° C. or greater.

In certain embodiments, the degree of complementarity between the target and antisense targeting sequence is sufficient to form a stable duplex. The region of complementarity of the antisense oligomers with the target RNA sequence may be as short as 8-11 bases, but is preferably 12-15 bases or more, e.g., 12-20 bases, or 12-25 bases, including all integers in between these ranges. An antisense oligomer of about 14-15 bases is generally long enough to have a unique complementary sequence in the target mRNA or pre-mRNA.

In certain embodiments, a minimum length of complementary bases may be required to achieve the requisite binding Tm, as discussed below.

In certain embodiments, oligomers as long as 40 bases may be suitable, where at least a minimum number of bases, e.g., 10-12 bases, are complementary to the target sequence. In general, however, facilitated or active uptake in cells is optimized at oligomer lengths less than about 30. For PMO oligomers, described further below, an optimum balance of binding stability and uptake generally occurs at lengths of 18-25 bases. Included are antisense oligomers (e.g., PNAs, LNAs, 2'-OMe, MOE) and PMO oligomers that consist of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases, in which at least about 6, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 contiguous or non-contiguous bases are complementary to a selected target sequence, such as the exemplary target sequence of SEQ ID NO:1, or variants thereof.

In certain embodiments, antisense oligomers may be 100% complementary to the IL-23/17 signaling gene target sequence, or it may include mismatches, e.g., to accommodate variants, as long as a heteroduplex formed between the oligomer and the target sequence is sufficiently stable to withstand the action of cellular nucleases and other modes of degradation which may occur in vivo. Oligomer backbones that are less susceptible to cleavage by nucleases are discussed below. Mismatches, if present, are less destabilizing toward the end regions of the hybrid duplex than in the middle. The number of mismatches allowed will depend on the length of the oligomer, the percentage of G:C base pairs in the duplex, and the position of the mismatch(es) in the duplex, according to well understood principles of duplex stability. Although such an antisense oligomer is not necessarily 100% complementary to the target sequence, it is effective to stably and specifically bind to the target sequence, such that a biological activity of the nucleic acid target, e.g., expression of IL-23/17 signaling protein(s), is modulated.

The stability of the duplex formed between an oligomer and a target sequence is a function of the binding Tm and the susceptibility of the duplex to cellular enzymatic cleavage. The Tm of an antisense compound with respect to complementary-sequence RNA may be measured by conventional methods, such as those described by Hames et al., Nucleic Acid Hybridization, IRL Press, 1985, pp. 107-108 or as described in Miyada C. G. and Wallace R. B., 1987, Oligonucleotide hybridization techniques, *Methods Enzymol.* Vol. 154 pp. 94-107. In certain embodiments, antisense oligomer may have a binding Tm, with respect to a complementary-sequence RNA, of greater than body temperature and preferably greater than 50° C. Tm's in the range 60-80° C. or greater are preferred. According to well known principles, the Tm of an oligomer compound, with respect to a complementary-based RNA hybrid, can be increased by increasing the ratio of C:G paired bases in the duplex, and/or by increasing the length (in base pairs) of the heteroduplex. At the same time, for purposes of optimizing cellular uptake, it may be advantageous to limit the size of the oligomer. For this reason, compounds that show high Tm (50° C. or greater) at a length of 25 bases or less are generally preferred over those requiring greater than 25 bases for high Tm values.

In certain embodiments, such as PMO oligomers, the antisense activity of an oligomer may be enhanced by using a mixture of uncharged and cationic phosphorodiamidate linkages, as exemplified in FIG. 1B. The total number of cationic linkages in the oligomer can vary from 1 to 10 (including all integers in between), and be interspersed throughout the oligomer. Preferably the number of charged linkages is at least 2 and no more than half the total backbone linkages, e.g., between 2, 3, 4, 5, 6, 7, or 8 positively charged linkages, and preferably each charged linkages is separated along the backbone by at least 1, 2, 3, 4, or 5 uncharged linkages. The antisense activity of various oligomers can be measured in vitro by fusing the oligomer target region to the 5' end a reporter gene (e.g., firefly luciferase) and then measuring the inhibition of translation of the fusion gene mRNA transcripts in cell free translation assays. The inhibitory properties of oligomers containing a mixture of uncharged and cationic linkages can be enhanced between, approximately, two to 100 fold in cell free translation assays.

Exemplary antisense sequences for inducing exon skipping of exons 10, 11 and 12 of the human IL-17RC pre-mRNA are shown below in Table 1. The target RNA is listed as SEQ ID NO: 1 in the Sequence Listing and the individual antisense targeting sequences are named according to the position of the first target nucleotide from the 5' end of the target RNA.

TABLE 1

Exemplary Antisense Targeting Sequences

| Name | Sequence (5' to 3') | SEQ ID NO: |
| --- | --- | --- |
| huIL-17RC.24.108 | CACCCTCCCTGAAGGGGCAGATGT | 2 |
| huIL-17RC.24.213 | AGAGGTTCTGGTGTGCGCGGGGGT | 3 |
| huIL-17RC.24.319 | TCCCCACCCGGAGCCCGCCAGCAC | 4 |
| huIL-17RC.24.371 | GTCCACAGTGACGTTCTCCCAGGA | 5 |
| huIL-17RC.24.384 | CTGCTTCACTTACGTCCACAGTGA | 6 |
| huIL-17RC.24.477 | ACTCGAGAACCTTCTGTGGAAAGA | 7 |
| huIL-17RC.24.515 | CTGAACACAGAGGTTAGGGTGGCC | 8 |
| huIL-17RC.24.532 | ATGCACCCCTTTCTGACCTGAACA | 9 |
| huIL-17RC.24.545 | CCAGCCCAGCACTATGCACCCCTT | 10 |
| huIL-17RC.17.522 | CTGAACACAGAGGTTAG | 11 |
| muIL-17RC.22 | CTGGACACAGAGGTTGG | 12 |
| huIL-17RC.22.523 | TCTGACCTGAACACAGAGGTTA | 13 |
| muIL-17RCSD12.17 | TCTGACCTGGACACAGAGGTTG | 14 |

Antisense Oligonucleotide Compounds

The antisense oligonucleotides of the present invention typically (a) have the ability to be actively taken up by mammalian cells, and (b) once taken up, form a duplex with the target RNA with a Tm greater than about 45° C. In certain embodiments, the oligomer backbone may be substantially uncharged, and, preferably, may be recognized as a substrate for active or facilitated transport across the cell membrane. The ability of the oligomer to form a stable duplex with the target RNA may also relate to other features of the oligomer backbone, including the length and degree of complementarity of the antisense oligomer with respect to the target, the ratio of G:C to A:T base matches, and the positions of any mismatched bases. The ability of the antisense oligomer to resist cellular nucleases may promote survival and ultimate delivery of the agent to the cell cytoplasm. Exemplary antisense oligomer targeting sequences of the invention using the PMO backbone chemistry are listed above in Table 1. In general, PNA and LNA chemistries utilize shorter targeting oligomers due to their relatively high target binding strength compared to PMO and 2'O-Me oligomers.

Peptide nucleic acids (PNAs) are analogs of DNA in which the backbone is structurally homomorphous with a deoxyribose backbone, consisting of N-(2-aminoethyl) glycine units to which pyrimidine or purine bases are attached. PNAs containing natural pyrimidine and purine bases hybridize to complementary oligonucleotides obeying Watson-Crick base-pairing rules, and mimic DNA in terms of base pair recognition (Egholm, Buchardt et al. 1993). The backbone of PNAs is formed by peptide bonds rather than phosphodiester bonds, making them well-suited for antisense applications (see structure below). The backbone is uncharged, resulting in PNA/DNA or PNA/RNA duplexes that exhibit greater than normal thermal stability. PNAs are not recognized by nucleases or proteases.

PNAs are produced synthetically using any technique known in the art. PNA is a DNA analog in which a polyamide backbone replaces the traditional phosphate ribose ring of DNA.

Despite a radical structural change to the natural structure, PNA is capable of sequence-specific binding in a helix form to DNA or RNA. Characteristics of PNA include a high binding affinity to complementary DNA or RNA, a destabilizing effect caused by single-base mismatch, resistance to nucleases and proteases, hybridization with DNA or RNA independent of salt concentration and triplex formation with homopurine DNA. Panagene™ has developed its proprietary Bts PNA monomers (Bts; benzothiazole-2-sulfonyl group) and proprietary oligomerisation process. The PNA oligomerisation using Bts PNA monomers is composed of repetitive cycles of deprotection, coupling and capping. Panagene's patents to this technology include U.S. Pat. No. 6,969,766, U.S. Pat. No. 7,211,668, U.S. Pat. No. 7,022,851, U.S. Pat. No. 7,125,994, U.S. Pat. No. 7,145,006 and U.S. Pat. No. 7,179,896. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497.

Oligonucleotide compounds of the present invention may also contain "locked nucleic acid" subunits (LNAs). The structures of LNAs are known in the art: for example, Wengel, et al., Chemical Communications (1998) 455; Tetrahedron (1998) 54, 3607, and Accounts of Chem. Research (1999) 32, 301); Obika, et al., Tetrahedron Letters (1997) 38, 8735; (1998) 39, 5401, and Bioorganic Medicinal Chemistry (2008) 16, 9230.

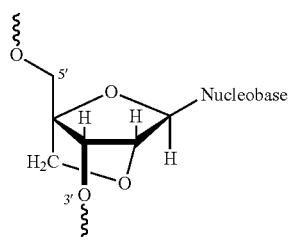

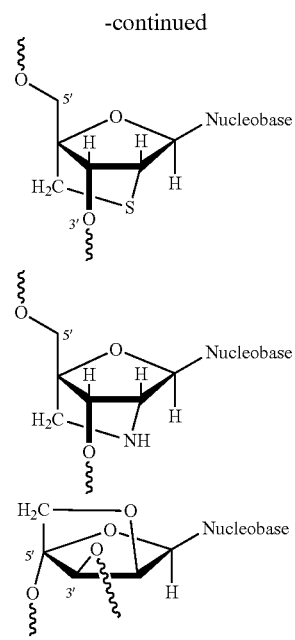

Compounds of the invention may incorporate one or more LNAs; in some cases, the compounds may be entirely composed of LNAs. Methods for the synthesis of individual LNA nucleoside subunits and their incorporation into oligonucleotides are known in the art: U.S. Pat. Nos. 7,572,582; 7,569,575; 7,084,125; 7,060,809; 7,053,207; 7,034,133; 6,794,499; and 6,670,461. Typical intersubunit linkers include phosphodiester and phosphorothioate moieties; alternatively, non-phosphorous containing linkers may be employed. A preferred embodiment is an LNA containing compound where each LNA subunit is separated by a DNA subunit (i.e., a deoxyribose nucleotide). Further preferred compounds are composed of alternating LNA and DNA subunits where the intersubunit linker is phosphorothioate.

A preferred oligomer structure employs morpholino-based subunits bearing base-pairing moieties, joined by uncharged linkages, as described above. Especially preferred is a substantially uncharged phosphorodiamidate-linked morpholino oligomer. Morpholino oligonucleotides, including antisense oligomers, are detailed, for example, in co-owned U.S. Pat. Nos. 5,698,685, 5,217,866, 5,142,047, 5,034,506, 5,166,315, 5,185,444, 5,521,063, and 5,506,337, and in PCT application No. US08/088339, all of which are expressly incorporated by reference herein.

Certain properties of the morpholino-based subunits include: the ability to be linked in a oligomeric form by stable, uncharged backbone linkages; the ability to support a nucleotide base (e.g., adenine, cytosine, guanine or uracil) such that the polymer formed can hybridize with a complementary-base target nucleic acid, including target RNA, with high Tm, even with oligomers as short as 10-14 bases; the ability of the oligomer to be actively transported into mammalian cells; and the ability of the oligomer:RNA heteroduplex to resist RNase degradation.

Figure 1A:
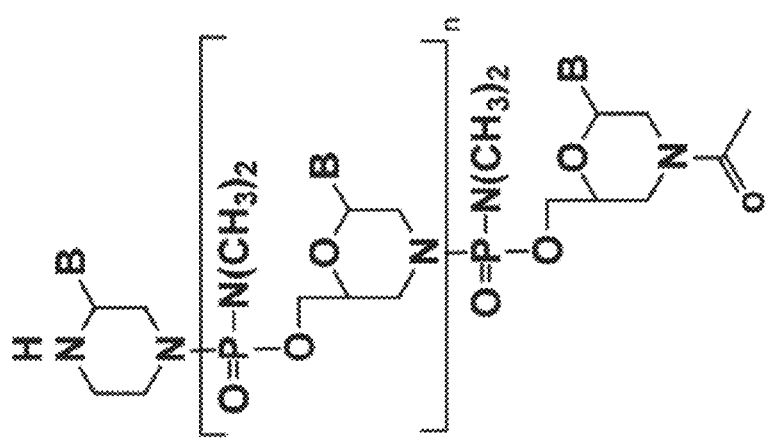
FIG. 1A shows an exemplary morpholino oligomer structure with a phosphorodiamidate linkage.
Figure 1C:
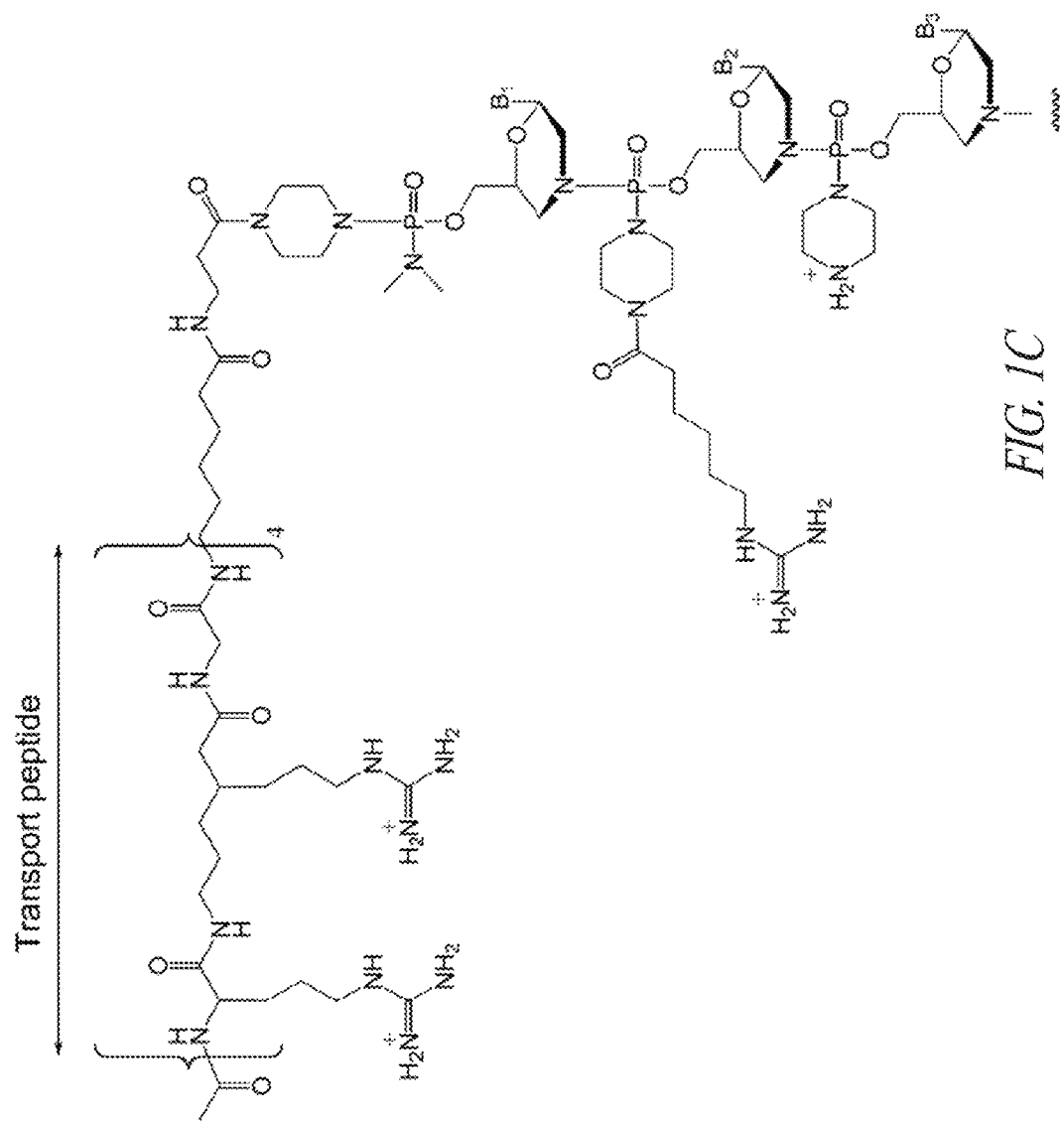
FIG. 1C shows a conjugate of an arginine-rich peptide and an antisense oligomer, in accordance with one embodiment of the invention.

Examples of morpholino oligonucleotides having phosphorus-containing backbone linkages are illustrated in FIGS. 1A-1C. Especially preferred is a phosphorodiamidate-linked morpholino oligonucleotide, as shown in FIG. 1B, which is modified, in accordance with one aspect of the present invention, to contain positively charged groups at preferably 5%-50% or 10%-50% of its backbone linkages. Morpholino oligonucleotides with uncharged backbone linkages, including antisense oligonucleotides, are detailed, for example, in (Summerton and Weller 1997) and in co-owned U.S. Pat. Nos. 5,698,685, 5,217,866, 5,142,047, 5,034,506, 5,166,315, 5,185, 444, 5,521,063, and 5,506,337, and in PCT application No. US08/012804, all of which are expressly incorporated by reference herein.

Properties of the morpholino-based subunits include: 1) the ability to be linked in a oligomeric form by stable, uncharged or positively charged backbone linkages; 2) the ability to support a nucleotide base (e.g., adenine, cytosine, guanine, thymidine, uracil and hypoxanthine) such that the polymer formed can hybridize with a complementary-base target nucleic acid, including target RNA, Tm values above about 45° C. in relatively short oligonucleotides (e.g., 10-15 bases); 3) the ability of the oligonucleotide to be actively or passively transported into mammalian cells; and 4) the ability of the antisense oligonucleotide:RNA heteroduplex to resist RNase and RNaseH degradation, respectively.

Figure 1D:
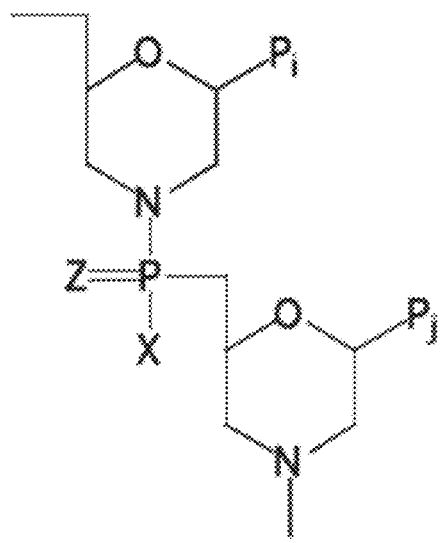
Figure 1E:
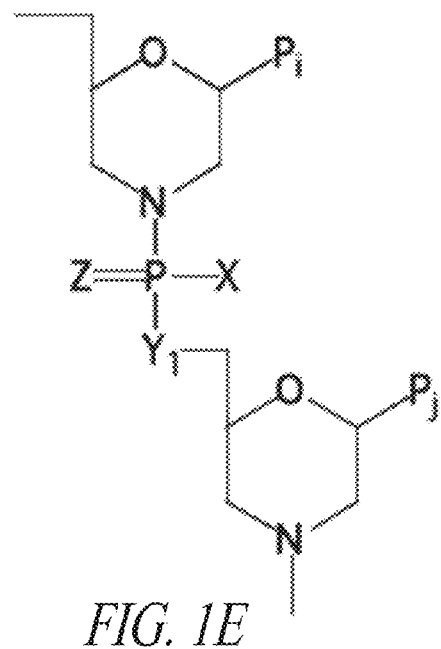

Exemplary backbone structures for antisense oligonucleotides of the claimed subject matter include the morpholino subunit types shown in FIGS. 1D-1G, each linked by an uncharged or positively charged, phosphorus-containing subunit linkage. FIG. 1D shows a phosphorus-containing linkage which forms the five atom repeating-unit backbone, where the morpholino rings are linked by a 1-atom phosphoamide linkage. FIG. 1E shows a linkage which produces a 6-atom repeating-unit backbone. In this structure, the atom Y linking the 5' morpholino carbon to the phosphorus group may be sulfur, nitrogen, carbon or, preferably, oxygen. The X moiety pendant from the phosphorus may be fluorine, an alkyl or substituted alkyl, an alkoxy or substituted alkoxy, a thioalkoxy or substituted thioalkoxy, or unsubstituted, monosubstituted, or disubstituted nitrogen, including cyclic structures, such as morpholines or piperidines. Alkyl, alkoxy and thioalkoxy preferably include 1-6 carbon atoms. The Z moieties are sulfur or oxygen, and are preferably oxygen.

Figure 1F:
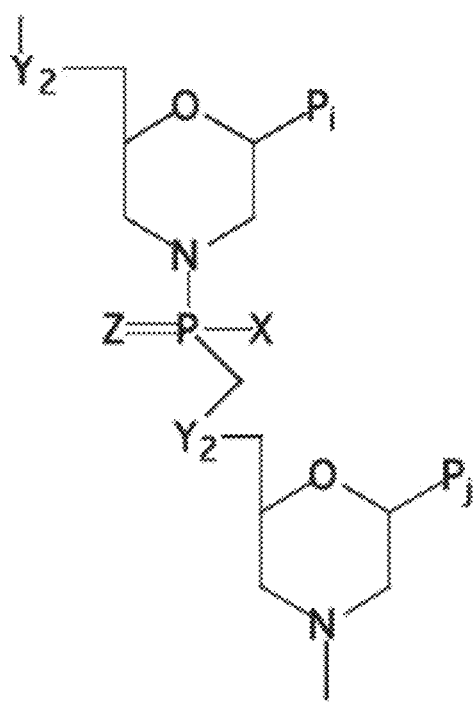
Figure 1G:
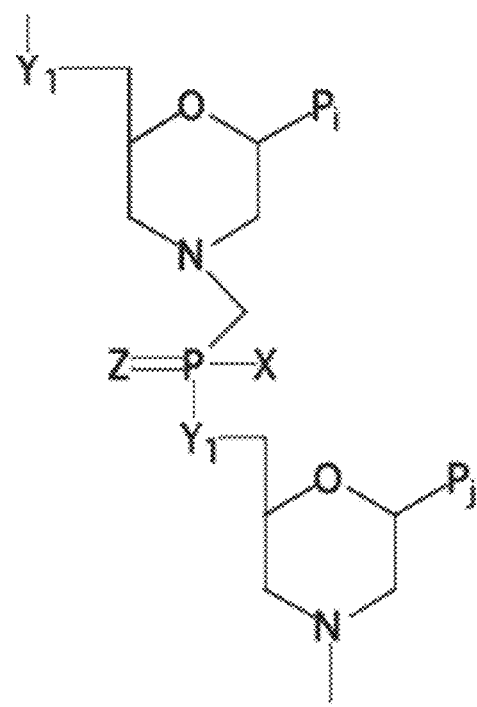

The linkages shown in FIGS. 1F and 1G are designed for 7-atom unit-length backbones. In structure 1F, the X moiety is as in Structure 1E, and the Y moiety may be methylene, sulfur, or, preferably, oxygen. In Structure 1 G, the X and Y moieties are as in Structure 1E. Particularly preferred morpholino oligonucleotides include those composed of morpholino subunit structures of the form shown in FIG. 1E, where X=NH$_2$, N(CH$_3$)$_2$, or 1-piperazine or other charged group, Y=O, and Z=O.

As noted above, the substantially uncharged oligonucleotide may be modified, in accordance with an aspect of the invention, to include charged linkages, e.g., up to about 1 per every 2-20 uncharged linkages, and more preferably as about 1-3 per every 10 uncharged linkages. In certain embodiments, optimal improvement in antisense activity may be seen when about 20% of the backbone linkages are cationic. In certain embodiments, enhancement may be seen with a small number e.g., 10-20% cationic linkages, or where the number of cationic linkages are in the range 50-80%, such as about 60%.

The enhancement seen with added cationic backbone charges may, in some cases, be further enhanced by distributing the bulk of the charges close to the "center-region" of the backbone linkages of the antisense oligonucleotide, e.g., in a 20-mer oligonucleotide with 8 cationic backbone linkages, having at least 70% of these charged linkages localized in the 10 centermost linkages.

In certain embodiments, the antisense compounds can be prepared by stepwise solid-phase synthesis, employing methods detailed in the references cited above, and below with respect to the synthesis of oligonucleotides having a mixture or uncharged and cationic backbone linkages. In some cases, it may be desirable to add additional chemical moieties to the antisense compound, e.g., to enhance pharmacokinetics or to facilitate capture or detection of the compound. Such a moiety may be covalently attached, typically to a terminus of the oligomer, according to standard synthetic methods. For example, addition of a polyethyleneglycol moiety or other hydrophilic polymer, e.g., one having 10-100 monomeric subunits, may be useful in enhancing solubility. One or more charged groups, e.g., anionic charged groups such as an organic acid, may enhance cell uptake.

A reporter moiety, such as fluorescein or a radiolabeled group, may be attached for purposes of detection. Alternatively, the reporter label attached to the oligomer may be a ligand, such as an antigen or biotin, capable of binding a labeled antibody or streptavidin. In selecting a moiety for attachment or modification of an antisense compound, it is generally of course desirable to select chemical compounds of groups that are biocompatible and likely to be tolerated by a subject without undesirable side effects.

As noted above, certain of the antisense compounds can be constructed to contain a selected number of cationic linkages interspersed with uncharged linkages of the type described above. The intersubunit linkages, both uncharged and cationic, preferably are phosphorus-containing linkages, having the structure:

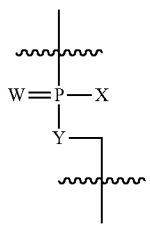

where
W is S or O, and is preferably O,
$X=NR^1R^2$ or $OR^6$,
$Y=O$ or $NR^7$,
and each said linkage in the oligomer is selected from:
(a) uncharged linkage (a), where each of $R^1$, $R^2$, $R^6$ and $R^7$ is independently selected from hydrogen and lower alkyl;
(b1) cationic linkage (b1), where $X=NR^1R^2$ and $Y=O$, and $NR^1R^2$ represents an optionally substituted piperazino group, such that $R^1R^2=$—CHRCHRN($R^3$)($R^4$)CHRCHR—, where
each R is independently H or $CH_3$,
$R^4$ is H, $CH_3$, or an electron pair, and
$R^3$ is selected from H, lower alkyl, e.g., $CH_3$, C(═NH)$NH_2$, Z-L-NHC(═NH)$NH_2$, and [C(O)CHR'NH]$_m$H, where: Z is C(O) or a direct bond, L is an optional linker up to 18 atoms in length, preferably up to 12 atoms, and more preferably up to 8 atoms in length, having bonds selected from alkyl, alkoxy, and alkylamino, R' is a side chain of a naturally occurring amino acid or a one- or two-carbon homolog thereof, and m is 1 to 6, preferably 1 to 4;
(b2) cationic linkage (b2), where $X=NR^1R^2$ and $Y=O$, $R^1=H$ or $CH_3$, and $R^2=LNR^3R^4R^5$, where L, $R^3$, and $R^4$ are as defined above, and $R^5$ is H, lower alkyl, or lower (alkoxy) alkyl; and
(b3) cationic linkage (b3), where $Y=NR^7$ and $X=OR^6$, and $R^7=LNR^3R^4R^5$, where L, $R^3$, $R^4$ and $R^5$ are as defined above, and $R^6$ is H or lower alkyl;
and at least one said linkage is selected from cationic linkages (b1), (b2), and (b3).

In certain embodiments, an oligomer may include at least two consecutive linkages of type (a) (i.e. uncharged linkages). In further embodiments, at least 5% of the linkages in the oligomer are cationic linkages (i.e. type (b1), (b2), or (b3)); for example, 10% to 60%, and preferably 20-50% linkages may be cationic linkages.

In one embodiment, at least one linkage is of type (b1), where, preferably, each R is H, $R^4$ is H, $CH_3$, or an electron pair, and $R^3$ is selected from H, lower alkyl, e.g., $CH_3$, C(═NH)$NH_2$, and C(O)-L-NHC(═NH)$NH_2$. The latter two embodiments of $R^3$ provide a guanidino moiety, either attached directly to the piperazine ring, or pendant to a linker group L, respectively. For ease of synthesis, the variable Z in $R^3$ is preferably C(O) (carbonyl), as shown.

The linker group L, as noted above, contains bonds in its backbone selected from alkyl (e.g., —$CH_2$—$CH_2$—), alkoxy (—C—O—), and alkylamino (e.g., —$CH_2$—NH—), with the proviso that the terminal atoms in L (e.g., those adjacent to carbonyl or nitrogen) are carbon atoms. Although branched linkages (e.g., —$CH_2$—$CHCH_3$—) are possible, the linker is preferably unbranched. In one embodiment, the linker is a hydrocarbon linker Such a linker may have the structure —$(CH_2)_n$—, where n is 1-12, preferably 2-8, and more preferably 2-6.

The morpholino subunits have the structure:

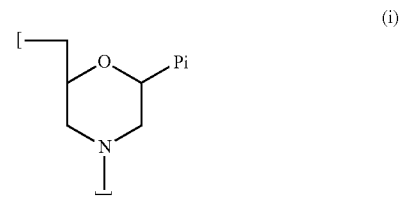

where Pi is a base-pairing moiety, and the linkages depicted above connect the nitrogen atom of (i) to the 5' carbon of an adjacent subunit. The base-pairing moieties Pi may be the same or different, and are generally designed to provide a sequence which binds to a target nucleic acid.

The use of embodiments of linkage types (b1), (b2) and (b3) above to link morpholino subunits may be illustrated graphically as follows:

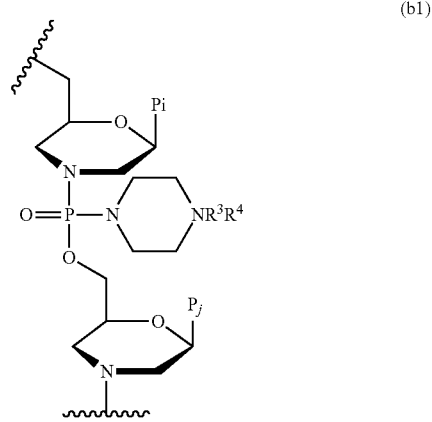

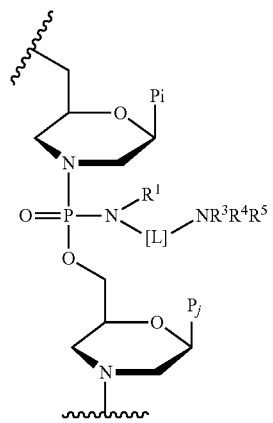

(b2)

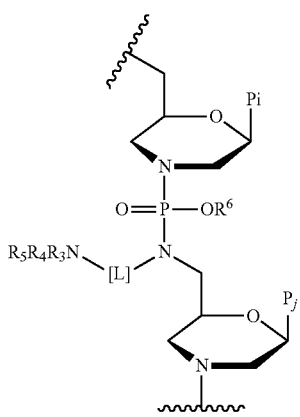

(b3)

Preferably, all cationic linkages in the oligomer are of the same type; i.e. all of type (b1), all of type (b2), or all of type (b3).

In further embodiments, the cationic linkages are selected from linkages (b1') and (b1") as shown below, where (b1") is referred to herein as a "Pip" linkage and (b1") is referred to herein as a "GuX" linkage:

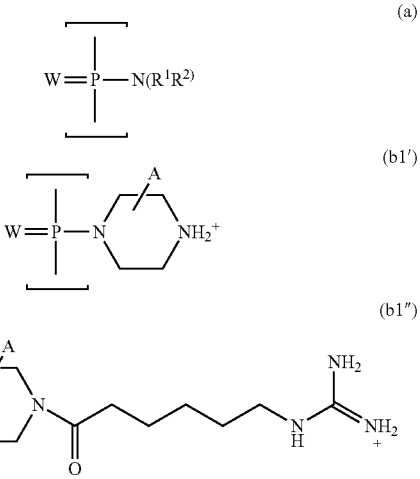

In the structures above, W is S or O, and is preferably O; each of $R^1$ and $R^2$ is independently selected from hydrogen and lower alkyl, and is preferably methyl; and A represents hydrogen or a non-interfering substituent on one or more carbon atoms in (b1') and (b1"). Preferably, the ring carbons in the piperazine ring are unsubstituted; however, they may include non-interfering substituents, such as methyl or fluorine. Preferably, at most one or two carbon atoms is so substituted. In further embodiments, at least 10% of the linkages are of type (b1') or (b1"); for example, 10%-60% and preferably 20% to 50%, of the linkages may be of type (b1') or (b1").

In certain embodiments, the oligomer contains no linkages of the type (b1') above. Alternatively, the oligomer contains no linkages of type (b1) where each R is H, $R^3$ is H or $CH_3$, and $R^4$ is H, $CH_3$, or an electron pair.

The morpholino subunits may also be linked by non-phosphorus-based intersubunit linkages, as described further below, where at least one linkage is modified with a pendant cationic group as described above.

Other oligonucleotide analog linkages which are uncharged in their unmodified state but which could also bear a pendant amine substituent could be used. For example, a 5'nitrogen atom on a morpholino ring could be employed in a sulfamide linkage or a urea linkage (where phosphorus is replaced with carbon or sulfur, respectively) and modified in a manner analogous to the 5'-nitrogen atom in structure (b3) above.

Oligomers having any number of cationic linkages are provided, including fully cationic-linked oligomers. Preferably, however, the oligomers are partially charged, having, for example, 10%-80%. In preferred embodiments, about 10% to 60%, and preferably 20% to 50% of the linkages are cationic.

In one embodiment, the cationic linkages are interspersed along the backbone. The partially charged oligomers preferably contain at least two consecutive uncharged linkages; that is, the oligomer preferably does not have a strictly alternating pattern along its entire length.

Also considered are oligomers having blocks of cationic linkages and blocks of uncharged linkages; for example, a central block of uncharged linkages may be flanked by blocks of cationic linkages, or vice versa. In one embodiment, the oligomer has approximately equal-length 5',3' and center regions, and the percentage of cationic linkages in the center region is greater than about 50%, preferably greater than about 70%.

Oligomers for use in antisense applications generally range in length from about 10 to about 40 subunits, more preferably about 10 to 30 subunits, and typically 15-25 bases. For example, an oligomer of the invention having 19-20 subunits, a useful length for an antisense compound, may ideally have two to ten, e.g., four to eight, cationic linkages, and the remainder uncharged linkages. An oligomer having 14-15 subunits may ideally have two to seven, e.g., 3, 4, or 5, cationic linkages and the remainder uncharged linkages.

Each morpholino ring structure supports a base pairing moiety, to form a sequence of base pairing moieties which is typically designed to hybridize to a selected antisense target in a cell or in a subject being treated. The base pairing moiety may be a purine or pyrimidine found in native DNA or RNA (e.g., A, G, C, T or U) or an analog, such as hypoxanthine (the base component of the nucleoside inosine) or 5-methyl cytosine.

Peptide Transporters

In certain embodiments, the antisense compounds of the invention may include an oligonucleotide moiety conjugated to an arginine-rich peptide transport moiety effective to enhance transport of the compound into cells. The transport moiety may be attached to a terminus of the oligomer, as shown, for example, in FIG. 1C. The peptide transport moiety preferably comprises 6 to 16 subunits selected from X' subunits, Y' subunits, and Z' subunits, where (a) each X' subunit independently represents lysine, arginine or an arginine analog, said analog being a cationic α-amino acid comprising a side chain of the structure $R^1N=C(NH_2)R^2$, where $R^1$ is H or R; $R^2$ is R, $NH_2$, NHR, or $NR_2$, where R is lower alkyl or lower alkenyl and may further include oxygen or nitrogen; $R^1$ and $R^2$ may together form a ring; and the side chain is linked to said amino acid via $R^1$ or $R^2$;

(b) each Y' subunit independently represents a neutral amino acid —C(O)—(CHR)$_n$—NH—, where n is 2 to 7 and each R is independently H or methyl; and (c) each Z' subunit independently represents an α-amino acid having a neutral aralkyl side chain;

wherein the peptide comprises a sequence represented by one of (X'Y'X')$_p$, (X'Y')$_m$, and (X'Z'Z')$_p$, where p is 2 to 5 and m is 2 to 8. Certain embodiments include various combinations selected independently from (X'Y'X')$_p$, (X'Y')$_m$, and/or (X'Z'Z')$_p$, including, for example, peptides having the sequence (X'Y'X')(X'Z'Z')(X'Y'X')(X'Z'Z') (SEQ ID NO:33).

In selected embodiments, for each X', the side chain moiety is guanidyl, as in the amino acid subunit arginine (Arg). In further embodiments, each Y' is —CO—(CH$_2$)$_n$-CHR—NH—, where n is 2 to 7 and R is H. For example, when n is 5 and R is H, Y' is a 6-aminohexanoic acid subunit, abbreviated herein as Ahx; when n is 2 and R is H, Y' is a β-alanine subunit, abbreviated herein as B. Certain embodiments relate to carrier peptides having a combination of different neutral amino acids, including, for example, peptides comprising the sequence -RAhxRRBRRAhxRRBRAhxB- (SEQ ID NO:23), which contains both β-alanine and 6-aminohexanoic acid.

Preferred peptides of this type include those comprising arginine dimers alternating with single Y' subunits, where Y' is preferably Ahx or Glycine. Examples include peptides having the formula (RY'R)$_p$ or the formula (RRY')$_p$, where Y' is preferably Ahx. In one embodiment, Y' is a 6-aminohexanoic acid subunit, R is arginine and p is 4.

Certain embodiments include various linear combinations of at least two of (RY'R)$_p$ and (RRY')$_p$, including, for example, illustrative peptides having the sequence (RY'R)(RRY')(RY'R)(RRY') (SEQ ID NO:34), or (RRY')(RY'R)(RRY') (SEQ ID NO:35). Other combinations are contemplated. In a further illustrative embodiment, each Z' is phenylalanine, and m is 3 or 4.

Exemplary delivery peptides also include poly arginine (R$_n$) where n can range from 6 to 9 (see SEQ ID NOs: 16, 24-26). Additional peptides include the Tat peptide or reverse Tat (rTat) as shown below in Table 2 (see SEQ ID NOs: 15, 29 & 30)

The conjugated peptide is preferably linked to a terminus of the oligomer via a linker Ahx-B, where Ahx is a 6-aminohexanoic acid subunit and B is a β-alanine subunit, as shown, for example, in FIG. 1C. Another exemplary linker is Glycine.

In selected embodiments, for each X', the side chain moiety is independently selected from the group consisting of guanidyl (HN=C(NH$_2$)NH—), amidinyl (HN=C(NH$_2$)C<), 2-aminodihydropyrimidyl, 2-aminotetrahydropyrimidyl, 2-aminopyridinyl, and 2-aminopyrimidonyl, and it is preferably selected from guanidyl and amidinyl. In one embodiment, the side chain moiety is guanidyl, as in the amino acid subunit arginine (Arg).

In certain embodiments, the Y' subunits may be either contiguous, in that no X' subunits intervene between Y' subunits, or interspersed singly between X' subunits. In certain embodiments, the linking subunit may be between Y' subunits. In one embodiment, the Y' subunits are at a terminus of the transporter; in other embodiments, they are flanked by X' subunits. In further preferred embodiments, each Y' is —CO—(CH$_2$)$_n$CHR—NH—, where n is 2 to 7 and R is H. For example, when n is 5 and R is H, Y' is a 6-aminohexanoic acid subunit, abbreviated herein as Ahx.

In selected embodiments of this group, each X' comprises a guanidyl side chain moiety, as in an arginine subunit. Preferred peptides of this type include those comprising arginine dimers alternating with single Y' subunits, where Y' is preferably Ahx. Examples include peptides having the formula (RY'R)$_4$ or the formula (RRY')$_4$, where Y' is preferably Ahx. In the latter case, the nucleic acid analog is preferably linked to a terminal Y' subunit, preferably at the C-terminus, as shown, for example, in FIG. 1C. The preferred linker is of the structure AhxB or Glycine, where Ahx is a 6-aminohexanoic acid subunit and B is a β-alanine subunit.

The transport moieties as described herein have been shown to greatly enhance cell entry of attached oligomers, relative to uptake of the oligomer in the absence of the attached transport moiety, and relative to uptake by an attached transport moiety lacking the hydrophobic subunits Y'. Such enhanced uptake is preferably evidenced by at least a two-fold increase, and preferably a four-fold increase, in the uptake of the compound into mammalian cells relative to uptake of the agent by an attached transport moiety lacking the hydrophobic subunits Y'. Uptake is preferably enhanced at least twenty fold, and more preferably forty fold, relative to the unconjugated compound.

A further benefit of the transport moiety is its expected ability to stabilize a duplex between an antisense compound and its target nucleic acid sequence, presumably by virtue of electrostatic interaction between the positively charged transport moiety and the negatively charged nucleic acid. The number of charged subunits in the transporter is less than 14, as noted above, and preferably between 8 and 11.

The use of arginine-rich peptide transporters (i.e., cell-penetrating peptides) are particularly useful in practicing certain embodiments of the present invention. Certain peptide transporters have been shown to be highly effective at delivery of antisense compounds into primary cells including hematopoietic and muscle cells (Marshall, Oda et al. 2007; Jearawiriyapaisarn, Moulton et al. 2008; Wu, Moulton et al. 2008). Furthermore, compared to other known peptide transporters such as Penetratin and the Tat peptide, the peptide transporters described herein, when conjugated to an antisense PMO, demonstrate an enhanced ability to alter splicing of several gene transcripts (Marshall, Oda et al. 2007). Exemplary peptide transporters, including linkers (B or AhxB) are shown in Table 2 below (X residues refer to 6-aminohexanoic acid).

TABLE 2

Exemplary Peptide Transporters

| Peptide | Sequence (N-terminal to C-terminal) | SEQ ID NO: |
|---|---|---|
| rTat | RRRQRRKKRC | 15 |
| R$_9$F$_2$ | RRRRRRRRRFFC | 16 |
| (RRAhx)$_4$B | RRAhxRRAhxRRAhxRRAhxB | 17 |
| (RAhxR)$_4$AhxB; (P007) | RAhxRRAhxRRAhxRRAhxRAhxB | 18 |

TABLE 2-continued

Exemplary Peptide Transporters

| Peptide | Sequence (N-terminal to C-terminal) | SEQ ID NO: |
|---|---|---|
| (AhxRR)$_4$AhxB | AhxRRAhxRRAhxRRAhxRRAhxB | 19 |
| (RAhx)$_6$B | RAhxRAhxRAhxRAhxRAhxRAhxB | 20 |
| (RAhx)$_8$B | RAhxRAhxRAhxRAhxRAhxRAhxRAhxRAhxB | 21 |
| (RAhxR)$_5$AhxB (CP04057) | RAhxRRAhxRRAhxRRAhxRRAhxRRAhxB | 22 |
| (RAhxRRBR)$_2$AhxB; (CP06062) | RAhxRRBRRAhxRRBRAhxB | 23 |
| R$_6$G | RRRRRRG | 24 |
| R$_7$G | RRRRRRRG | 25 |
| R$_8$G | RRRRRRRRG | 26 |
| R$_5$GR$_4$G | RRRRRGRRRRG | 27 |
| R$_5$F$_2$R$_4$G | RRRRRFFRRRRG | 28 |
| Tat-G | RKKRRQRRRG | 29 |
| rTat-G | RRRQRRKKRG | 30 |
| (RXR$_2$G$_2$)$_2$ | RXRRGGRXRRGG | 31 |
| (RXR$_3$X)$_2$G | RXRRRXRXRRRXG | 32 |

RNA Interference Agents

The IL-23/17 signaling gene target regions described herein may also be targeted by a variety of RNA interference-based methods. RNA interference (RNAi) is an evolutionarily conserved gene-silencing mechanism, originally discovered in studies of the nematode *Caenorhabditis elegans* (Lee et al, Cell 75:843,1993; Reinhart et al., Nature 403:901, 2000). It may be triggered by introducing dsRNA into cells expressing the appropriate molecular machinery, which then degrades the corresponding endogenous mRNA. The mechanism involves conversion of dsRNA into short RNAs that direct ribonucleases to homologous mRNA targets (summarized, Ruvkun, Science 2294:797, 2001).

In certain embodiments, the methods provided herein may utilize double-stranded ribonucleic acid (dsRNA) molecules as IL-23/17 signaling gene modulating agents. dsRNAs generally comprise two single strands. One strand of the dsRNA comprises a nucleotide sequence that is substantially identical to a portion of the target gene or target region (the "sense" strand), and the other strand (the "complementary" or "antisense" strand) comprises a sequence that is substantially complementary to a portion of the target region. The strands are sufficiently complementary to hybridize to form a duplex structure. In certain embodiments, the complementary RNA strand may be less than 30 nucleotides, less than 25 nucleotides in length, or even 19 to 24 nucleotides in length. In certain aspects, the complementary nucleotide sequence may be 20-23 nucleotides in length, or 22 nucleotides in length.

In certain embodiments, at least one of the RNA strands comprises a nucleotide overhang of 1 to 4 nucleotides in length. In other embodiments, the dsRNA may further comprise at least one chemically modified nucleotide. In certain aspects, a dsRNA comprising a single-stranded overhang of 1 to 4 nucleotides may comprise a molecule wherein the unpaired nucleotide of the single-stranded overhang that is directly adjacent to the terminal nucleotide pair contains a purine base. In other aspects, the last complementary nucleotide pairs on both ends of a dsRNA are a G-C pair, or, at least two of the last four terminal nucleotide pairs are G-C pairs.

Certain embodiments of the present invention may comprise microRNAs. Micro-RNAs represent a large group of small RNAs produced naturally in organisms, some of which regulate the expression of target genes. Micro-RNAs are formed from an approximately 70 nucleotide single-stranded hairpin precursor transcript by Dicer. (V. Ambros et al. Current Biology 13:807, 2003). Micro-RNAs are not translated into proteins, but instead bind to specific messenger RNAs, thereby blocking translation. It is thought that micro-RNAs base-pair imprecisely with their targets to inhibit translation. Certain micro-RNAs may be transcribed as hairpin RNA precursors, which are then processed to their mature forms by Dicer enzyme.

In certain embodiments, the modulating agent, or RNAi oligonucleotide, is single stranded. In other embodiments, the modulating agent, or RNAi oligonucleotide, is double stranded. Certain embodiments may also employ short-interfering RNAs (siRNA). In certain embodiments, the first strand of the double-stranded oligonucleotide contains two more nucleoside residues than the second strand. In other embodiments, the first strand and the second strand have the same number of nucleosides; however, the first and second strands are offset such that the two terminal nucleosides on the first and second strands are not paired with a residue on the complimentary strand. In certain instances, the two nucleosides that are not paired are thymidine resides.

In instances when the modulating agent comprises siRNA, the agent should include a region of sufficient homology to the target region, and be of sufficient length in terms of nucleotides, such that the siRNA agent, or a fragment thereof, can mediate down regulation of the target RNA. It will be understood that the term "ribonucleotide" or "nucleotide" can, in the case of a modified RNA or nucleotide surrogate, also refer to a modified nucleotide, or surrogate replacement moiety at one or more positions. Thus, an siRNA agent is or includes a region which is at least partially complementary to the target RNA. It is not necessary that there be perfect complementarity between the siRNA agent and the target, but the correspondence must be sufficient to enable the siRNA agent, or a cleavage product thereof, to direct sequence specific silencing, such as by RNAi cleavage of the target RNA. Complementarity, or degree of homology with the target strand, is most critical in the antisense strand. While perfect complementarity, particularly in the antisense strand, is often desired some embodiments include one or more but preferably 10, 8, 6, 5, 4, 3, 2, or fewer mismatches with respect to the target RNA. The mismatches are most tolerated in the terminal regions, and if present are preferably in a terminal region or regions, e.g., within 6, 5, 4, or 3 nucleotides of the 5' and/or 3' terminus. The sense strand need only be sufficiently complementary with the antisense strand to maintain the over all double-strand character of the molecule.

In addition, an siRNA modulating agent may be modified or include nucleoside surrogates. Single stranded regions of an siRNA agent may be modified or include nucleoside surrogates, e.g., the unpaired region or regions of a hairpin structure, e.g., a region which links two complementary regions, can have modifications or nucleoside surrogates. Modification to stabilize one or more 3'- or 5'-terminus of an siRNA agent, e.g., against exonucleases, or to favor the antisense siRNA agent to enter into RISC are also useful. Modifications can include C3 (or C6, C7, C12) amino linkers, thiol linkers, carboxyl linkers, non-nucleotidic spacers (C3, C6, C9, C12, abasic, triethylene glycol, hexaethylene glycol), special biotin or fluorescein reagents that come as phosphoramidites and that have another DMT-protected hydroxyl group, allowing multiple couplings during RNA synthesis.

siRNA agents may include, for example, molecules that are long enough to trigger the interferon response (which can be cleaved by Dicer (Bernstein et al. 2001. Nature, 409:363-366) and enter a RISC (RNAi-induced silencing complex)), in addition to molecules which are sufficiently short that they do not trigger the interferon response (which molecules can also be cleaved by Dicer and/or enter a RISC), e.g., molecules which are of a size which allows entry into a RISC, e.g., molecules which resemble Dicer-cleavage products. Molecules that are short enough that they do not trigger an interferon response are termed siRNA agents or shorter RNAi agents herein. "siRNA agent or shorter RNAi agent" as used refers to an siRNA agent that is sufficiently short that it does not induce a deleterious interferon response in a human cell, e.g., it has a duplexed region of less than 60 but preferably less than 50, 40, or 30 nucleotide pairs. An siRNA modulating agent, or a cleavage product thereof, can down regulate a target gene, e.g., by inducing RNAi with respect to a target RNA.

Each strand of an siRNA modulating agent can be equal to or less than 35, 30, 25, 24, 23, 22, 21, or 20 nucleotides in length. The strand is preferably at least 19 nucleotides in length. For example, each strand can be between 21 and 25 nucleotides in length. Preferred siRNA agents have a duplex region of 17, 18, 19, 29, 21, 22, 23, 24, or 25 nucleotide pairs, and one or more overhangs, preferably one or two 3' overhangs, of 2-3 nucleotides.

In addition to homology to target RNA and the ability to down regulate a target gene, an siRNA modulating agent may have one or more of the following properties: it may, despite modifications, even to a very large number, or all of the nucleosides, have an antisense strand that can present bases (or modified bases) in the proper three dimensional framework so as to be able to form correct base pairing and form a duplex structure with a homologous target RNA which is sufficient to allow down regulation of the target, e.g., by cleavage of the target RNA; it may, despite modifications, even to a very large number, or all of the nucleosides, still have "RNA-like" properties, i.e., it may possess the overall structural, chemical and physical properties of an RNA molecule, even though not exclusively, or even partly, of ribonucleotide-based content. For example, an siRNA agent can contain, e.g., a sense and/or an antisense strand in which all of the nucleotide sugars contain e.g., 2' fluoro in place of 2' hydroxyl. This deoxyribonucleotide-containing agent can still be expected to exhibit RNA-like properties. While not wishing to be bound by theory, the electronegative fluorine prefers an axial orientation when attached to the C2' position of ribose. This spatial preference of fluorine can, in turn, force the sugars to adopt a $C_3$'-endo pucker. This is the same puckering mode as observed in RNA molecules and gives rise to the RNA-characteristic A-family-type helix. Further, since fluorine is a good hydrogen bond acceptor, it can participate in the same hydrogen bonding interactions with water molecules that are known to stabilize RNA structures. Generally, it is preferred that a modified moiety at the 2' sugar position will be able to enter into H-bonding which is more characteristic of the OH moiety of a ribonucleotide than the H moiety of a deoxyribonucleotide.

A "single strand RNAi agent" as used herein, is an RNAi agent which is made up of a single molecule. It may include a duplexed region, formed by intra-strand pairing, e.g., it may be, or include, a hairpin or pan-handle structure. Single strand RNAi modulating agents are preferably antisense with regard to the target molecule. A single strand RNAi agent should be sufficiently long that it can enter the RISC and participate in RISC mediated cleavage of a target mRNA. A single strand RNAi agent is at least 14, and more preferably at least 15, 20, 25, 29, 35, 40, or 50 nucleotides in length. It is preferably less than 200, 100, or 60 nucleotides in length.

Hairpin RNAi modulating agents may have a duplex region equal to or at least 17, 18, 19, 29, 21, 22, 23, 24, or 25 nucleotide pairs. The duplex region may preferably be equal to or less than 200, 100, or 50, in length. Certain ranges for the duplex region are 15-30, 17 to 23, 19 to 23, and 19 to 21 nucleotides pairs in length. The hairpin may have a single strand overhang or terminal unpaired region, preferably the 3', and preferably of the antisense side of the hairpin. In certain embodiments, overhangs are 2-3 nucleotides in length.

Certain modulating agents utilized according to the methods provided herein may comprise RNAi oligonucleotides such as chimeric oligonucleotides, or "chimeras," which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. Consequently, comparable results can often be obtained with shorter oligonucleotides when chimeric oligonucleotides are used, compared to phosphorothioate oligodeoxynucleotides. Chimeric oligonucleotides may be formed as composite structures of two or more oligonucleotides, modified oligonucleotides, oligonucleotides and/or oligonucleotide mimetics as described above. Such oligonucleotides have also been referred to in the art as hybrids or gapmers. Representative U.S. patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; 5,700,922; and 5,955,589, each of which is herein incorporated by reference. In certain embodiments, the chimeric oligonucleotide is RNA-DNA, DNA-RNA, RNA-DNA-RNA, DNA-RNA-DNA, or RNA-DNA-RNA-DNA, wherein the oligonucleotide is between 5 and 60 nucleotides in length.

In one aspect of the invention, modulating agents, such as RNAi agents, relate to an oligonucleotide comprising at least one ligand tethered to an altered or non-natural nucleobase. A large number of compounds can function as the altered base. The structure of the altered base is important to the extent that the altered base should not substantially prevent binding of the oligonucleotide to its target, e.g., mRNA. In certain embodiments, the altered base is difluorotolyl, nitropyrrolyl, nitroimidazolyl, nitroindolyl, napthalenyl, anthrancenyl, pyridinyl, quinolinyl, pyrenyl, or the divalent radical of any one of the non-natural nucleobases described herein. In certain embodiments, the non-natural nucleobase is difluorotolyl, nitropyrrolyl, or nitroimidazolyl. In certain embodiments, the non-natural nucleobase is difluorotolyl. A wide variety of ligands are known in the art and are amenable to the present invention. For example, the ligand can be a steroid, bile acid, lipid, folic acid, pyridoxal, B12, riboflavin, biotin, aromatic compound, polycyclic compound, crown ether, intercalator, cleaver molecule, protein-binding agent, or carbohydrate. In certain embodiments, the ligand is a steroid or aromatic compound. In certain instances, the ligand is cholesteryl.

In other embodiments, the RNAi agent is an oligonucleotide tethered to a ligand for the purposes of improving cellular targeting and uptake. For example, an RNAi agent may be tethered to an antibody, or antigen binding fragment thereof. As an additional example, an RNAi agent may be tethered to a specific ligand binding molecule, such as a polypeptide or polypeptide fragment that specifically binds a particular cell-surface receptor.

In other embodiments, the modulating agent comprises a non-natural nucleobase. In certain embodiments, the non-natural nucleobase is difluorotolyl, nitroimidazolyl, nitroindolyl, or nitropyrrolyl. In certain embodiments, the modulating agents provided herein relate to a double-stranded oligonucleotide sequence, wherein only one of the two strands contains a non-natural nucleobase. In certain embodiments, the modulating agents as used herein relate to a double-stranded oligonucleotide sequence, wherein both of the strands independently comprise at least one non-natural nucleobase.

In certain instances, the ribose sugar moiety that naturally occurs in nucleosides is replaced with a hexose sugar. In certain aspects, the hexose sugar is an allose, altrose, glucose, mannose, gulose, idose, galactose, talose, or a derivative thereof. In a preferred embodiment, the hexose is a D-hexose. In certain instances, the ribose sugar moiety that naturally occurs in nucleosides is replaced with a polycyclic heteroalkyl ring or cyclohexenyl group. In certain instances, the polycyclic heteroalkyl group is a bicyclic ring containing one oxygen atom in the ring. In certain instances, the polycyclic heteroalkyl group is a bicyclo[2.2.1]heptane, a bicyclo[3.2.1] octane, or a bicyclo[3.3.1]nonane. In certain embodiments, the backbone of the oligonucleotide has been modified to improve the therapeutic or diagnostic properties of the oligonucleotide compound. In certain embodiments, at least one of the bases or at least one of the sugars of the oligonucleotide has been modified to improve the therapeutic or diagnostic properties of the oligonucleotide compound. In instances when the oligonucleotide is double stranded, the two strands are complementary, partially complementary, or chimeric oligonucleotides.

Examples of modified RNAi agents envisioned for use in the methods of the present invention include oligonucleotides containing modified backbones or non-natural internucleoside linkages. As defined here, oligonucleotides having modified backbones or internucleoside linkages include those that retain a phosphorus atom in the backbone and those that do not have a phosphorus atom in the backbone. Modified oligonucleotides that do not have a phosphorus atom in their intersugar backbone can also be considered to be oligonucleotides. Specific oligonucleotide chemical modifications are described below. It is not necessary for all positions in a given compound to be uniformly modified, and in fact more than one of the following modifications may be incorporated in a single oligonucleotide compound or even in a single nucleotide thereof.

Examples of modified internucleoside linkages or backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free-acid forms are also included.

Representative U.S. patents that teach the preparation of the above phosphorus atom-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050; and 5,697,248, each of which is herein incorporated by reference.

Examples of modified internucleoside linkages or backbones that do not include a phosphorus atom therein (i.e., oligonucleotides) have backbones that are formed by short chain alkyl or cycloalkyl intersugar linkages, mixed heteroatom and alkyl or cycloalkyl intersugar linkages, or one or more short chain heteroatomic or heterocyclic intersugar linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleotides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other examples of oligonucleotide mimetics, both the sugar and the internucleoside linkage, i.e., the backbone, of the nucleoside units may be replaced with novel groups. The nucleobase units are maintained for hybridization with an appropriate nucleic acid target compound. One such oligonucleotide, an oligonucleotide mimetic, that has been shown to have excellent hybridization properties, is referred to as a peptide nucleic acid (PNA). In PNA compounds, the sugar-backbone of an oligonucleotide is replaced with an amide-containing backbone, in particular an aminoethylglycine backbone. The nucleobases are retained and are bound directly or indirectly to atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497.

The present invention further encompasses oligonucleotides employing ribozymes. Synthetic RNA molecules and derivatives thereof that catalyze highly specific endoribonuclease activities are known as ribozymes. (See, generally, U.S. Pat. No. 5,543,508 to Haseloff et al., and U.S. Pat. No. 5,545,729 to Goodchild et al.) The cleavage reactions are catalyzed by the RNA molecules themselves. In naturally occurring RNA molecules, the sites of self-catalyzed cleavage are located within highly conserved regions of RNA secondary structure (Buzayan et al., Proc. Natl. Acad. Sci. U.S.A., 1986, 83, 8859; Forster et al., Cell, 1987, 50, 9). Naturally occurring autocatalytic RNA molecules have been modified to generate ribozymes which can be targeted to a particular cellular or pathogenic RNA molecule with a high degree of specificity. Thus, ribozymes serve the same general purpose as antisense oligonucleotides (i.e., modulation of expression of a specific gene) and, like oligonucleotides, are nucleic acids possessing significant portions of single-strandedness. That is, ribozymes have substantial chemical and functional identity with oligonucleotides and are thus considered to be equivalents for purposes of the present invention.

In certain instances, the RNAi agents for use with the methods provided herein may be modified by non-ligand group. A number of non-ligand molecules have been conjugated to oligonucleotides in order to enhance the activity, cellular distribution, cellular targeting, or cellular uptake of the oligonucleotide, and procedures for performing such conjugations are available in the scientific literature. Such non-ligand moieties have included lipid moieties, such as cholesterol (Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-5-tritylthiol (Manoharan et al., Ann. N.Y. Acad. Sci., 1992, 660:306; Manoharan et al., Bioorg. Med. Chem. Lett., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). Representative U.S. patents that teach the preparation of such oligonucleotide conjugates have been listed above. Typical conjugation protocols involve the synthesis of oligonucleotides bearing an aminolinker at one or more positions of the sequence. The amino group is then reacted with the molecule being conjugated using appropriate coupling or activating reagents. The conjugation reaction may be performed either with the oligonucleotide still bound to the solid support or following cleavage of the oligonucleotide in solution phase. Purification of the oligonucleotide conjugate by HPLC typically affords the pure conjugate.

Additional examples of modulating agents, such as RNAi oligonucleotides, may be found in U.S. Application Publication Nos. 2007/0275465, 2007/0054279, 2006/0287260, 2006/0035254, 2006/0008822, which are incorporated by reference.

Methods of Use

In another aspect, the present invention relates to methods of using the IL-23/17 signaling gene-targeted antisense or RNAi agents described herein for treating a cell, tissue or subject, typically to modulate the activity of an IL-23/17 signaling component in a therapeutically beneficial manner. The cells or tissue that may be modulated by the present invention are preferably mammalian cells, or more preferably human cells. Such cells can be of a healthy state or of a diseased state.

In certain embodiments, for example, methods are provided for modulating therapeutically relevant cellular activities including, but not limited to, cellular metabolism, cell differentiation, cell proliferation, cell death, cell mobilization, cell migration, immune system function (e.g., inflammation, auto-immunity), gene transcription, mRNA translation, cell impedance, cytokine production, and the like, comprising contacting a cell with an IL-23/17 signaling gene-targeted antisense or RNAi agent as described herein.

Certain preferred embodiments relate to the modulation of disease associated with hemmorhagic fever viruses (HFV). Examples of such viruses include those from the Arenaviridae, Flaviviridae, Filoviridae, Togaviridae, Arteriviridae and Bunyaviridae viral families. Specific examples of Arenaviridae include lymphocytic choriomeningitis virus (LCMV), Machupa virus, Lassa virus, Pichinde virus, Tacaribe virus, and Lugo virus. Specific examples of Flaviviridae include Dengue virus, West Nile virus, and Yellow Fever virus. Specific examples of Filoviridae include Ebola virus and Marburg virus. Specific examples of Togaviridae include Chikungunya virus, and specific examples of Arteriviridae include Simian HFV. Specific examples of Bunyaviridae include Crimean Congo virus (e.g., Congo Hemorrhagic Fever virus), Hanta virus, and Rift Valley virus. Included are methods of treating such viral infections, and methods of reducing inflammation associated with the same.

Certain embodiments include methods of decreasing inflammation, and depending on the needs of the subject and the selection of the target sequence, other embodiments include methods of increasing inflammation or inflammatory responses. "Inflammation" refers generally to the biological response of tissues to harmful stimuli, such as pathogens, damaged cells (e.g., wounds), and irritants. The term "inflammatory response" refers to the specific mechanisms by which inflammation is achieved and regulated, including, merely by way of illustration, immune cell activation or migration, cytokine production, vasodilation, including kinin release, fibrinolysis, and coagulation, among others described herein and known in the art. Ideally, inflammation is a protective attempt by the body to both remove the injurious stimuli and initiate the healing process for the affected tissue or tissues. In the absence of inflammation, wounds and infections would never heal, creating a situation in which progressive destruction of the tissue would threaten survival. On the other hand, excessive or chronic inflammation may associate with a variety of diseases, such as hay fever, atherosclerosis, and rheumatoid arthritis, among others described herein and known in the art.

The IL-23/17 signaling gene-targeted antisense and RNAi agents of the invention may modulate acute inflammation, chronic inflammation, or both. Certain embodiments relate to increasing acute inflammation or acute inflammatory responses, and certain embodiments relate to increasing chronic inflammation or chronic inflammatory responses. Depending on the needs of the subject, certain embodiments relate to reducing acute inflammation or inflammatory responses, and certain embodiments relate to reducing chronic inflammation or chronic inflammatory responses.

Acute inflammation relates to the initial response of the body to presumably harmful stimuli and involves increased movement of plasma and leukocytes from the blood into the injured tissues. It is a short-term process, typically beginning within minutes or hours and ending upon the removal of the injurious stimulus. Acute inflammation may be characterized by any one or more of redness, increased heat, swelling, pain, and loss of function. Redness and heat are due mainly to increased blood flow at body core temperature to the inflamed site, swelling is caused by accumulation of fluid, pain is typically due to release of chemicals that stimulate nerve endings, and loss of function has multiple causes.

Acute inflammatory responses are initiated mainly by local immune cells, such as resident macrophages, dendritic cells, histiocytes, Kuppfer cells and mastocytes. At the onset of an infection, burn, or other injuries, these cells undergo activation and release inflammatory mediators responsible for the clinical signs of inflammation, such as vasoactive amines and eicosanoids. Vasodilation and its resulting increased blood flow cause the redness and increased heat. Increased permeability of the blood vessels results in an exudation or leakage of plasma proteins and fluid into the tissue, which creates swelling. Certain released mediators such as bradykinin increase sensitivity to pain, and alter the blood vessels to permit the migration or extravasation of leukocytes, such as neutrophils, which typically migrate along a chemotactic gradient created by the local immune cells.

Acute inflammatory responses also includes one or more acellular biochemical cascade systems, consisting of preformed plasma proteins modulate, which act in parallel to initiate and propagate the inflammatory response. These systems include the complement system, which is mainly activated by bacteria, and the coagulation and fibrinolysis systems, which are mainly activated by necrosis, such as the type of tissue damage that is caused by certain infections, burns, or other trauma. Hence, antisense and RNAi agents may be used to modulate acute inflammation, or any of one or more of the individual acute inflammatory responses.

Chronic inflammation, a prolonged and delayed inflammatory response, is characterized by a progressive shift in the type of cells that are present at the site of inflammation, and often leads to simultaneous or near simultaneous destruction and healing of the tissue from the inflammatory process. At the cellular level, chronic inflammatory responses involve a variety of immune cells such as monocytes, macrophages, lymphocytes, plasma cells, and fibroblasts, though in contrast to acute inflammation, which is mediated mainly by granulocytes, chronic inflammation is mainly mediated by mononuclear cells such as monocytes and lymphocytes. Chronic inflammation also involves a variety of inflammatory mediators, such as IFN-$\gamma$ and other cytokines, growth factors, reactive oxygen species, and hydrolytic enzymes. Chronic inflammation may last for many months or years, and may result in undesired tissue destruction and fibrosis.

Clinical signs of chronic inflammation are dependent upon duration of the illness, inflammatory lesions, cause and anatomical area affected. (see, e.g., Kumar et al., Robbins Basic Pathology-$8^{th}$ Ed., 2009 Elsevier, London; Miller, L M, Pathology Lecture Notes, Atlantic Veterinary College, Charlottetown, PEI, Canada). Chronic inflammation is associated with a variety of pathological conditions or diseases, including, for example, allergies, Alzheimer's disease, anemia, aortic valve stenosis, arthritis such as rheumatoid arthritis and osteoarthritis, cancer, congestive heart failure, fibromyalgia, fibrosis, heart attack, kidney failure, lupus, pancreatitis, stroke, surgical complications, inflammatory lung disease, inflammatory bowel disease, atherosclerosis, and psoriasis, among others described herein and known in the art. Hence, IL-23/17 signaling gene-targeted antisense and RNAi agents may be used to treat or manage chronic inflammation, modulate any of one or more of the individual chronic inflammatory responses, or treat any one or more diseases or conditions associated with chronic inflammation.

Antisense and RNAi agents may also modulate proliferative inflammation, an inflammatory process characterized by an increase in the number of tissue cells. These can encompass skin conditions such as psoriasis, seborrhea or eczema, or can also be thought of in terms of cancers and abnormal growths especially in light of accumulating evidence based on more efficient molecular methods to document even low grade chronic inflammation.

In certain embodiments, antisense and RNAi agents may modulate inflammatory responses at the cellular level, such as by modulating the activation, inflammatory molecule secretion (e.g., cytokine or kinin secretion), proliferation, activity, migration, or adhesion of various cells involved in inflammation. Examples of such cells include immune cells and vascular cells. Immune cells include, for example, granulocytes such as neutrophils, eosinophils and basophils, macrophages/monocytes, lymphocytes such as B-cells, killer T-cells (i.e., CD8+ T-cells), helper T-cells (i.e., CD4+ T-cells, including $T_h1$ and $T_h2$ cells), natural killer cells, $\gamma\delta$ T-cells, dendritic cells, and mast cells. Examples of vascular cells include smooth muscle cells, endothelial cells, and fibroblasts. Also included are methods of modulating an inflammatory condition associated with one or more immune cells or vascular cells, including neutrophil-mediated, macrophage-mediated, and lymphocyte-mediated inflammatory conditions.

In certain embodiments, antisense and RNAi agents may modulate the levels or activity of inflammatory molecules, including plasma-derived inflammatory molecules and cell-derived inflammatory molecules (e.g., TNF-alpha, IL-1, IL-2, IL-5, adhesion molecules, Cox-2, and others). Included are pro-inflammatory molecules and anti-inflammatory molecules. Examples of plasma-derived inflammatory molecules include, without limitation, proteins or molecules of any one or more of the complement system, kinin system, coagulation system, and the fibrinolysis system. Examples of members of the complement system include C1, which exists in blood serum as a molecular complex containing about 6 molecules of C1q, 2 molecules of C1r, and 2 molecules of C1s, C2 (a and b), C3 (a and B), C4 (a and b), C5, and the membrane attack complex of C5a, C5b, C6, C7, C8, and C9. Examples of the kinin system include bradykinin, kallidin, kallidreins, carboxypeptidases, angiotensin-converting enzyme, and neutral endopeptidase.

Examples of cell-derived inflammatory molecules include, without limitation, enzymes contained within lysosome granules, vasoactive amines, eicosanoids, cytokines, acute-phase proteins, and soluble gases such as nitric oxide. Vasoactive amines contain at least one amino group, and target blood vessels to alter their permeability or cause vasodilation. Examples of vasoactive amines include histamine and serotonin. Eicosanoids refer to signaling molecules made by oxidation of twenty-carbon essential fatty acids, and include prostaglandins, prostacyclins, thromboxanes, and leukotrienes.

Cytokines refer to a variety of substances that are secreted by immune cells, and include polypeptides and glycoproteins. Typically, cytokines are categorized as either autocrine cytokines, which act on the same type of cell from which the cytokine is secreted, or paracrine cytokines, which are restricted to acting on a different cell type from which the cytokine is secreted. Examples of cytokines that can be modulated include GM-CSF, IL-1a, IL1b, IL-2, IL-3, IL-4, IL-5, IL-6, IL-7, IL-8, IL-9, IL-10, IL-12, IFN-$\alpha$, IFN-gamma, MIP-1$\alpha$, MIP-1$\beta$, TGF-$\beta$, TNF-$\alpha$, TNF-$\beta$, CXCL1-5, CXCL9-14, and CXCL16, among others known in the art.

Each cytokine typically has a corresponding cytokine receptor. Examples of classes of cytokine receptors include, without limitation, receptors from the immunoglobulin (Ig) superfamily, such as the IL-1 receptor types, which share structural homology with immunoglobulins (antibodies), cell adhesion molecules, and even some cytokines, and receptors from the hematopoietic growth factor family, such as the IL-2 receptor family and the receptors for GM-CSF, IL-3, and IL-5, receptors from the interferon (type 2) family, including receptors for IFN $\beta$ and $\gamma$. Additional examples include receptors from the tumor necrosis factors (TNF) (type 3) family, which share a cysteine-rich common extracellular binding domain and interact with several other non-cytokine ligands such as CD40, CD27 and CD30, receptors from the seven transmembrane helix family, including G-protein coupled receptors, and chemokine receptors such as CXCR4 and CCR5, as well as receptors for IL-8, MIP-1 and RANTES. Hence, in certain embodiments, IL-23/17 signaling gene-targeted antisense or RNAi agents may modulate the levels or activity of one or more selected cytokines, the levels or activity of one or more selected cytokine receptors, the interaction between cytokines and their receptors, or any combination thereof.

IL-23/17 signaling gene-targeted antisense and RNAi agents may also modulate levels or activity of acute-phase proteins. Examples of acute-phase proteins include C-reactive protein, serum amyloid A, serum amyloid P, and vasopressin. In certain instances, expression of acute-phase proteins can cause a range of undesired systemic effects including amyloidosis, fever, increased blood pressure, decreased sweating, malaise, loss of appetite, and somnolence. Accordingly, IL-23/17 signaling gene-targeted antisense and RNAi agents may modulate the levels or activity of acute-phase proteins, their systemic effects, or both.

In certain embodiments, antisense and RNAi agents may modulate local inflammation, systemic inflammation, or both. In certain embodiments, they may reduce or maintain (i.e., prevent further increases) local inflammation or local inflammatory responses. In certain embodiments, depending on the needs of the subject, antisense and RNAi agents may increase local inflammation or local inflammatory responses. In certain embodiments, they may reduce or maintain (i.e., prevent further increases) systemic inflammation or systemic inflammatory responses. In certain embodiments, depending on the needs of the subject, antisense and RNAi agents may increase systemic inflammation or systemic inflammatory responses.

In certain embodiments, the modulation of inflammation or inflammatory responses can be associated with one or more tissues or organs. Non-limiting examples of such tissues or organs include skin (e.g., dermis, epidermis, subcutaneous layer), hair follicles, nervous system (e.g., brain, spinal cord, peripheral nerves), auditory system or balance organs (e.g., inner ear, middle ear, outer ear), respiratory system (e.g., nose, trachea, lungs), gastroesophogeal tissues, the gastrointestinal system (e.g., mouth, esophagus, stomach, small intestines, large intestines, rectum), vascular system (e.g., heart, blood vessels and arteries), liver, gallbladder, lymphatic/immune system (e.g., lymph nodes, lymphoid follicles, spleen, thymus, bone marrow), uro-genital system (e.g., kidneys, ureter, bladder, urethra, cervix, Fallopian tubes, ovaries, uterus, vulva, prostate, bulbourethral glands, epidiymis, prostate, seminal vesicles, testicles), musculoskeletal system (e.g., skeletal muscles, smooth muscles, bone, cartilage, tendons, ligaments), adipose tissue, mammaries, and the endocrine system (e.g., hypothalamus, pituitary, thyroid, pancreas, adrenal glands). Accordingly, antisense and RNAi agents may be used to modulate inflammation associated with any of these tissues or organs, such as to treat conditions or diseases that are associated with the inflammation of these tissues or organs.

As noted above, certain embodiments may employ the antisense and RNAi agents described herein to reduce or manage (i.e., prevent further increases) inflammation or inflammatory responses associated with particular tissues or organs. Included are inflammatory responses and conditions associated with the skin, including inflammation, infections, and cancers associated with the dermal, epidermal, and subcutaneous layers of the skin. Examples of skin-associated inflammatory conditions include, without limitation, dermatitis, such as psoriasis, irritant dermatitis, seborrheic dermatitis, atopic dermatitis (eczema), allergic contact dermatitis, thermal-induced dermatitis, drug-induced dermatitis, dyshidrotic dermatitis, urticaria, autoimmune dermatitis, skin cancer such as melanoma, and bullous dermatitis. Also included are bacterial, viral and parasitic infections, erythema multiforme, erythema nodosum, granuloma annulare, poison oak/poison ivy, and toxic epidermal necrolysis.

Certain embodiments relate to reducing inflammatory responses and conditions associated with the nervous system, including inflammation, infections, and cancer associated with the brain and spinal cord of the central nervous system, the peripheral nervous system, and the meninges. Expression of inflammatory mediators including complement, adhesion molecules, cyclooxygenase enzymes and their products and cytokines is increased in experimental and clinical neurodegenerative disease, and intervention studies in experimental animals suggest that several of these factors contribute directly to neuronal injury. For instance, specific cytokines, such as interleukin-1 (IL-1), have been implicated heavily in acute neurodegeneration, such as stroke and head injury.

Examples of nervous system associated inflammatory conditions include, without limitation, meningitis (i.e., inflammation of the protective membranes covering the brain and spinal cord), myelitis, encephaloymyelitis (e.g., myalgic encephalomyelitis, acute disseminated encephalomyelitis, encephalomyelitis disseminata or multiple sclerosis, autoimmune encephalomyelitis), arachnoiditis (i.e., inflammation of the arachnoid, one of the membranes that surround and protect the nerves of the central nervous system), granuloma, drug-induced inflammation or meningitis, neurodegenerative diseases such as Alzheimer's disease, stroke, HIV-dementia, encephalitis such viral encephalitis and bacterial encephalitis, parasitic infections, inflammatory demyeleniating disorders, and auto-immune disorders such as CD8+ T Cell-mediated autoimmune diseases of the CNS. Additional examples include Parkinson's disease, myasthenia gravis, motor neuropathy, Guillain-Barre syndrome, autoimmune neuropathy, Lambert-Eaton myasthenic syndrome, paraneoplastic neurological disease, paraneoplastic cerebellar atrophy, non-paraneoplastic stiff man syndrome, progressive cerebellar atrophy, Rasmussen's encephalitis, amyotrophic lateral sclerosis, Sydeham chorea, Gilles de la Tourette syndrome, autoimmune polyendocrinopathy, dysimmune neuropathy, acquired neuromyotonia, arthrogryposis multiplex, optic neuritis, and stiff-man syndrome.

As noted above, also included is inflammation associated with infections of the nervous system. Specific examples of bacterial infections associated with inflammation of the nervous system include, without limitation, streptococcal infection such as group B streptococci (e.g., subtypes III) and *Streptococcus pneumoniae* (e.g., serotypes 6, 9, 14, 18 and 23), *Escherichia coli* (e.g., carrying K1 antigen), *Listeria monocytogenes* (e.g., serotype IVb), neisserial infection such as *Neisseria meningitidis* (meningococcus), staphylococcal infection, heamophilus infection such as *Haemophilus influenzae* type B, *Klebsiella*, and *Mycobacterium tuberculosis*. Also included are infections by staphylococci and *pseudomonas* and other Gram-negative bacilli, mainly with respect to trauma to the skull, which gives bacteria in the nasal cavity the potential to enter the meningeal space, or in persons with cerebral shunt or related device (e.g., extraventricular drain, Ommaya reservoir). Specific examples of viral infections associated with inflammation of the nervous system include, without limitation, enteroviruses, herpes simplex virus type 1 and 2, human T-lymphotrophic virus, varicella zoster virus (chickenpox and shingles), mumps virus, human immunodeficiency virus (HIV), and lymphocytic choriomeningitis virus (LCMV). Meningitis may also result from infection by spirochetes such as *Treponema pallidum* (syphilis) and *Borrelia burgdorferi* (Lyme disease), parasites such as malaria (e.g., cerebral malaria), fungi such as *Cryptococcus neoformans*, and ameoba such as *Naegleria fowleri*.

Meningitis or other forms of nervous system inflammation may also associate with the spread of cancer to the meninges (malignant meningitis), certain drugs such as non-steroidal anti-inflammatory drugs, antibiotics and intravenous immunoglobulins, sarcoidosis (or neurosarcoidosis), connective tissue disorders such as systemic lupus erythematosus, and certain forms of vasculitis (inflammatory conditions of the blood vessel wall) such as Behcet's disease. Epidermoid cysts and dermoid cysts may cause meningitis by releasing irritant matter into the subarachnoid space. Accordingly, IL-23/17 signaling gene-targeted antisense and RNAi agents may be used to treat or manage any one or more of these conditions.

Certain embodiments relate to reducing inflammatory responses and conditions associated with the auditory system or balance organs, such as the inner ear, middle ear, and the outer ear. Examples of auditory system or balance organ associated inflammatory conditions include, without limitation, outer ear inflammation (e.g., ear infections), middle ear inflammation, which may lead to fluid build-up in the normally air-filled space and associated conductive hearing loss, labyrinthitis, an inner ear infection or inflammation causing both dizziness (vertigo) and hearing loss, vestibular neuronitis, an infection of the vestibular nerve, generally viral, causing vertigo, and cochlear neuronitis, an infection of the cochlear nerve, generally viral, causing sudden deafness but no vertigo. Recipients of cochlear implants for hearing loss are at an increased risk of pneumococcal meningitis and its associated inflammation.

Certain embodiments relate to reducing inflammatory responses and conditions associated with the respiratory system, including inflammation, infections, and cancer associated with the nose, trachea, and lungs. Examples of respiratory system associated inflammatory conditions include, without limitation, atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolytis, chronic or acute bronchoconstriction, chronic bronchitis, small airways obstruction, and emphysema. Further examples include obstructive or inflammatory airways diseases such as chronic eosinophilic pneumonia, chronic obstructive pulmonary disease (COPD), COPD that includes chronic bronchitis, pulmonary emphysema or dyspnea associated or not associated with COPD, COPD that is characterized by irreversible, progressive airways obstruction, and adult respiratory distress syndrome (ARDS).

Further examples of conditions associated with pulmonary inflammation include conditions related to exacerbation of airways hyper-reactivity consequent to other drug therapy, airways disease that is associated with pulmonary hypertension, bronchitis such as acute bronchitis, acute laryngotracheal bronchitis, arachidic bronchitis, catarrhal bronchitis, croupus bronchitis, dry bronchitis, infectious asthmatic bronchitis, productive bronchitis, staphylococcus or streptococcal bronchitis and vesicular bronchitis, acute lung injury, and bronchiectasis such as cylindric bronchiectasis, sacculated bronchiectasis, fusiform bronchiectasis, capillary bronchiectasis, cystic bronchiectasis, dry bronchiectasis and follicular bronchiectasis.

COPD in particular refers to a group of lung diseases that block airflow and make it increasingly difficult for affected individuals to breathe normally. Emphysema and chronic bronchitis are the two main conditions within the group of COPD diseases, but COPD can also refer to damage caused by chronic asthmatic bronchitis, among other conditions known in the art. In most cases, damage to the airways eventually interferes with the exchange of oxygen and carbon dioxide in the lungs. Standard treatments focus mainly on controlling symptoms and minimizing further damage.

Emphysema represents one aspect of COPD. Emphysema leads to inflammation within the fragile walls of the alveoli, which may destroy some of the walls and elastic fibers, allowing small airways to collapse upon exhaling, and impairing airflow out of the lungs. Signs and symptoms of emphysema include, for instance, shortness of breath, especially during physical activities, wheezing, and chest tightness.

Chronic bronchitis represents another aspect of COPD. Chronic bronchitis is characterized by an ongoing cough, and leads to inflammation and narrowing of the bronchial tubes. This condition also causes increased mucus production, which can further block the narrowed tubes. Chronic bronchitis occurs mainly in smokers, and is typically defined as a cough that lasts for at least three months a year for two consecutive years. Signs and symptoms of chronic bronchitis include, for example, having to clear the throat first thing in the morning, especially for smokers, a chronic cough that produces yellowish sputum, shortness of breath in the later stages, and frequent respiratory infections.

As noted above, COPD refers primarily to obstruction in the lungs resulting from the two above-noted chronic lung conditions. However, many individuals with COPD have both of these conditions.

Chronic asthmatic bronchitis represents another aspect of COPD. Chronic asthmatic bronchitis is usually characterized as chronic bronchitis combined with asthma (bronchospasm). Asthma may occur when inflamed and infected secretions irritate the smooth muscles in the airways. Symptoms are similar to those of chronic bronchitis, but also include intermittent, or even daily, episodes of wheezing.

In certain embodiments, COPD is ultimately caused by cigarette smoke and other irritants. In the vast majority of cases, the lung damage that leads to COPD is caused by long-term cigarette smoking. However, other irritants may cause COPD, including cigar smoke, secondhand smoke, pipe smoke, air pollution and certain occupational fumes. Gastroesophageal reflux disease (GERD), which occurs when stomach acids wash back up into the esophagus, can not only aggravate COPD, but may even cause it in some individuals. In rare cases, COPD results from a genetic disorder that causes low levels of a protein called alpha-1-antitrypsin. Hence, risk factors for COPD include exposure to tobacco smoke, occupational exposure to dusts and chemicals (long-term exposure to chemical fumes, vapors and dusts irritates and inflames the lungs), gastroesophageal reflux disease (a severe form of acid reflux—the backflow of acid and other stomach contents into the esophagus), age (COPD develops slowly over years, so most people are at least 40 years old when symptoms begin), and genetics (a rare genetic disorder known as alpha-1-antitrypsin deficiency is the source of a few cases of COPD).

Complications or associated symptoms of COPD may include increased risk of respiratory infections, high blood pressure, heart problems (e.g., heart attacks, arrhythmias, cor pulmonale), lung cancer (smokers with chronic bronchitis are at a higher risk of developing lung cancer than are smokers who don't have chronic bronchitis), pneumonia, pneumothorax, and depression, among others known in the art. Further examples include cough that produces mucus and may be streaked with blood, fatigue, frequent respiratory infections, headaches, shortness of breath (dyspnea) that worsens with mild activity, swelling of the ankles, feet, or legs, which affects both sides of the body, and wheezing. IL-23/17 signaling gene-targeted antisense and RNAi agents may be used to reduce or manage the complications or symptoms associated with COPD or other pulmonary conditions related to inflammation.

Subjects with COPD may be identified according to routine diagnostic techniques known in the art. For instance, pulmonary function tests, such as spirometry, measure how much air the lungs can hold and how fast an individual can blow the air out of their lungs. Spirometry can detect COPD before the appearance of symptoms, and can also be used to track disease progression and monitor treatment. In addition, chest X-rays show emphysema, one of the main causes of COPD, and may also rule out other lung problems or heart failure. In addition, arterial blood gas analysis measures how effectively the lungs bring oxygen into the blood and remove carbon dioxide, providing an indication of COPD. Sputum examination, i.e., the analysis of the cells in the sputum, can identify the cause of certain lung problems and help rule out certain lung cancers. Also, computerized tomography (CT) scan produces highly-detailed images of the internal organs, which can help detect emphysema, and, thus, COPD.

As elsewhere herein, the amount of IL-23/17 signaling gene-targeted antisense or RNAi agent administered to a subject with COPD (or at risk for COPD) will depend on the characteristics of that subject, such as general health, age, sex, body weight, and tolerance to drugs, as well as the degree, severity, and type of reaction to the agent. For instance, multiple administrations may be utilized (1, 2, 3, 4, 5, 6, 7, 8, 9, 10, etc), typically at a defined frequency (number of administrations per day, per week, per month, etc).

Also included are combination therapies. For instance, one or more IL-23/17 signaling gene-targeted antisense and RNAi agents can be utilized in combination with other treatments for pulmonary inflammation or COPD. Examples of such treatments included, without limitation, lifestyle changes, such as quitting or reducing smoking or other exposure to lung irritants, lung rehabilitation, the use of bronchodilators (e.g., ipratropium, tiotropium, salmeterol, formoterol), steroids such as corticosteroids, antibiotics, metered-dose inhalers (MDIs) and dry powder inhalers (DPIs), nebulizers, replacement gene therapy for alpha-1-antitrypsin deficiency, oxygen therapy, and surgery, including bullectomy, lung volume reduction surgery, and lung transplant.

Certain embodiments relate to reducing inflammatory responses and conditions associated the gastrointestinal system, including inflammation, infections, and cancer associated with the mouth, esophagus, stomach, small intestines, large intestines, and rectum. "Gastrointestinal inflammation" as used herein refers to inflammation of a mucosal layer of the gastrointestinal tract, and encompasses acute and chronic inflammatory conditions. Acute inflammation is generally characterized by a short time of onset and infiltration or influx of neutrophils. Chronic inflammation is generally characterized by a relatively longer period of onset and infiltration or influx of mononuclear cells. Chronic inflammation can also typically characterized by periods of spontaneous remission and spontaneous occurrence. "Mucosal layer of the gastrointestinal tract" is meant to include mucosa of the bowel (including the small intestine and large intestine), rectum, stomach (gastric) lining, oral cavity, and the like.

"Chronic gastrointestinal inflammation" refers to inflammation of the mucosal of the gastrointestinal tract that is characterized by a relatively longer period of onset, is long-lasting (e.g., from several days, weeks, months, or years and up to the life of the subject), and is often associated with infiltration or influx of mononuclear cells, and can be further associated with periods of spontaneous remission and spontaneous occurrence. "Chronic gastrointestinal inflammatory conditions" (also referred to as "chronic gastrointestinal inflammatory diseases") having such chronic inflammation include, but are not limited to, inflammatory bowel disease (IBD), colitis induced by environmental insults (e.g., gastrointestinal inflammation associated with a therapeutic regimen, such as chemotherapy, radiation therapy, and the like), colitis in conditions such as chronic granulomatous disease (see, e.g., Schappi et al., *Arch Dis Child.* 84:147-151, 2001), celiac disease, celiac sprue (i.e., a heritable disease in which the intestinal lining is inflamed in response to the ingestion of a protein known as gluten), food allergies, gastritis, infectious gastritis or enterocolitis (e.g., *Helicobacter pylori*-infected chronic active gastritis) and other forms of gastrointestinal inflammation caused by an infectious agent, and other like conditions.

As used herein, "inflammatory bowel disease" or "IBD" refers to any of a variety of diseases characterized by inflammation of all or part of the intestines. Examples of inflammatory bowel disease include, but are not limited to, Crohn's disease and ulcerative colitis. The term IBD includes pseudomembranous colitis, hemorrhagic colitis, hemolytic-uremic syndrome colitis, collagenous colitis, ischemic colitis, radiation colitis, drug and chemically induced colitis, diversion colitis, ulcerative colitis, irritable bowel syndrome, irritable colon syndrome and Crohn's disease; and within Crohn's disease all the subtypes including active, refractory, and fistulizing and Crohn's disease. Hence, IL-23/17 signaling gene-targeted antisense and RNAi agents may be employed to treat or manage any one or more of these conditions.

Certain embodiments relate to reducing inflammatory responses and conditions associated with the vascular system, or vascular inflammation, such as inflammation associated with the blood vessels and the heart. Examples of vascular system associated inflammatory conditions include, without limitation, myocarditis, pericarditis, occlusive disease, atherosclerosis, myocardial infarction, thrombosis, Wegener's granulomatosis, Takayasu's arteritis, Kawasaki syndrome, anti-factor VIII autoimmune disease, necrotizing small vessel vasculitis, microscopic polyangiitis, Churg and Strauss syndrome, pauci-immune focal necrotizing glomerulonephritis, crescentic glomerulonephritis, antiphospholipid syndrome, antibody induced heart failure, thrombocytopenic purpura, autoimmune hemolytic anemia, cardiac autoimmunity in Chagas' disease, and anti-helper T lymphocyte autoimmunity. Also included are endocarditis, or infection of the heart valves with spread of small clusters of bacteria through the bloodstream, phlebitis or vasculitis, inflammation of one or more veins, and thrombophlebitis, vein inflammation related to a thrombus. Thrombophlebitis may occur repeatedly in different locations, and is then referred to as thrombophlebitis migrans, or migrating thrombophlebitis. Phlebitis may associate with a variety of causes, such as bacterial infection, exposure to chemical agents, such as irritating or vesicant solutions, physical trauma from skin puncture such as movement of a cannula into the vein during insertion, medications such as Celebrex, Olanzepine, antidepressants, and others, and alcohol abuse. Certain embodiments may relate to treating or managing heart inflammation caused by any one or more of acute rheumatic fever, congenital toxoplasmosis, enterovirus antenatal infection, lyme disease, and rheumatic fever.

Certain embodiments relate to reducing inflammatory responses and conditions associated with the liver or gallbladder, including acute and chronic liver inflammation, and acute and chronic cholecystis. Examples of liver or gallbladder associated inflammatory conditions include, without limitation, auto-immune hepatitis, viral hepatitis (e.g., Hepatitis A virus, Hepatitis B virus, Hepatitis C virus, Hepatitis D virus, Hepatitis E virus, mononucleosis, rubella, Epstein-Barr virus, and cytomegalovirus), other causes of hepatitis such as severe bacterial infection, ameobic infections, medicines (e.g., agomelatine, allopurinol, amitryptyline, amiodarone, asathioprine, paracetamol, halothane, ibuprofen, indomethacin, isoniazid, rifampicin, pyrazinamide, ketoconazole, loratadine, methotrexate, methyldopa, minocycline, nifedipine, nitrofurantoin, phenytoin, valproic acid, troglitazone, zidovudine), toxins (e.g., alcohol, fungal toxins), and metabolic disorders (e.g., Wilson's disease, a disorder of the body's copper metabolism, haemochromatosis, disorder of the body's iron metabolism, non-alcoholic steatohepatitis, alpha 1-antitrypsin deficiency). Additional examples include non-alcoholic fatty liver disease, cirrhosis such as primary biliary cirrhosis, obstructive jaundice, ischemic hepatitis, and gall bladder disease.

Certain embodiments relate to reducing inflammatory responses and conditions associated with the lymphatic/immune system. Examples of lymphatic/immune system associated inflammatory conditions include, without limitation, auto-immune diseases, such as Chagas disease, chronic obstructive pulmonary disorder (COPD), Crohn's disease, dermatomyositis, diabetes mellitus type I, endometriosis, Goodpasture's syndrome, Graves' disease, Guillain-Barre syndrome, Hachimoto's disease, hidradenitis suppurativa, Kawasaki disease, IgA nephropathy, idiopathic thrombocytopenia purpura, interstitial cystitis, lupus erythematosus, mixed connective tissue disease, morphea, myasthenia gravis, narcolepsy, neuromyotonia, pemphigus vulgaris, pernicous anemia, psoriasis, psoriatic arthritis, poliomyositis, primary biliary cirrhosis, rheumatoid arthritis, schizophrenia, scleroderma, Sjogren's syndrome, stiff person syndrome, temporal arteritis, ulcerative colitis, vitiligo, and Wegener's granulomatosis, in addition to autoimmune hemolytic anemia, and various lymphadenopathies.

Also included are immune-related inflammatory conditions associated with the transplantation of a graft, tissue, cell or organ, such as graft rejection, chronic graft rejection, subacute graft rejection, hyperacute graft rejection, acute graft rejection, and graft versus host disease. In certain embodiments, IL-23/17 signaling gene-targeted antisense and RNAi agents can be administered to a transplant donor before or during tissue removal. In certain embodiments, IL-23/17 signaling gene-targeted antisense and RNAi agents can be administered to a transplant recipient before, during, and/or after transplant therapy to reduce inflammation-related complications of transplant therapy. Examples of transplant therapies include bone marrow, stem cell, peripheral blood, liver, lung, heart, skin, and kidney, among others known in the art. Additional examples include inflammatory conditions associated with allergies, such as asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

Certain embodiments relate to reducing inflammatory responses and conditions associated with the uro-genital system. Examples of uro-genital system associated inflammatory conditions include, without limitation, inflammations, infections or cancers of the ureter, bladder, urethra, cervix, Fallopian tubes, ovaries, uterus, womb, vulva, prostate, bulbourethral glands, epidiymis, prostate, seminal vesicles, testicles, or kidneys. Also included are auto-immune interstitial nephritis, renal abscess (intrarenal or extrarenal), acute prostatitis, hematuria, urethritis (e.g., *Chlamydia* and other sexually transmitted diseases), pelvic inflammatory disease (PID), and prostatic abscess. Also included is nephritis associated with one or more of glomerulonephritis, lupus nephritis, nephropathy, gout, poisons or chemicals (e.g., ether, thallium sulfate), certain medications (e.g., piroxicam, candyl, feldene gel, fensaid, pirox), Herrmann syndrome, yellow fever, immune complex diseases, typhoid fever, urethral stricture, renal tuberculosism, and post-streptococcal glomerulonephritis.

Certain embodiments relate to reducing inflammatory responses and conditions associated with the musculoskeletal system. Examples of musculoskeletal system associated inflammatory conditions include, without limitation, arthritis such as rheumatoid arthritis and psoriatic arthritis, ankylosing spondylitis, auto-immune myositis, primary Sjogren's syndrome, smooth muscle auto-immune disease, myositis, polymyositis, tendinitis, ligament inflammation, cartilage inflammation, joint inflammation, synovial inflammation, carpal tunnel syndrome, chronic muscle inflammation, and bone inflammation, including bone inflammation associated with osteoporosis and osteoarthritis. Also included are Tietze's syndrome, a benign, painful, nonsuppurative localized swelling of the costosternal, sternoclavicular, or costochondral joints, costochondritis, sternalis syndrome, xiphoidalgia, spontaneous sternoclavicular subluxation, sternocostoclavicular hyperostosis, fibromyalgia, shoulder tendinitis or bursitis, gouty arthritis, polymyalgia rheumatica, lupus erythematosus, bone spurs, and fractures such as stress fractures.

Certain embodiments relate to reducing inflammatory responses and conditions associated with the endocrine system. Examples of endocrine system associated inflammatory conditions include, without limitation, inflammation, infection, or cancer associated with the hypothalamus, pituitary, thyroid, pancreas, or adrenal glands, glandular diseases such as pancreatic disease, diabetes such as Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome.

Certain embodiments relate to reducing inflammatory responses and conditions associated with adipose tissues, an active participant in regulating physiologic and pathologic processes, including immunity and inflammation. Macrophages are components of adipose tissue and actively participate in its activities. Furthermore, cross-talk between lymphocytes and adipocytes can lead to immune regulation. Adipose tissue produces and releases a variety of pro-inflammatory and anti-inflammatory factors, including the adipokines leptin, adiponectin, resistin, and visfatin, as well as cytokines and chemokines, such as TNF-alpha, IL-6, monocyte chemoattractant protein 1, and others. Proinflammatory molecules produced by adipose tissue have been implicated as active participants in the development of insulin resistance and the increased risk of cardiovascular disease associated with obesity. In contrast, reduced leptin levels may predispose to increased susceptibility to infection caused by reduced T-cell responses in malnourished individuals. Altered adipokine levels have been observed in a variety of inflammatory conditions (see, e.g., Fantuzzi, *J Allergy Clin Immunol.* 115:911-19, 2005; and Berg et al., *Circulation Research.* 96:939, 2005).

IL-23/17 signaling gene-targeted antisense and RNAi agents may also be employed to treat or manage inflammation associated with hypersensitivity. Examples of such conditions include type I hypersensitivity, type II hypersensitivity, type III hypersensitivity, type IV hypersensitivity, immediate hypersensitivity, antibody mediated hypersensitivity, immune complex mediated hypersensitivity, T-lymphocyte mediated hypersensitivity, and delayed type hypersensitivity.

IL-23/17 signaling gene-targeted antisense and RNAi agents may also be employed to treat or manage auto-inflammatory conditions. Examples of auto-inflammatory conditions include familial Mediterranean fever, TNF receptor associated periodic syndrome (TRAPS), Hyper-IgD syndrome (HIDS), CIAS1-related diseases such as Muckle-Wells syndrome, familial cold auto-inflammatory syndrome, and neonatal onset multisystem inflammatory disease, PAPA syndrome (pyogenic sterile arthritis, pyoderma gangrenosum, acne), and Blau syndrome.

IL-23/17 signaling gene-targeted antisense and RNAi agents may be employed to treat or manage inflammation associated with a variety of cancers. Examples of such cancers include, without limitation, prostate cancer, breast cancer, colon cancer, rectal cancer, lung cancer, ovarian cancer, testicular cancer, stomach cancer, bladder cancer, pancreatic cancer, liver cancer, kidney cancer, brain cancer, melanoma, non-melanoma skin cancer, bone cancer, lymphoma, leukemia, thyroid cancer, endometrial cancer, multiple myeloma, acute myeloid leukemia, neuroblastoma, glioblastoma, and non-Hodgkin's lymphoma.

As noted above, certain embodiments may employ IL-23/17 signaling gene-targeted antisense and RNAi agents to modulate systemic inflammation, such as to reduce or manage systemic inflammation. In certain embodiments, systemic inflammation may by associated with systemic inflammatory response syndrome (SIRS), a whole-body inflammatory condition with a variety of potential causes. SIRS may be characterized or identified according to routine diagnostic techniques. As one non-limiting example, SIRS may be identified by the presence of two or more of the following: (i) a body temperature that is less than 36° C. or greater than 38° C., (ii) a heart rate that is greater than 90 beats per minute, (iii) tachypnea (high respiratory rate), with greater than 20 breaths per minute; or, an arterial partial pressure of carbon dioxide less than 4.3 kPa (32 mmHg), and (iv) white blood cell count less than 4000 cells/mm$^3$ ($4\times10^9$ cells/L) or greater than 12,000 cells/mm$^3$ ($12\times10^9$ cells/L); or the presence of greater than 10% immature neutrophils (band forms).

SIRS is broadly classified as either infectious or non-infectious. Most generally, infectious SIRS is associated with sepsis, a whole-body inflammatory state combined with a known or suspected infection, which includes bacteremia, viremia, parasitemia, and toxic shock syndrome. Sepsis may be associated with a wide variety of infectious agents, including, without limitation, bacteria such as *Streptococcus agalactiae*, *Escherichia coli, Haemophilus influenzae, Listeria monocytogenes*, Coagulase-negative *Staphylococcus, Staphylococcus aureus, Klebsiella* species, *Pseudomonas aeruginosa, Enterobacter* species, *S. agalactiae, Serratia* species, *Acinetobacter* species, *Streptococcus pneumoniae, Salmonella* species, and *Neisseria meningitidis*; viruses such as rubella, cytomegalovirus, herpes simplex and the chickenpox virus; parasites such as in malarial infection (e.g., *Plasmodium falciparum*), trypanosomiasis, and filariasis; and fungi such as *Candida* species, *Aspergillus* species, *Histoplasma* species, *Cryptococcus neoformans, Coccidioides immitis, Blastomyces dermatitidis*, and *Pneumocystis carinii*. In certain instances, infections in the lungs (e.g., pneumonia), bladder and kidneys (e.g., urinary tract infections), skin (e.g., cellulitis), abdomen (e.g., appendicitis), and other areas (e.g., meningitis) can spread and lead to sepsis. IL-23/17 signaling gene-targeted antisense and RNAi agents may be used to modulate inflammation associated with any of these infectious agents, whether sepsis is present or otherwise.

Noninfectious SIRS may be associated with trauma, burns, pancreatitis, ischemia, hemorrhage, surgical complications, adrenal insufficiency, pulmonary embolism, aortic aneurysm, cardiac tamponade, anaphylaxis, and drug overdose, among others. SIRS is often complicated by the failure of one or more organs or organ system, including those described herein. Specific examples include acute lung injury, acute kidney injury, shock, and multiple organ dysfunction syndrome, among others. Typically, SIRS is treated by focusing on the underlying problem (e.g., adequate fluid replacement for hypovolemia, IVF/NPO for pancreatitis, epinephrine/steroids/benadryl for anaphylaxis). In certain instances, selenium, glutamine, and eicosapentaenoic acid have shown effectiveness in improving symptoms of SIRS, and antioxidants such as vitamin E may also be helpful. Hence, IL-23/17 signaling gene-targeted antisense and RNAi agents may be used to treat or manage SIRS and the complications of SIRS, alone or in combination with other therapies.

Systemic inflammation may also be associated with "cytokine storm," a dangerous immune reaction caused by a positive feedback loop between cytokines and immune cells, resulting in highly elevated levels of various cytokines. In certain instances, cytokine storm (hypercytokinemia) includes the systemic release of numerous known inflammatory mediators such as cytokines, oxygen free radicals, and coagulation factors). Included are elevated levels of pro-inflammatory cytokines such as TNF-alpha, IL-1, and IL-6, and anti-inflammatory cytokines such as IL-10 and IL-1 receptor antagonist. Cytokine storms can occur in a number of infectious and non-infectious diseases including graft versus host disease (GVHD), acute respiratory distress syndrome (ARDS), sepsis, avian influenza, smallpox, and SIRS. Cytokine storm may also be induced by certain medications. Treatment includes OX40 IG, which reduces T-cell responses, ACE inhibitors, Angiotensin II receptor blockers, corticosteroids, gemfibrozil, free radical scavengers, and TNF-α blockers. Accordingly, IL-23/17 signaling gene-targeted antisense and RNAi agents may be employed to treat or manage cytokine storm, alone or in combination with other therapies.

Certain embodiments may employ IL-23/17 signaling gene-targeted antisense and RNAi agents to reduce any one or more of granulomatous inflammation, fibrinous inflammation, purulent inflammation, serous inflammation, or ulcerative inflammation. Granulomatous inflammation is characterized by the formation of granulomas, typically resulting from a response to infectious agents such as tuberculosis, leprosy, and syphilis. Fibrinous inflammation results from a large increase in vascular permeability, which allows fibrin to pass through the blood vessels. If an appropriate pro-coagulative stimulus is present, such as a cancer cell, a fibrinous exudate is deposited. This process is commonly seen in serous cavities, where the conversion of fibrinous exudate into a scar can occur between serous membranes, limiting their function. Purulent inflammation results from the formation of a large amount of pus, which consists of neutrophils, dead cells, and fluid. Infection by pyogenic bacteria such as staphylococci is characteristic of this kind of inflammation. Large, localized collections of pus enclosed by surrounding tissues are called abscesses. Serous inflammation is characterized by the copious effusion of non-viscous serous fluid, commonly produced by mesothelial cells of serous membranes, but may also be derived from blood plasma. Examples of this type of inflammation include skin blisters. Ulcerative inflammation, which typically occurs near an epithelium, results in the necrotic loss of tissue from the surface, thereby exposing lower layers of tissue. The subsequent excavation of the epithelium is known as an ulcer.

IL-23/17 signaling gene-targeted antisense and RNAi agents may also be employed in the treatment of physical injuries or wounds. Examples are abrasions, bruises, cuts, puncture wounds, lacerations, impact wounds, concussions, contusions, thermal burns, frostbite, chemical burns, sunburns, gangrene, necrosis, desiccations, radiation burns, radioactivity burns, smoke inhalation, torn muscles, pulled muscles, torn tendons, pulled tendons, pulled ligaments, torn ligaments, hyperextensions, torn cartilage, bone fractures, pinched nerves, ulcers, and gunshot or other traumatic wounds.

IL-23/17 signaling gene-targeted antisense and RNAi agents may also be employed to treat or manage idiopathic inflammation or inflammation of unknown etiology. Also included are combination therapies, in which one or more IL-23/17 signaling gene-targeted antisense and RNAi agents are administered or utilized in combination with one or more other therapies for any of the inflammatory diseases or conditions described herein, including those therapies that are commonly available and known in the art. Examples of combination therapies include the use of standard anti-inflammatory agents such as non-steroidal anti-inflammatory drugs (NSAIDs), immune selective anti-inflammatory derivatives (ImSAIDs), and steroids (e.g., corticosteroids), anti-infectives such as antibiotics and anti-viral agents, anti-oxidants, cytokines, chemotherapeutic agents and other anti-cancer therapies, and immunosuppressive therapies.

Criteria for assessing the signs and symptoms of inflammatory and other conditions, including for purposes of making differential diagnosis and also for monitoring treatments such as determining whether a therapeutically effective dose has been administered in the course of treatment, e.g., by determining improvement according to accepted clinical criteria, will be apparent to those skilled in the art and are exemplified by the teachings of e.g., Berkow et al., eds., The Merck Manual, 16$^{th}$ edition, Merck and Co., Rahway, N.J., 1992; Goodman et al., eds., Goodman and Gilman's The Pharmacological Basis of Therapeutics, 10$^{th}$ edition, Pergamon Press, Inc., Elmsford, N.Y., (2001); Avery's Drug Treatment: Principles and Practice of Clinical Pharmacology and Therapeutics, 3rd edition, ADIS Press, Ltd., Williams and Wilkins, Baltimore, Md. (1987); Ebadi, Pharmacology, Little, Brown and Co., Boston, (1985); Osol ci al., eds., Remington's Pharmaceutical Sciences, 18$^{th}$ edition, Mack Publishing Co., Easton, Pa. (1990); Katzung, Basic and Clinical Pharmacology, Appleton and Lange, Norwalk, Conn. (1992).

Certain embodiments include modulation of IL-23/17 signaling genes such as IL-17RC for the treatment of auto-immune conditions. Examples of auto-immune conditions include but are not limited to, autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis (for example, IgA nephropathy), multiple sclerosis, neuritis, uveitis ophthalmia, polyendocrinopathies, purpura (for example, Henloch-Scoenlein purpura), Reiter's disease, stiff-man syndrome, autoimmune pulmonary inflammation, Guillain-Barre Syndrome, insulin dependent diabetes mellitus, and autoimmune inflammatory eye disease.

Additional autoimmune diseases, disorders or conditions include, but are not limited to, autoimmune thyroiditis; hypothyroidism, including Hashimoto's thyroiditis and thyroiditis characterized, for example, by cell-mediated and humoral thyroid cytotoxicity; SLE (which is often characterized, for example, by circulating and locally generated immune complexes); Goodpasture's syndrome (which is often characterized, for example, by anti-basement membrane antibodies); pemphigus (which is often characterized, for example, by epidermal acantholytic antibodies); receptor autoimmunities such as, for example, Graves' disease (which is often characterized, for example, by antibodies to a thyroid stimulating hormone receptor; myasthenia gravis, which is often characterized, for example, by acetylcholine receptor antibodies); insulin resistance (which is often characterized, for example, by insulin receptor antibodies); autoimmune hemolytic anemia (which is often characterized, for example, by phagocytosis of antibody-sensitized red blood cells); and autoimmune thrombocytopenic purpura (which is often characterized, for example, by phagocytosis of antibody-sensitized platelets).

An effective in vivo treatment regimen using the antisense oligonucleotides or RNAi agents of the invention may vary according to the duration, dose, frequency and route of administration, as well as the condition of the subject under treatment (i.e., prophylactic administration versus administration in response to an existing condition). Accordingly, such in vivo therapy will often require monitoring by tests appropriate to the particular type of viral infection under treatment, and corresponding adjustments in the dose or treatment regimen, in order to achieve an optimal therapeutic outcome. In certain embodiments, treatment may be monitored, e.g., by general indicators of inflammation.

Pharmaceutical Formulations

In certain embodiments, the present invention provides formulations or compositions suitable for the therapeutic delivery of antisense oligomers or other agents such as RNAi agents, as described herein. Hence, in certain embodiments, the present invention provides pharmaceutically acceptable compositions that comprise a therapeutically-effective amount of one or more of the oligomers or agents described herein, formulated together with one or more pharmaceutically acceptable carriers (additives) and/or diluents. While it is possible for an oligomer of the present invention to be administered alone, it is preferable to administer the compound as a pharmaceutical formulation (composition).

Methods for the delivery of nucleic acid molecules are described, for example, in Akhtar et al., 1992, *Trends Cell Bio.*, 2:139; and *Delivery Strategies for Antisense Oligonucleotide Therapeutics*, ed. Akhtar; Sullivan et al., PCT WO 94/02595. These and other protocols can be utilized for the delivery of virtually any nucleic acid molecule, including the isolated oligomers of the present invention.

As detailed below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

Some examples of materials that can serve as pharmaceutically-acceptable carriers include, without limitation: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Additional non-limiting examples of agents suitable for formulation with the antisense oligomers of the instant invention include: PEG conjugated nucleic acids, phospholipid conjugated nucleic acids, nucleic acids containing lipophilic moieties, phosphorothioates, P-glycoprotein inhibitors (such as Pluronic P85) which can enhance entry of drugs into various tissues; biodegradable polymers, such as poly (DL-lactide-coglycolide) microspheres for sustained release delivery after implantation (Emerich, D F et al., 1999, *Cell Transplant*, 8, 47-58) Alkermes, Inc. Cambridge, Mass.; and loaded nanoparticles, such as those made of polybutylcyanoacrylate, which can deliver drugs across the blood brain barrier and can alter neuronal uptake mechanisms (*Prog Neuropsychopharmacol Biol Psychiatry*, 23, 941-949, 1999).

The invention also features the use of the composition comprising surface-modified liposomes containing poly (ethylene glycol) lipids (PEG-modified, branched and unbranched or combinations thereof, or long-circulating liposomes or stealth liposomes). Oligomers of the invention can also comprise covalently attached PEG molecules of various molecular weights. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. *Chem. Rev.* 1995, 95, 2601-2627; Ishiwata et al., *Chem. Pharm. Bull.* 1995, 43, 1005-1011). Such liposomes have been shown to accumulate selectively in tumors, presumably by extravasation and capture in the neovascularized target tissues (Lasic et al., Science 1995, 267, 1275-1276; Oku et al., 1995, Biochim. Biophys. Acta, 1238, 86-90). The long-circulating liposomes enhance the pharmacokinetics and pharmacodynamics of DNA and RNA, particularly compared to conventional cationic liposomes which are known to accumulate in tissues of the MPS (Liu et al., J. Biol. Chem. 1995, 42, 24864-24870; Choi et al., International PCT Publication No. WO 96/10391; Ansell et al., International PCT Publication No. WO 96/10390; Holland et al., International PCT Publication No. WO 96/10392). Long-circulating liposomes are also likely to protect drugs from nuclease degradation to a greater extent compared to cationic liposomes, based on their ability to avoid accumulation in metabolically aggressive MPS tissues such as the liver and spleen.

In a further embodiment, the present invention includes oligomer compositions prepared for delivery as described in U.S. Pat. Nos. 6,692,911, 7,163,695 and 7,070,807. In this regard, in one embodiment, the present invention provides an oligomer of the present invention in a composition comprising copolymers of lysine and histidine (HK) as described in U.S. Pat. Nos. 7,163,695, 7,070,807, and 6,692,911 either alone or in combination with PEG (e.g., branched or unbranched PEG or a mixture of both), in combination with PEG and a targeting moiety or any of the foregoing in combination with a crosslinking agent. In certain embodiments, the present invention provides antisense oligomers in compositions comprising gluconic-acid-modified polyhistidine or gluconylated-polyhistidine/transferrin-polylysine. One skilled in the art will also recognize that amino acids with properties similar to His and Lys may be substituted within the composition.

Certain embodiments of the oligomers described herein may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", J. Pharm. Sci. 66:1-19).

The pharmaceutically acceptable salts of the subject oligomers include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In certain embodiments, the oligomers of the present invention may contain one or more acidic functional groups and, thus, are capable of forming pharmaceutically acceptable salts with pharmaceutically acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, e.g., Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient that can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from cyclodextrins, celluloses, liposomes, micelle forming agents, e.g., bile acids, and polymeric carriers, e.g., polyesters and polyanhydrides; and an oligomer of the present invention. In certain embodiments, an aforementioned formulation renders orally bioavailable an oligomer of the present invention.

Methods of preparing these formulations or compositions include the step of bringing into association an oligomer of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. An oligomer of the present invention may also be administered as a bolus, electuary or paste.

In solid dosage forms of the invention for oral administration (capsules, tablets, pills, dragees, powders, granules, trouches and the like), the active ingredient may be mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (e.g., gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations or dosage forms for the topical or transdermal administration of an oligomer as provided herein include powders, sprays, ointments, pastes, creams, lotions, gels, solutions, patches and inhalants. The active oligomers may be mixed under sterile conditions with a pharmaceutically-acceptable carrier, and with any preservatives, buffers, or propellants which may be required. The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an oligomer of the present invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of an oligomer of the present invention to the body. Such dosage forms can be made by dissolving or dispersing the oligomer in the proper medium. Absorption enhancers can also be used to increase the flux of the agent across the skin. The rate of such flux can be controlled by either providing a rate controlling membrane or dispersing the agent in a polymer matrix or gel, among other methods known in the art.

Pharmaceutical compositions suitable for parenteral administration may comprise one or more oligomers of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject oligomers may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility, among other methods known in the art. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms may be made by forming microencapsule matrices of the subject oligomers in biodegradable polymers such as polylactide-polyglycolide. Depending on the ratio of oligomer to polymer, and the nature of the particular polymer employed, the rate of oligomer release can be controlled. Examples of other biodegradable polymers include poly(orthoesters) and poly(anhydrides). Depot injectable formulations may also prepared by entrapping the drug in liposomes or microemulsions that are compatible with body tissues.

When the oligomers of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

As noted above, the formulations or preparations of the present invention may be given orally, parenterally, topically, or rectally. They are typically given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

Regardless of the route of administration selected, the oligomers of the present invention, which may be used in a suitable hydrated form, and/or the pharmaceutical compositions of the present invention, may be formulated into pharmaceutically-acceptable dosage forms by conventional methods known to those of skill in the art. Actual dosage levels of the active ingredients in the pharmaceutical compositions of this invention may be varied so as to obtain an amount of the active ingredient which is effective to achieve the desired therapeutic response for a particular patient, composition, and mode of administration, without being unacceptably toxic to the patient.

The selected dosage level will depend upon a variety of factors including the activity of the particular oligomer of the present invention employed, or the ester, salt or amide thereof, the route of administration, the time of administration, the rate of excretion or metabolism of the particular oligomer being employed, the rate and extent of absorption, the duration of the treatment, other drugs, compounds and/or materials used in combination with the particular oligomer employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. In certain situations, dosing is one administration per day. In certain embodiments, dosing is one or more administration per every 2, 3, 4, 5, 6, 7, 8, 9, 10, 11, 12, 13, 14 days, or every 1, 2, 3, 4, 5, 6, 7, 8, 9, 10, 11, 12 weeks, or every 1, 2, 3, 4, 5, 6, 7, 8, 9, 10, 11, 12 months, as needed, to treat the desired condition.

Nucleic acid molecules can be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres, as described herein and known in the art. In certain embodiments, microemulsification technology may be utilized to improve bioavailability of lipophilic (water insoluble) pharmaceutical agents. Examples include Trimetrine (Dordunoo, S. K., et al., *Drug Development and Industrial Pharmacy*, 17(12), 1685-1713, 1991 and REV 5901 (Sheen, P. C., et al., *J Pharm Sci* 80(7), 712-714, 1991). Among other benefits, microemulsification provides enhanced bioavailability by preferentially directing absorption to the lymphatic system instead of the circulatory system, which thereby bypasses the liver, and prevents destruction of the compounds in the hepatobiliary circulation.

In one aspect of invention, the formulations contain micelles formed from an oligomer as provided herein and at least one amphiphilic carrier, in which the micelles have an average diameter of less than about 100 nm. More preferred embodiments provide micelles having an average diameter less than about 50 nm, and even more preferred embodiments provide micelles having an average diameter less than about 30 nm, or even less than about 20 nm.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastro-intestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Examples of amphiphilic carriers include saturated and monounsaturated polyethyleneglycolyzed fatty acid glycerides, such as those obtained from fully or partially hydrogenated various vegetable oils. Such oils may advantageously consist of tri-, di-, and mono-fatty acid glycerides and di- and mono-polyethyleneglycol esters of the corresponding fatty acids, with a particularly preferred fatty acid composition including capric acid 4-10, capric acid 3-9, lauric acid 40-50, myristic acid 14-24, palmitic acid 4-14 and stearic acid 5-15%. Another useful class of amphiphilic carriers includes partially esterified sorbitan and/or sorbitol, with saturated or mono-unsaturated fatty acids (SPAN-series) or corresponding ethoxylated analogs (TWEEN-series).

Commercially available amphiphilic carriers may be particularly useful, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

In certain embodiments, the delivery may occur by use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques.

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. In certain embodiments, polymers have a molecular weight of from about 100 or 120 daltons up to about 5,000 or 10,000 daltons, or from about 300 daltons to about 5,000 daltons. In other embodiments, the polymer is polyethyleneglycol having a molecular weight of from about 100 to about 5,000 daltons, or having a molecular weight of from about 300 to about 5,000 daltons. In certain embodiments, the polymer is polyethyleneglycol of 750 daltons (PEG(750)). Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins are cyclic oligosaccharides, consisting of 6, 7 or 8 glucose units, designated by the Greek letter α, β. or γ, respectively. The glucose units are linked by α-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds, including, for instance, steroid compounds such as 17α-estradiol (see, e.g., van Uden et al. Plant Cell Tiss. Org. Cult. 38:1-3-113 (1994)). The complexation takes place by Van der Waals interactions and by hydrogen bond formation. For a general review of the chemistry of cyclodextrins, see, Wenz, Agnew. Chem. Int. Ed. Engl., 33:803-822 (1994).

The physico-chemical properties of the cyclodextrin derivatives depend strongly on the kind and the degree of substitution. For example, their solubility in water ranges from insoluble (e.g., triacetyl-beta-cyclodextrin) to 147% soluble (w/v) (G-2-beta-cyclodextrin). In addition, they are soluble in many organic solvents. The properties of the cyclodextrins enable the control over solubility of various formulation components by increasing or decreasing their solubility.

Numerous cyclodextrins and methods for their preparation have been described. For example, Parmeter (I), et al. (U.S. Pat. No. 3,453,259) and Gramera, et al. (U.S. Pat. No. 3,459,731) described electroneutral cyclodextrins. Other derivatives include cyclodextrins with cationic properties [Parmeter (II), U.S. Pat. No. 3,453,257], insoluble crosslinked cyclodextrins (Solms, U.S. Pat. No. 3,420,788), and cyclodextrins with anionic properties [Parmeter (III), U.S. Pat. No. 3,426, 011]. Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin [see, Parmeter (III), supra]. Furthermore, sulfoalkyl ether cyclodextrin derivatives have been described by Stella, et al. (U.S. Pat. No. 5,134,127).

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 μm in diameter; large unilamellar vesicles (LUVS) are typically larger than 0.05 μm. Oligolamellar large vesicles and multilamellar vesicles have multiple, usually concentric, membrane layers and are typically larger than 0.1 μm. Liposomes with several nonconcentric membranes, i.e., several smaller vesicles contained within a larger vesicle, are termed multivesicular vesicles.

One aspect of the present invention relates to formulations comprising liposomes containing an oligomer of the present invention, where the liposome membrane is formulated to provide a liposome with increased carrying capacity. Alternatively or in addition, the compound of the present invention may be contained within, or adsorbed onto, the liposome bilayer of the liposome. An oligomer of the present invention may be aggregated with a lipid surfactant and carried within the liposome's internal space; in these cases, the liposome membrane is formulated to resist the disruptive effects of the active agent-surfactant aggregate.

According to one embodiment of the present invention, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

Active agents contained within liposomes of the present invention are in solubilized form. Aggregates of surfactant and active agent (such as emulsions or micelles containing the active agent of interest) may be entrapped within the interior space of liposomes according to the present invention. A surfactant acts to disperse and solubilize the active agent, and may be selected from any suitable aliphatic, cycloaliphatic or aromatic surfactant, including but not limited to biocompatible lysophosphatidylcholines (LPCs) of varying chain lengths (for example, from about C14 to about C20). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMCs in the micromolar range; higher CMC surfactants may be utilized to prepare micelles entrapped within liposomes of the present invention.

Liposomes according to the present invention may be prepared by any of a variety of techniques that are known in the art. See, e.g., U.S. Pat. No. 4,235,871; Published PCT applications WO 96/14057; New RRC, Liposomes: A practical approach, IRL Press, Oxford (1990), pages 33-104; Lasic DD, Liposomes from physics to applications, Elsevier Science Publishers BV, Amsterdam, 1993. For example, liposomes of the present invention may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In another exemplary formulation procedure, the active agent is first dispersed by sonication in a lysophosphatidylcholine or other low CMC surfactant (including polymer grafted lipids) that readily solubilizes hydrophobic molecules. The resulting micellar suspension of active agent is then used to rehydrate a dried lipid sample that contains a suitable mole percent of polymer-grafted lipid, or cholesterol. The lipid and active agent suspension is then formed into liposomes using extrusion techniques as are known in the art, and the resulting liposomes separated from the unencapsulated solution by standard column separation.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323 (Apr. 12, 1988). In certain embodiments, reagents such as DharmaFECT® and Lipofectamine® may be utilized to introduce polynucleotides or proteins into cells.

The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In most cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. The range is typically between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

An oligomer may be formulated to be contained within, or, adapted to release by a surgical or medical device or implant. In certain aspects, an implant may be coated or otherwise treated with an oligomer. For example, hydrogels, or other polymers, such as biocompatible and/or biodegradable polymers, may be used to coat an implant with the compositions of the present invention (i.e., the composition may be adapted for use with a medical device by using a hydrogel or other polymer). Polymers and copolymers for coating medical devices with an agent are well-known in the art. Examples of implants include, but are not limited to, stents, drug-eluting stents, sutures, prosthesis, vascular catheters, dialysis catheters, vascular grafts, prosthetic heart valves, cardiac pacemakers, implantable cardioverter defibrillators, IV needles, devices for bone setting and formation, such as pins, screws, plates, and other devices, and artificial tissue matrices for wound healing.

In addition to the methods provided herein, the oligomers for use according to the invention may be formulated for administration in any convenient way for use in human or veterinary medicine, by analogy with other pharmaceuticals. The antisense oligomers and their corresponding formulations may be administered alone or in combination with other therapeutic strategies in the treatment of inflammation.

In accordance with the invention, routes of antisense oligomer delivery include, but are not limited to, various systemic routes, including oral and parenteral routes, e.g., intravenous, subcutaneous, intraperitoneal, and intramuscular, as well as inhalation, transdermal, pulmonary and topical delivery. The appropriate route may be determined by one of skill in the art, as appropriate to the condition of the subject under treatment. For example, an appropriate route for delivery of an antisense oligomer in the treatment of a condition of the skin may include topical delivery, while delivery of a antisense oligomer for the treatment of a respiratory condition (e.g., COPD) may include inhalation, intranasal or pulmonary delivery. The oligomer may also be delivered directly to the site of inflammation infection, or to the bloodstream.

The antisense oligomer may be administered in any convenient vehicle which is physiologically acceptable. Such a composition may include any of a variety of standard pharmaceutically acceptable carriers employed by those of ordinary skill in the art. Examples include, but are not limited to, saline, phosphate buffered saline (PBS), water, aqueous ethanol, emulsions, such as oil/water emulsions or triglyceride emulsions, tablets and capsules. The choice of suitable physiologically acceptable carrier will vary dependent upon the chosen mode of administration.

In some instances, as noted above, liposomes may be employed to facilitate uptake of the antisense oligonucleotide into cells. (See, e.g., Williams, S. A., Leukemia 10(12):1980-1989, 1996; Lappalainen et al., Antiviral Res. 23:119, 1994; Uhlmann et al., antisense oligonucleotides: a new therapeutic principle, Chemical Reviews, Volume 90, No. 4, pages 544-584, 1990; Gregoriadis, G., Chapter 14, Liposomes, Drug Carriers in Biology and Medicine, pp. 287-341, Academic Press, 1979). Hydrogels may also be used as vehicles for antisense oligomer administration, for example, as described in WO 93/01286 or PCT Application No US1992/005305. Alternatively, the oligonucleotides may be administered in microspheres or microparticles. (See, e.g., Wu, G. Y. and Wu, C. H., J. Biol. Chem. 262:4429-4432, 1987). Alternatively, the use of gas-filled microbubbles complexed with the antisense oligomers can enhance delivery to target tissues, as described in U.S. Pat. No. 6,245,747.

Sustained release compositions may also be used. These may include semipermeable polymeric matrices in the form of shaped articles such as films or microcapsules.

In one aspect of the method, the subject is a human subject, e.g., a patient diagnosed as having a localized or systemic inflammatory condition. The condition of a patient may also dictate prophylactic administration of an antisense oligomer of the invention, e.g., in the case of a patient who (1) is immunocompromised; (2) is a burn victim; (3) has an indwelling catheter; or (4) is about to undergo or has recently undergone surgery. In one preferred embodiment, the oligomer is a phosphorodiamidate morpholino oligomer, contained in a pharmaceutically acceptable carrier, and is delivered orally. In another preferred embodiment, the oligomer is a phosphorodiamidate morpholino oligomer, contained in a pharmaceutically acceptable carrier, and is delivered intravenously (i.v.).

In certain embodiments, the antisense compounds may be administered in an amount and manner effective to result in a peak blood concentration of at least 200-400 nM antisense oligomer. Typically, one or more doses of antisense oligomer are administered, generally at regular intervals, for a period of about one to two weeks. Preferred doses for oral administration are from about 1-100 mg oligomer per 70 kg. In some cases, doses of greater than 100 mg oligomer/patient may be necessary. For i.v. administration, preferred doses are from about 1 mg to 500 mg oligomer per 70 kg. The antisense oligomer may be administered at regular intervals for a short time period, e.g., daily for two weeks or less. However, in some cases the oligomer is administered intermittently over a longer period of time. Administration may be followed by, or concurrent with, administration of an antibiotic or other therapeutic treatment. The treatment regimen may be adjusted (dose, frequency, route, etc.) as indicated, based on the results of immunoassays, other biochemical tests and physiological examination of the subject under treatment.

Animal Model of IL-17/IL-13 Mediated Inflammation

Embodiments of the present invention also include mouse models of IL-23/IL-17 mediated inflammation in humans, and associated conditions thereof. It is believed that lymphocytic choriogenic meningitis virus (LCMV) infection in the FVB mouse strain, specifically, triggers an IL-23/IL-17 mediated pathological immune condition. The symptoms of this pathological condition closely mimic the symptoms of viral hemorrhagic fever (VHF) in humans (see Table 3); however, they are not believed to result directly from viral replication, e.g., viral cell killing. Instead, the symptoms of hemorrhagic fever are believed to result from an aberrant and pathological immune response by the FVB mice to the LCMV infection. Antisense targeting of IL-17 significantly reduces these symptoms, and demonstrates the importance of the IL-17 signaling pathway in this model of hemorrhagic disease. It is therefore believed that this dysfunctional and pathological immune state is mediated by IL-17 signaling, and may further involve IL-23/IL-17 signaling pathways. In this way, the FVB/LCMV model provides a valuable system to not only to investigate VHF and identify useful therapeutic agents for treating that disease and its symptoms, but also to investigate IL-23/IL-17 mediated inflammatory conditions more generally. For instance, due to the dysfunctional IL-17 mediated immune condition experienced by the LCMV-infected FVB mice, this model can be used to identify therapeutic agents for treating a variety of inflammatory conditions that associate with IL-17 or IL-23/IL-17 signaling, even beyond the context of viral infection, including those conditions described herein and known in the art (see, e.g., Iwakura et al., *The Journal of Clinical Investigation.* 116:1218-1222, 2006).

Certain embodiments therefore include methods of identifying a compound or agent that modulates IL-17 and/or IL-23 signaling activity, comprising (a) contacting a lymphocytic choriogenic meningitis virus (LCMV)-infected FVB mouse with a test compound; (b) measuring one or more symptoms of LCMV infection, typically hemorrhagic fever, in the FVB mouse, wherein a difference of one or more symptoms compared to an untreated FVB mouse or a pre-determined value indicates that the agent modulates IL-17 and/or IL-23 signaling, thereby identifying the compound that modulates IL-17 and/or IL-23 signaling activity. Specific embodiments include methods of identifying a compound for the treatment of a viral hemorrhagic fever (HFV), comprising (a) contacting a LCMV-infected FVB mouse with a test compound; (b) measuring one or more symptoms of hemorrhagic fever in the FVB mouse, wherein a difference of one or more symptoms of VHF as compared to an untreated FVB mouse or a pre-determined value indicates that the agent treats VHF, thereby identifying an agent for the treatment of viral VHF.

Also included are animal models for identifying an agent that modulates IL-17 and/or IL-23 signaling activity, or for indentifying a compound for treatment of VHF, comprising a LCMV-infected FVB mouse, and a test compound that modulates IL-17 and/or IL-23 signaling activity and/or reduces replication of a virus that causes VHF. Preferably, the infected mouse develops symptoms of hemorrhagic fever following infection by LCMV, though the step of contacting the mouse with the agent can occur prior to or during the development of such symptoms. Accordingly, certain test compounds or agents, if administered prior to development of symptoms of hemorrhagic fever, may reduce or altogether prevent one or more of those symptoms from developing in the treated mouse.

Depending on the particular use of the mouse model, the methods can be practiced by measuring and comparing a variety of symptoms of hemorrhagic fever, to identify an agent that modulates IL-17 signaling, IL-23 signaling, and/or reduces replication or viral load of a virus that causes VHF. As noted above, these symptoms can be compared quantitatively or qualitatively to an appropriate control, including, for example, an LCMV-infected but untreated or vehicle only treated FVB mouse (e.g., an infected mouse that has not been exposed to a test compound), an LCMV-infected FVB mouse that has been exposed to a negative control (e.g., a compound that has been shown to have little or no effect on IL-23/IL-17 signaling and/or viral replication), or one or more pre-determined values, among other suitable controls. Pre-determined values can be identified according to routine techniques in the art, such as by measuring or observing the various symptoms of hemorrhagic in a population of LCMV-infected but untreated FVB mice, and averaging those measurements or observations. In this way, specific untreated control mice need not be utilized in every screening experiment.

Specific examples of symptoms that can be observed or measured include cutaneous hemorrhaging, mucosal hemorrhaging, dizziness, liver petechiae, hypovolemic shock, leukopenia, thrombocytopenia, viral load, and death. Symptoms related to liver and kidney function can also be measured and compared, including, for example, blood chemistry analysis to show increase or decrease in alkaline phosphatase, blood urea nitrogen, aspartate aminotransferase, alanine aminotransferase, and total bilirubin levels. Complete blood count profiles may also be used to identify agents that modulate IL-23/IL-17 signaling, and may include increases or decreases in granulocyte counts and/or platelet counts (see, e.g., Example 1). The levels of pro-inflammatory or anti-inflammatory cytokines can also be measured as indicators or symptoms of hemorrhagic fevers. Included are IL-10, IFN-gamma, TNFalpha, IL-17 and IFNalpha, among others described herein and known in the art. Also included are measurements of viral load. The practice of the present invention, however, is not limited to measuring and comparing these exemplary symptoms, because it will be readily apparent to the skilled artisan that other measurements and observations relating to this animal model of IL-23/IL-17 mediated immune dysfunction can be used to identify agents or compounds that alter that pathological immune state. Methods for qualitatively or quantitatively evaluating symptoms of hemorrhagic fever such as inflammation are described herein and well-known in the art (see, e.g., Examples 1 and 2).

In certain embodiments, the difference in value of one or more symptoms of a test animal as compared to a control animal or a pre-determined value can be statistically significant. A result or difference is typically referred to as statistically significant if it is unlikely to have occurred by chance. The significance level of a test or result relates traditionally to a frequentist statistical hypothesis testing concept. In simple cases, statistical significance may be defined as the probability of making a decision to reject the null hypothesis when the null hypothesis is actually true (a decision known as a Type I error, or "false positive determination"). This decision is often made using the p-value: if the p-value is less than the significance level, then the null hypothesis is rejected. The smaller the p-value, the more significant the result. Bayes factors may also be utilized to determine statistical significance (see, e.g., Goodman S., *Ann Intern Med* 130:1005-13, 1999).

In more complicated, but practically important cases, the significance level of a test or result may reflect an analysis in which the probability of making a decision to reject the null hypothesis when the null hypothesis is actually true is no more than the stated probability. This type of analysis allows for those applications in which the probability of deciding to reject may be much smaller than the significance level for some sets of assumptions encompassed within the null hypothesis.

In certain exemplary embodiments, a statistically significant difference may include situations wherein the measurement of a symptom provides at least about 1.2×, 1.3×, 1.4×, 1.5×, 1.6×, 1.7×, 1.8×, 1.9×. 2.0×, 2.2×, 2.4×, 2.6×, 2.8×, 3.0×, 4.0×, 5.0×, 6.0×, 7.0×, 8.0×, 9.0×, 10.0×, 15.0×, 20.0×, 50.0×, 100.0×, or greater difference in a treated animal (i.e., the test compound treated animal) as compared to an appropriate control or a pre-determined value, including all integers and decimal points in between (e.g., 1.24×, 1.25×, 2.1×, 2.5×, 60.0×, 75.0×, etc.). In certain embodiments, a statistically significant difference may include situations in which a difference in one or more symptoms provides at least about 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, 600, 700, 800, 900, 1000 percent (%) or greater difference in a treated animal as compared to an appropriate control, including all integers and decimal points in between.

As an additional example, statistically significant differences may also be determined by performing Z-testing, i.e., calculating an absolute Z score, as described herein and known in the art (see Example 1). Z-testing is typically utilized to identify significant differences between a sample mean and a population mean. For example, as compared to a standard normal table (e.g., a control tissue), at a 95% confidence interval (i.e., at the 5% significance level), a Z-score with an absolute value greater than 1.96 indicates non-randomness. For a 99% confidence interval, if the absolute Z is greater than 2.58, it means that $p<0.01$, and the difference is even more significant—the null hypothesis can be rejected with greater confidence. In these and related embodiments, an absolute Z-score of 1.96, 2, 2.58, 3, 4, 5, 6, 7, 8, 9, 10, 11, 12, 13, 14, 15, 16, 17, 18, 19, 20 or more, including all decimal points in between (e.g., 10.1, 10.6, 11.2, etc.), may provide a strong measure of statistical significance. In certain embodiments, an absolute Z-score of greater than 6 may provide exceptionally high statistical significance.

Substantial similarity relates generally to the lack of a statistically significant difference in the expression levels between the treated animal and the reference control or predetermined value. Examples of substantially similarity may include situations in which the treatment provides less than about a 0.05×, 0.1×, 0.2×, 0.3×, 0.4×, 0.5×, 0.6×, 0.7×, 0.8×, 0.9×. 1.0×, 1.1×, 1.2×, 1.3×, or 1.4× difference in symptoms in treated animal as compared to an appropriate control, including all decimal points in between (e.g., 0.15×, 0.25×, 0.35×, etc.).

The animal models and methods of the present invention can be used to evaluate a variety of test compounds or test agents for their ability to modulate IL-23/IL-17 mediated signaling, or reduce replication of viruses that cause viral hemorrhagic fever. Examples of such test compounds include antisense oligonucleotides, RNAi agents, antibodies and antigen-binding fragments thereof, as well as other binding agents, such as soluble receptors, adnectins, peptides, peptide mimetics, small molecules, aptamers, and others described herein and known in the therapeutic art. Antisense agents and RNAi agents are described elsewhere herein.

Antibodies and antigen-binding fragments thereof include polyclonal antibodies, polyclonal antibodies, single domain antibody (sdAbs or "nanobodies"), "humanized" antibody molecules, "veneered FRs" and "recombinantly veneered FRs," among other antibody-based molecules known in the art.

The term "peptide" typically refers to a polymer of amino acid residues and to variants and synthetic analogues of the same. In certain embodiments, the term "peptide" refers to relatively short polypeptides, including peptides that consist of about 2, 3, 4, 5, 6, 7, 8, 9, 10, 11, 12, 13, 14, 15, 16, 17, 18, 19, 20, 25, 30, 35, 40, 45, or 50 amino acids, including all integers and ranges (e.g., 5-10, 8-12, 10-15) in between. Peptides can be composed of naturally-occurring amino acids and/or non-naturally occurring amino acids, as described herein (see, e.g., SEQ ID NOS:15-32).

In addition to peptides consisting only of naturally-occurring amino acids, peptidomimetics or peptide analogs are also provided. Peptide analogs are commonly used in the pharmaceutical industry as non-peptide drugs with properties analogous to those of the template peptide. These types of non-peptide compound are termed "peptide mimetics" or "peptidomimetics" (Luthman, et al., *A Textbook of Drug Design and Development,* 14:386-406, 2nd Ed., Harwood Academic Publishers (1996); Joachim Grante, *Angew. Chem. Int. Ed. Engl.,* 33:1699-1720 (1994); Fauchere, J., *Adv. Drug Res.,* 15:29 (1986); Veber and Freidinger TINS, p. 392 (1985); and Evans, et al., *J. Med. Chem.* 30:229 (1987)). A peptidomimetic is a molecule that mimics the biological activity of a peptide but is no longer peptidic in chemical nature. Peptidomimetic compounds are known in the art and are described, for example, in U.S. Pat. No. 6,245,886.

The present invention also includes peptoids as test compounds. Peptoid derivatives of peptides represent another form of modified peptides that retain the important structural determinants for biological activity, yet eliminate the peptide bonds, thereby conferring resistance to proteolysis (Simon, et al., *PNAS USA*. 89:9367-9371, 1992). Peptoids are oligomers of N-substituted glycines. A number of N-alkyl groups have been described, each corresponding to the side chain of a natural amino acid. The peptidomimetics of the present invention include compounds in which at least one amino acid, a few amino acids or all amino acid residues are replaced by the corresponding N-substituted glycines. Peptoid libraries are described, for example, in U.S. Pat. No. 5,811,387.

Aptamers are also included as test compounds (see, e.g., Ellington et al., *Nature*. 346, 818-22, 1990; and Tuerk et al., *Science*. 249, 505-10, 1990). Examples of aptamers included nucleic acid aptamers (e.g., DNA aptamers, RNA aptamers) and peptide aptamers. Nucleic acid aptamers refer generally to nucleic acid species that have been engineered through repeated rounds of in vitro selection or equivalent method, such as SELEX (systematic evolution of ligands by exponential enrichment), to bind to various molecular targets such as small molecules, proteins, nucleic acids, and even cells, tissues and organisms. See, e.g., U.S. Pat. Nos. 6,376,190; and 6,387,620).

Peptide aptamers typically include a variable peptide loop attached at both ends to a protein scaffold, a double structural constraint that typically increases the binding affinity of the peptide aptamer to levels comparable to that of an antibody's (e.g., in the nanomolar range). In certain embodiments, the variable loop length may be composed of about 10-20 amino acids (including all integers in between), and the scaffold may include any protein that has good solubility and compacity properties. Certain exemplary embodiments may utilize the bacterial protein Thioredoxin-A as a scaffold protein, the variable loop being inserted within the reducing active site (-Cys-Gly-Pro-Cys-[SEQ ID NO:36] loop in the wild protein), with the two cysteines lateral chains being able to form a disulfide bridge. Methods for identifying peptide aptamers are described, for example, in U.S. Application No. 2003/0108532. Peptide aptamer selection can be performed using different systems known in the art, including the yeast two-hybrid system.

Also included as test compounds are Adnectins™, Avimers™, and anticalins. Adnectins™ refer to a class of targeted biologics derived from human fibronectin, an abundant extracellular protein that naturally binds to other proteins. See, e.g., U.S. Application Nos. 2007/0082365; 2008/0139791; and 2008/0220049. Adnectins™ typically consists of a natural fibronectin backbone, as well as the multiple targeting domains of a specific portion of human fibronectin. The targeting domains can be engineered to enable an Adnectin™ to specifically recognize a therapeutic target of interest.

Avimers™ refer to multimeric binding proteins or peptides engineered using in vitro exon shuffling and phage display. Multiple binding domains are linked, resulting in greater affinity and specificity compared to single epitope immunoglobulin domains. See, e.g., Silverman et al., *Nature Biotechnology*. 23:1556-1561, 2005; U.S. Pat. No. 7,166,697; and U.S. Application Nos. 2004/0175756, 2005/0048512, 2005/0053973, 2005/0089932 and 2005/0221384.

Also included as test compounds are designed ankyrin repeat proteins (DARPins), which include a class of non-immunoglobulin proteins that can offer advantages over antibodies for target binding in drug discovery and drug development. Among other uses, DARPins are ideally suited for in vivo imaging or delivery of toxins or other therapeutic payloads because of their favorable molecular properties, including small size and high stability. The low-cost production in bacteria and the rapid generation of many target-specific DARPins make the DARPin approach useful for drug discovery. Additionally, DARPins can be easily generated in multi-specific formats, offering the potential to target an effector DARPin to a specific organ or to target multiple receptors with one molecule composed of several DARPins. See, e.g., Stumpp et al., *Curr Opin Drug Discov Devel*. 10:153-159, 2007; U.S. Application No. 2009/0082274; and PCT/EP2001/10454.

Certain embodiments include "monobodies" as test compounds, which typically utilize the 10th fibronectin type III domain of human fibronectin (FNfn10) as a scaffold to display multiple surface loops for target binding. FNfn10 is a small (94 residues) protein with a β-sandwich structure similar to the immunoglobulin fold. It is highly stable without disulfide bonds or metal ions, and it can be expressed in the correctly folded form at a high level in bacteria. The FNfn10 scaffold is compatible with virtually any display technologies. See, e.g., Batori et al., *Protein Eng*. 15:1015-20, 2002; and Wojcik et al., *Nat Struct Mol Biol.*, 2010; and U.S. Pat. No. 6,673,901.

Anticalins refer to a class of antibody mimetics, which are typically synthesized from human lipocalins, a family of binding proteins with a hypervariable loop region supported by a structurally rigid framework. See, e.g., U.S. Application No. 2006/0058510. Anticalins typically have a size of about 20 kDa. Anticalins can be characterized by a barrel structure formed by eight antiparallel β-strands (a stable β-barrel scaffold) that are pairwise connected by four peptide loops and an attached α-helix. In certain aspects, conformational deviations to achieve specific binding are made in the hypervariable loop region(s). See, e.g., Skerra, *FEBS J*. 275:2677-83, 2008, herein incorporated by reference.

A test compound may also include one or more small molecules. A "small molecule" refers to an organic compound that is of synthetic or biological origin (biomolecule), but is typically not a polymer. Organic compounds refer to a large class of chemical compounds whose molecules contain carbon, typically excluding those that contain only carbonates, simple oxides of carbon, or cyanides. A "biomolecule" refers generally to an organic molecule that is produced by a living organism, including large polymeric molecules (biopolymers) such as peptides, polysaccharides, and nucleic acids as well, and small molecules such as primary secondary metabolites, lipids, phospholipids, glycolipids, sterols, glycerolipids, vitamins, and hormones. A "polymer" refers generally to a large molecule or macromolecule composed of repeating structural units, which are typically connected by covalent chemical bond.

In certain embodiments, a small molecule has a molecular weight of less than 1000-2000 Daltons, typically between about 300 and 700 Daltons, and including about 50, 100, 150, 200, 250, 300, 350, 400, 450, 500, 550, 500, 650, 600, 750, 700, 850, 800, 950, 1000 or 2000 Daltons.

Libraries of chemical and/or biological mixtures of small molecules, such as fungal, bacterial, or algal extracts, are known in the art and can be screened with any of the mouse models of the invention. Examples of methods for the synthesis of molecular libraries can be found in: (Carell et al., 1994a; Carell et al., 1994b; Cho et al., 1993; DeWitt et al., 1993; Gallop et al., 1994; Zuckermann et al., 1994).

Embodiments of the present invention encompass the use of different libraries for the identification of small molecule modulators of one or more of IL-17 signaling, IL-23 signaling, and/or replication of viruses that cause hemorrhagic fever. Libraries useful for the purposes of the invention include, but are not limited to, (1) chemical libraries, (2)

natural product libraries, and (3) combinatorial libraries comprised of random peptides, oligonucleotides and/or organic molecules.

Chemical libraries consist of structural analogs of known compounds or compounds that are identified as "hits" or "leads" via natural product screening. Natural product libraries can be derived from collections of microorganisms, animals, plants, or marine organisms which are used to create mixtures for screening by: (1) fermentation and extraction of broths from soil, plant or marine microorganisms or (2) extraction of plants or marine organisms. Natural product libraries include polyketides, non-ribosomal peptides, and variants (non-naturally occurring) thereof. See, e.g., Cane et al., *Science* 282:63-68, 1998. Combinatorial libraries may be composed of large numbers of peptides, oligonucleotides or organic compounds as a mixture. They are relatively easy to prepare by traditional automated synthesis methods, PCR, cloning or proprietary synthetic methods.

More specifically, a combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

For a review of combinatorial chemistry and libraries created therefrom, see, e.g., Huc, I. and Nguyen, R. (2001) *Comb. Chem. High Throughput Screen* 4:53-74; Lepre, C A. (2001) *Drug Discov. Today* 6:133-140; Peng, S. X. (2000) *Biomed. Chromatogr.* 14:430-441; Bohm, H. J. and Stahl, M. (2000) *Curr. Opin. Chem. Biol.* 4:283-286; Barnes, C and Balasubramanian, S. (2000) *Curr. Opin. Chem. Biol.* 4:346-350; Lepre, Enjalbal, C, et al., (2000) *Mass Septrom Rev.* 19:139-161; Hall, D. G., (2000) *Nat. Biotechnol.* 18:262-262; Lazo, J. S., and Wipf, P. (2000) *J. Pharmacol. Exp. Ther.* 293:705-709; Houghten, R. A., (2000) *Ann. Rev. Pharmacol. Toxicol.* 40:273-282; Kobayashi, S. (2000) *Curr. Opin. Chem. Biol.* (2000) 4:338-345; Kopylov, A. M. and Spiridonova, V. A. (2000) *Mol. Biol.* (Mosk) 34:1097-1113; Weber, L. (2000) *Curr. Opin. Chem. Biol.* 4:295-302; Dolle, R. E. (2000) *J. Comb. Chem.* 2:383-433; Floyd, C D., et al., (1999) *Prog. Med. Chem.* 36:91-168; Kundu, B., et al., (1999) *Prog. Drug Res.* 53:89-156; Cabilly, S. (1999) *Mol. Biotechnol.* 12:143-148; Lowe, G. (1999) *Nat. Prod. Rep.* 16:641-651; Dolle, R. E. and Nelson, K. H. (1999) *J. Comb. Chem.* 1:235-282; Czarnick, A. W. and Keene, J. D. (1998) *Curr. Biol.* 8:R705-R707; Dolle, R. E. (1998) *Mol. Divers.* 4:233-256; Myers, P. L., (1997) *Curr. Opin. Biotechnol.* 8:701-707; and Pluckthun, A. and Cortese, R. (1997) *Biol. Chem.* 378:443.

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd., Moscow, RU, 3D Pharmaceuticals, Exton, Pa., Martek Biosciences, Columbia, Md., etc.).

In certain embodiments, the test compound specifically binds to any one or more of IL-17, IL-23, IL-17RA, IL-17RC and IL-23R. A test compound is said to "specifically bind" to a selected target molecule if it reacts at a detectable level (within, for example, an ELISA assay) with the target molecule and does not react detectably in a statistically significant manner with unrelated molecules under similar conditions.

In other embodiments, the test compound is an antisense oligonucleotide that contains between 10-40 bases and a targeting sequence of at least 10 contiguous bases complementary to a target sequence, wherein the target sequence is a pre-mRNA transcript of a protein selected from IL-17, IL-23, IL-17RA, IL-17RC and IL-23R.

As noted above, the animal models and related methods can be used not only to study the fundamental mechanisms of IL-23/IL-17 signaling, e.g., to identify other cellular players in these pathways, particularly as they contribute to immune dysfunction, but also to identify any one or more agents or compounds for treating a variety of diseases or condition associated with IL-17 and/or IL-23 signaling. In certain embodiments, the disease or condition to be treated is viral hemorrhagic fever, which can be caused by a variety of viruses. Examples of such viruses include those from the Arenaviridae, Flaviviridae, Filoviridae, Togaviridae, Arteriviridae and Bunyaviridae viral families viral families. Specific members of these viral families are described elsewhere herein and known in the art.

In certain embodiments, the disease or condition is an inflammatory disease or condition, as described elsewhere herein and known in the art, including chronic and acute inflammatory conditions. Merely by way of non-limiting example, the inflammatory disease or condition may include asthma, allergic asthma, inflammatory bowel disease, ulcerative colitis, Crohn's disease, arthritis, atopic dermatitis or psoriasis, endotoxemia, septicemia, toxic shock syndrome, infectious disease, rheumatoid arthritis, hepatobiliary disease, atherosclerosis, promotion of tumor growth, degenerative joint disease, immune mediated renal disease, adult respiratory disease (ARD), septic shock, multiple organ failure, inflammatory lung injury, chronic obstructive pulmonary disease (COPD), airway hyper-responsiveness, chronic bronchitis, allergic asthma, bacterial pneumonia, psoriasis, eczema, systemic lupus erythematosus (SLE), multiple sclerosis, systemic sclerosis, nephrotic syndrome, organ allograft rejection, graft vs. host disease (GVHD), kidney, lung, heart, etc. transplant rejection, streptococcal cell wall (SCW)-induced arthritis, osteoarthritis, gingivitis/periodontitis, herpetic stromal keratitis, cancers including prostate, renal, colon, ovarian, cervical, leukemia, angiogenesis, restenosis and Kawasaki disease, among others. The compounds provided herein, or identified according to the animal models of the present invention, can also be used to treat any one or more of these diseases or conditions.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Materials and Methods.

All peptides were custom synthesized by Global Peptide Services (Ft. Collins, Colo.) or at AVI BioPharma (Corvallis, Oreg.) and purified to >90% purity. Phosphorodiamidate morpholino oligomers (PMO) were synthesized at AVI BioPharma in accordance with known methods, as described, for example, in ((Summerton and Weller 1997) and U.S. Pat. No. 5,185,444 and further described in PCT application No. US08/012804. Exemplary structures of the PMO are as shown in FIGS. 1A-C.

Some of the PMO oligomers were conjugated at the 3' end with one of two arginine-rich peptides ((RXRRBR)$_2$XB or (RXR)$_4$XB; SEQ ID NOs: 23 and 18, respectively) to form peptide-conjugated PMOs (PPMOs) to enhance cellular uptake as described (U.S. Pat. No. 7,468,418, PCT application No. US08/008168 and (Marshall, Oda et al. 2007; Abes, Moulton et al. 2008)).

A synthetic pathway that can be used to make morpholino subunits containing a (1-piperazino)phosphinylideneoxy linkage is described in PCT application No. US07/011435 and further experimental detail for a representative synthesis is provided below. Reaction of piperazine and trityl chloride gave trityl piperazine, which was isolated as the succinate salt. Reaction with ethyl trifluoroacetate in the presence of a weak base (such as diisopropylethylamine or DIEA) provided 1-trifluoroacetyl-4-trityl piperazine, which was immediately reacted with HCl to provide the salt in good yield. Introduction of the dichlorophosphoryl moiety was performed with phosphorus oxychloride in toluene.

The acid chloride is reacted with morpholino subunits (moN), which may be prepared as described in U.S. Pat. No. 5,185,444 or in Summerton and Weller, 1997 (cited above) and further described in PCT application No. US08/012804, to provide the activated subunits. Suitable protecting groups are used for the nucleoside bases, where necessary; for example, benzoyl for adenine and cytosine, phenylacetyl for guanine, and pivaloylmethyl for inosine. The subunits containing the (1-piperazino)phosphinylideneoxy linkage can be incorporated into the existing PMO synthesis protocol, as described, for example in Summerton and Weller (1997), without modification.

Example 1

Lethal Murine Model for Hemorrhagic Virus Infection

To address a need for improved animal models that replicate human hemorrhagic virus disease symptomology, different murine genetic backgrounds were used in arenavirus infection studies. FVB and C57BL/6 (B6) mice were infected intravenously with 2×10$^6$ PFU lymphocytic choriogenic meningitis virus clone 13 (LCMV-Cl 13 or LCMV). LCMV-Cl 13-infected FVB and C57BL/6 mice showed similar weight loss with the exception of the delayed onset of weight loss in the FVB strain as shown in FIG. 7b. LCMV-Cl 13-infected FVB mice (n=18) die between six and nine days post-infection compared to LCMV-infected C57BL/6 mice (n=10) which all survived as shown in FIG. 7a.

Investigation of internal organs showed cutaneous and mucosal hemorrhaging of FVB mice with no obvious defects in C57BL/6 mice as shown in FIG. 8. Hemorrhagic symptoms first appeared at day 6 post-infection in FVB mice. FIG. 8a shows the epidermal petichiae in LCMV-infected FVB mice at day 6 and FIG. 8b shows the massive hemorrhaging in the hind limb region of a deceased animal. Cutaneous hemorrhaging including bleeding from the eyes, fingernails and mucosal tissues is a classic hemorrhagic fever virus symptom and was observed in the LCMV/FVB model. Massive mucosal hemorrhaging from the intestines and liver were also observed in the FVB-infected mice as shown in FIG. 8c. LCMV-infected C57BL/6 mice and naïve FVB mice do not display these symptoms as shown in FIGS. 8d & 8e.

FVB mice became lethargic and sensitive to light, often wobbling when initiated to move while C57BL/6 mice maintained normal energy and behavior throughout the experiment. Blood pressure was greatly decreased in infected FVB mice compared to infected C57BL/6 mice. Complete blood count profiles revealed increased granulocyte counts in infected FVB mice and severe reduction in platelet counts as shown in FIG. 9. Infected C57BL/6 mice maintained normal levels of both granulocytes and platelets, also shown in FIG. 9. Blood chemistry analysis of infected FVB mice showed increased levels of alkaline phosphatase, blood urea nitrogen, asparatate aminotransferase, alanine aminotransferase, and total bilirubin compared to infected C57BL/6 mice demonstrating decreased liver and kidney function as shown in FIG. 9. As described above, survival of LCMV-infected FVB mice was less than 10% by 9 days post-infection whereas C57BL/6 mice maintained 100% survival up to 20 days post-infection. Viral load in liver, brain, spleen, kidney, and lung was higher in LCMV-infected C57BL/6 mice than infected FVB mice as shown in FIG. 10. Histology revealed severe splenic necrosis, liver necrosis, and interstitial pneumonia in FVB mice. The appearance of cutaneous and mucosal hemorrhaging, dizziness, liver petechiae, hypovolemic shock, death, and thrombocytopenia in FVB mice replicates many of the human clinical signs of viral hemorrhagic disease. Infected C57BL/6 mice demonstrated the well characterized wasting disease from an ongoing chronic infection, yet showed no observable signs of hemorrhagic disease.

This observation and the increased viral load in infected C57BL/6 mice compared to FVB mice point to a host-specific response that initiates hemorrhagic disease rather than a virus-mediated disease. The data demonstrate a novel model for investigation of hemorrhagic disease in mice that replicates many of the human clinical symptoms as shown below in Table 3.

TABLE 3

Comparison of viral hemorrhagic disease symptoms in Humans, guinea pigs and LCMV-infected FVB mice.

|  | Human | guinea pig | FVB mouse |
|---|---|---|---|
| Cutaneous hemorrhage | + | unknown | + |
| Mucosal hemorrhage | + | + | + |
| Dizziness | + | + | + |
| Liver Petechiae | + | − | + |
| Hypovolemic Shock | + | + | + |
| Death | + | + | + |
| Leukopenia | + | unknown | +/− |
| Thrombocytopenia | + | + | + |

Example 2

Antisense Oligomers Targeted to IL-17RC Prevents Death in a Lethal Hemorrhagic Virus Model Male FVB/NCr mice were purchased from NCI-Frederick and were infected at 8 weeks of age with LCMV-Cl 13 intravenously at 1.0×10$^6$ PFU. Three mice were treated with PPMO IL17RC-SD12 (sequence: 5' CTGGACACAGAGGT-TGG 3' (SEQ ID NO: 12) with P007 (SEQ ID NO:18) conjugated to the 5' end) with 150 ug intraperitoneally on day 0, day 1, and day 2 post-infection. Eight mice were treated with PBS only. A significant trend of increased survival and lower viral RNA copy number was observed with IL17RC-SD12 treatment as shown in FIG. 4B. FIG. 4A shows that survival of IL17RC-SD12 treated mice increased to 66% (⅔) compared to 12.5% (⅛) survival in PBS treated controls. IL17RC-SD12 treatment resulted in a two to four fold decrease in blood Alanine Aminotransferase, Aspartate Aminotransferase, Alkaline Phosphatase, and Total Bilirubin levels compared to PBS treated controls, indicating increased liver and kidney function with IL17RC-SD12 treatment as shown in FIG. 5. Viral load was significantly decreased in IL17RC-SD12 treated mice in liver, kidney, brain, and lung compared to PBS controls as shown in FIG. 4. Furthermore, IL-10, IFNgamma, TNFalpha, IL-17 and IFNalpha were significantly reduced in IL-17RC-SD12 treated, LCMV Cl 13-infected FVB mice compared to untreated FVB-infected mice as shown in FIG. 6.

The ability of the IL-17RC antisense compound to modulate the immune dysfunction observed in the FVB LCMV-infected mice demonstrates the importance of the IL-17 signaling pathway in this model of hemorrhagic disease. The FVB/LCMV model therefore provides a valuable system to investigate other strategies for therapeutic interventions in the IL-17 and IL-23 signaling pathway.

SEQUENCE LISTING

| Sequence (5' to 3') | Seq ID No |
|---|---|
| TCCCCACTGTCCAGCAGAGGGCCAGGCACATGCCCATGGAGGG GACCTGAGCAGACCCCCATTTCCTTTCCAGGTGTGGCCTCTGG AACCTGACTCCGTTAGGACGAACATCTGCCCCTTCAGGGAGGG TGAGCCGACCGGCCTGGGGCTGGGGTTGGGGTGTTGCGAGCGA TGGGTACCTGGCCTGCGGTGACTGTGCCCTTTCCTTGCAGACC CCCGCGCACACCAGAACCTCTGGCAAGCCGCCCGACTGCAACT GCTGACCCTGCAGAGCTGGCTGCTGGACGCACCGTGCTCGCTG CCCGCAGAAGCGGCACTGTGCTGGCGGGCTCCGGGTGGGGACC CCTGCCAGCCACTGGTCCCACCGCTTTCCTGGGAGAACGTCAC TGTGGACGTAAGTGAAGCAGAGGGCACCTCCCGTGGTGAGGGG AGAGTGGGGAACCGGGGGTCCCCTTTTGTGATCCCACCCATTC CTCTCTTTCCACAGAAGGTTCTCGAGTTCCCATTGCTGAAAGG CCACCCTAACCTCTGTGTTCAGGTCAGAAAGGGGTGCATAGTG CTGGGCTGGAGGCTGGACCTGGGCAGACCCCCCAGCCAAGGGG GTCTTAGTT | 1 |
| CACCCTCCCTGAAGGGGCAGATGT | 2 |
| AGAGGTTCTGGTGTGCGCGGGGGT | 3 |
| TCCCCACCCGGAGCCCGCCAGCAC | 4 |
| GTCCACAGTGACGTTCTCCCAGGA | 5 |
| CTGCTTCACTTACGTCCACAGTGA | 6 |
| ACTCGAGAACCTTCTGTGGAAAGA | 7 |
| CTGAACACAGAGGTTAGGGTGGCC | 8 |
| ATGCACCCCTTTCTGACCTGAACA | 9 |
| CCAGCCCAGCACTATGCACCCCTT | 10 |
| CTGAACACAGAGGTTAG | 11 |
| CTGGACACAGAGGTTGG | 12 |

SEQUENCE LISTING -continued

| Sequence (5' to 3') | Seq ID No |
|---|---|
| TCTGACCTGAACACAGAGGTTA | 13 |
| TCTGACCTGGACACAGAGGTTG | 14 |
| Arginine-rich Peptide Transporters | |
| RRRQRRKKRC | 15 |
| RRRRRRRRRFFC | 16 |
| RRAhxRRAhxRRAhxRRAhxB | 17 |
| RAhxRRAhxRRAhxRRAhxRAhxB | 18 |
| AhxRRAhxRRAhxRRAhxRRAhxB | 19 |
| RAhxRAhxRAhxRAhxRAhxRAhxB | 20 |
| RAhxRAhxRAhxRAhxRAhxRAhxRAhxB | 21 |
| RAhxRRAhxRRAhxRRAhxRRAhxRAhxB | 22 |
| RAhxRRBRRAhxRRBRAhxB | 23 |
| RRRRRRG | 24 |
| RRRRRRRG | 25 |
| RRRRRRRRG | 26 |
| RRRRRGRRRRG | 27 |
| RRRRRFRRRRG | 28 |
| RKKRRQRRRG | 29 |
| RRRQRRKKRG | 30 |
| RXRRGGRXRRGG | 31 |
| RXRRRXRXRRRXG | 32 |

REFERENCES

Abes, R., H. M. Moulton, et al. (2008). "Delivery of steric block morpholino oligomers by (R—X—R)4 peptides: structure-activity studies." *Nucleic Acids Res.*

Carlson, M. J., M. L. West, et al. (2009). "In vitro-differentiated TH17 cells mediate lethal acute graft-versus-host disease with severe cutaneous and pulmonary pathologic manifestations." *Blood* 113(6): 1365-74.

Egholm, M., O. Buchardt, et al. (1993). "PNA hybridizes to complementary oligonucleotides obeying the Watson-Crick hydrogen-bonding rules." *Nature* 365(6446): 566-8.

Jearawiriyapaisarn, N., H. M. Moulton, et al. (2008). "Sustained Dystrophin Expression Induced by Peptide-conjugated Morpholino Oligomers in the Muscles of mdx Mice." *Mol Ther.*

Marshall, N. B., S. K. Oda, et al. (2007). "Arginine-rich cell-penetrating peptides facilitate delivery of antisense oligomers into murine leukocytes and alter pre-mRNA splicing." *Journal of Immunological Methods* 325(1-2): 114-126.

Moulton, H. M., M. H. Nelson, et al. (2004). "Cellular uptake of antisense morpholino oligomers conjugated to arginine-rich peptides." *Bioconjug Chem* 15(2): 290-9.

Rangachari, M., N. Mauermann, et al. (2006). "T-bet negatively regulates autoimmune myocarditis by suppressing local production of interleukin 17." *J Exp Med* 203(8): 2009-19.

Summerton, J. and D. Weller (1997). "Morpholino antisense oligomers: design, preparation, and properties." *Antisense Nucleic Acid Drug Dev* 7(3): 187-95.

Wu, B., H. M. Moulton, et al. (2008). "Effective rescue of dystrophin improves cardiac function in dystrophin-deficient mice by a modified morpholino oligomer." *Proc Natl Acad Sci USA* 105(39): 14814-9.

The invention claimed is:

1. A method of identifying a compound for the treatment of viral hemorrhagic fever (VHF), comprising
   (a) contacting an lymphocytic choriogenic meningitis virus (LCMV) clone 13-infected FVB mouse with a test compound;
   (b) measuring one or more symptoms of hemorrhagic fever in the FVB mouse, wherein a difference of one or more symptoms compared to a control FVB mouse or a predetermined value of a symptom of hemorrhagic fever indicates that the test compound treats VHF, thereby identifying the compound for the treatment of VHF.

2. The method of claim 1, wherein the test compound is an antisense oligonucleotide, an RNAi agent, an antibody or antigen-binding fragment thereof, a soluble receptor, an adnectin, a peptide, a peptide mimetic, an aptamer, or a small molecule.

3. The method of claim 1, wherein the one or more symptoms are selected from cutaneous hemorrhaging, mucosal hemorrhaging, dizziness, liver petechiae, hypovolemic shock, leukopenia, thrombocytopenia, viral load, alkaline phosphatase level, blood urea nitrogen, aspartate amino transferase level, alanine amino transferase level, total bilirubin level, blood count profile, pro-inflammatory cytokine level, anti-inflammatory cytokine level, and death.

4. The method of claim 1, where VHF is caused by a virus selected from the Arenaviridae, Flaviviridae, Filoviridae, Togaviridae, Arteriviridae and Bunyaviridae viral families.

5. The method of any one of claims 1-4, wherein the compound specifically binds to interleukin-17 (IL-17).

6. The method of any one of claims 1-4, wherein the compound modulates IL-17 signaling activity.

7. The method of claim 1, wherein the test compound is a morpholino antisense oligonucleotide of 10-40 bases comprising a targeting sequence of at least 10 contiguous bases complementary to a target sequence, wherein the target sequence is a pre-mRNA transcript encoding a protein selected from IL-17, IL-23, IL-17RA, IL-17RC, and IL-23R.

8. The method of claim 7, wherein the morpholino antisense oligonucleotide alters splicing of the pre-mRNA transcript and increases expression of a variant of at least one of IL-17, IL-23, IL-17RA, IL-17RC, and IL-23R.

9. The method of claim 7, wherein the morpholino antisense oligonucleotide induces full or partial exon-skipping of one or more exons of the pre-mRNA transcript.

10. The method of claim 7, wherein the morpholino antisense oligonucleotide contains about 5%-50% intersubunit cationic linkages.

11. The method of claim 10, wherein the intersubunit cationic linkages are 1-piperazino containing intersubunit linkages.

12. The method of claim 7, wherein the morpholino antisense oligonucleotide comprises an arginine-rich carrier peptide.

13. The method of claim 12, wherein the arginine-rich carrier peptide is linked at its C-terminus to the 5' end of the morpholino antisense oligonucleotide through a one- or two-amino acid linker.

14. The method of claim 12, wherein the arginine-rich carrier peptide is linked at its C-terminus to the 3' end of the morpholino antisense oligonucleotide through a one- or two-amino acid linker.

15. The method of claim 14, wherein the amino acid linker is AhxβAla, wherein Ahx is 6-amino hexanoic acid and βAla is β-alanine.

16. The method of claim 12, wherein the arginine-rich carrier peptide is selected from SEQ ID NOS:15-32.

17. The method of claim 7, wherein the morpholino subunits of the morpholino antisense oligonucleotide are joined by phosphorus-containing linkages, in accordance with the structure:

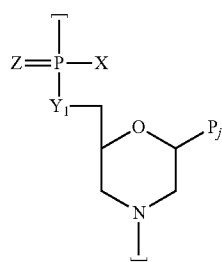

wherein Z is S or O,
X=NR$^1$R$^2$ or OR$^6$,
Y=O or NR$^7$,
and each said linkage is selected from:
(a) uncharged linkage (a), wherein each of R$^1$, R$^2$, R$^6$, and R$^7$ is independently selected from hydrogen and lower alkyl;
(b1) cationic linkage (b1), wherein X=NR$^1$R$^2$ and Y=O, and NR$^1$R$^2$ represents an optional substituted piperazino group, such that R$^1$R$^2$=—CHRCHRN(R$^3$)(R$^4$)CHRCHR—, wherein
each R$^4$ is H, CH$_3$ or null, and
R$^3$ is selected from H, lower alkyl, C(=NH)NH$_2$, Z-L-NHC(=NH)NH$_2$, and
[C(O)CHR'NH]$_m$H, wherein where Z is carbonyl (C(O)) or a direct bond, L is an optional linker up to 18 atoms in length having bonds selected from alkyl, alkoxy, and alkylamino, R' is a side chain of a naturally occurring amino acid or a one- or two-carbon homolog thereof, and m is 1 to 6;

(b2) cationic linkage (b2), wherein X=NR$^1$R$^2$ and Y=O, R$^1$=H or CH$_3$, and R$^2$=LNR$^3$R$^4$R$^5$, wherein L, R$^3$, and R$^4$ are defined as above, and R$^5$ is H, lower alkyl, or lower (alkoxy)alkyl; and (b3) cationic linkage (b3), wherein Y=NR$^7$ and X=OR$^6$, and R$^7$=LNR$^3$R$^4$R$^5$, wherein L, R$^3$, and R$^4$ and R$^5$ are defined as above, and R$^6$ is H or lower alkyl.

18. The method of claim 17, wherein each of R$^1$ and R$^2$, in linkages of type (a), is methyl.

19. The method of claim 17, wherein at least one linkage is of type (b1), where each R is H, R$^4$ is H, CH$_3$, or an electron pair, and R$^3$ is selected from H, CH$_3$, C(=NH)NH$_2$, and C(O)-L-NHC(=NH)NH$_2$.

20. The method of claim 17, wherein at least one linkage is of type (b1), where each R is H, R$^4$ is an electron pair, and R$^3$ is selected from C(=NH)NH$_2$ and C(O)-L-NHC(=NH)NH$_2$.

21. The method of claim 19, wherein R$^3$ is C(O)-L-NHC(NH)NH$_2$, and L is a hydrocarbon having the structure —(CH$_2$)$_n$—, where n is 1 to 12.

22. The method of claim 17, wherein at least one linkage is of type (b1), where each R is H, and each of R$^3$ and R$^4$ is independently H or CH$_3$.

23. The method of claim 13, wherein the amino acid linker is AhxβAla, wherein Ahx is 6-amino hexanoic acid and βAla is β-alanine.

24. The method of claim 17, wherein at least one of the linkages is selected from cationic linkages (b1), (b2), and (b3).

* * * * *

```
                        SEQUENCE LISTING

<160> NUMBER OF SEQ ID NOS: 36

<210> SEQ ID NO 1
<211> LENGTH: 611
<212> TYPE: DNA
<213> ORGANISM: Homo sapiens

<400> SEQUENCE: 1
tccccactgt ccagcagagg gccaggcaca tgcccatgga ggggacctga gcagacccccc    60 atttcctttc caggtgtggc ctctggaacc tgactccgtt aggacgaaca tctgcccctt   120
cagggagggt gagccgaccg gcctgggget ggggttgggg tgttgcgagc gatgggtacc   180
tggcctgcgg tgactgtgcc ctttccttgc agaccccgc gcacaccaga acctctggca    240
agccgcccga ctgcaactgc tgaccctgca gagctggctg ctgacgcac cgtgctcgct    300 gcccgcagaa gcggcactgt gctggcgggc tccgggtggg gaccctgcc agccactggt    360 cccaccgctt tcctgggaga acgtcactgt ggacgtaagt gaagcagagg gcacctcccg   420
tggtgagggg agagtgggga accgggggtc ccctttttgtg atcccaccca ttcctctctt   480
tccacagaag gttctcgagt tcccattgct gaaaggccac cctaacctct gtgttcaggt   540
cagaaagggg tgcatagtgc tgggctggag gctggacctg ggcagacccc ccagccaagg   600
gggtcttagt t                                                        611

<210> SEQ ID NO 2
<211> LENGTH: 24
<212> TYPE: DNA
<213> ORGANISM: Artificial Sequence
<220> FEATURE:
<223> OTHER INFORMATION: Antisense targeting sequence for inducing exon
      skipping

<400> SEQUENCE: 2
caccctccct gaaggggcag atgt                                            24

<210> SEQ ID NO 3
<211> LENGTH: 24
<212> TYPE: DNA
<213> ORGANISM: Artificial Sequence
<220> FEATURE:
<223> OTHER INFORMATION: Antisense targeting sequence for inducing exon
      skipping

<400> SEQUENCE: 3
agaggttctg gtgtgcgcgg gggt                                            24

<210> SEQ ID NO 4
<211> LENGTH: 24
<212> TYPE: DNA
<213> ORGANISM: Artificial Sequence
<220> FEATURE:
<223> OTHER INFORMATION: Antisense targeting sequence for inducing exon
      skipping

<400> SEQUENCE: 4
```

```
tccccacccg gagcccgcca gcac                                              24

<210> SEQ ID NO 5
<211> LENGTH: 24
<212> TYPE: DNA
<213> ORGANISM: Artificial Sequence
<220> FEATURE:
<223> OTHER INFORMATION: Antisense targeting sequence for inducing exon
      skipping

<400> SEQUENCE: 5
gtccacagtg acgttctccc agga                                              24

<210> SEQ ID NO 6
<211> LENGTH: 24
<212> TYPE: DNA
<213> ORGANISM: Artificial Sequence
<220> FEATURE:
<223> OTHER INFORMATION: Antisense targeting sequence for inducing exon
      skipping

<400> SEQUENCE: 6
ctgcttcact tacgtccaca gtga                                              24

<210> SEQ ID NO 7
<211> LENGTH: 24
<212> TYPE: DNA
<213> ORGANISM: Artificial Sequence
<220> FEATURE:
<223> OTHER INFORMATION: Antisense targeting sequence for inducing exon
      skipping

<400> SEQUENCE: 7
actcgagaac cttctgtgga aaga                                              24

<210> SEQ ID NO 8
<211> LENGTH: 24
<212> TYPE: DNA
<213> ORGANISM: Artificial Sequence
<220> FEATURE:
<223> OTHER INFORMATION: Antisense targeting sequence for inducing exon
      skipping

<400> SEQUENCE: 8
ctgaacacag aggttagggt ggcc                                              24

<210> SEQ ID NO 9
<211> LENGTH: 24
<212> TYPE: DNA
<213> ORGANISM: Artificial Sequence
<220> FEATURE:
<223> OTHER INFORMATION: Antisense targeting sequence for inducing exon
      skipping

<400> SEQUENCE: 9
atgcacccct ttctgacctg aaca                                              24

<210> SEQ ID NO 10
<211> LENGTH: 24
<212> TYPE: DNA
<213> ORGANISM: Artificial Sequence
<220> FEATURE:
<223> OTHER INFORMATION: Antisense targeting sequence for inducing exon
      skipping

<400> SEQUENCE: 10
ccagcccagc actatgcacc cctt                                              24
```

```
<210> SEQ ID NO 11
<211> LENGTH: 17
<212> TYPE: DNA
<213> ORGANISM: Artificial Sequence
<220> FEATURE:
<223> OTHER INFORMATION: Antisense targeting sequence for inducing exon
      skipping

<400> SEQUENCE: 11
ctgaacacag aggttag                                                      17

<210> SEQ ID NO 12
<211> LENGTH: 17
<212> TYPE: DNA
<213> ORGANISM: Artificial Sequence
<220> FEATURE:
<223> OTHER INFORMATION: Antisense targeting sequence for inducing exon
      skipping

<400> SEQUENCE: 12
ctggacacag aggttgg                                                      17

<210> SEQ ID NO 13
<211> LENGTH: 22
<212> TYPE: DNA
<213> ORGANISM: Artificial Sequence
<220> FEATURE:
<223> OTHER INFORMATION: Antisense targeting sequence for inducing exon
      skipping

<400> SEQUENCE: 13
tctgacctga acacagaggt ta                                                22

<210> SEQ ID NO 14
<211> LENGTH: 22
<212> TYPE: DNA
<213> ORGANISM: Artificial Sequence
<220> FEATURE:
<223> OTHER INFORMATION: Antisense targeting sequence for inducing exon
      skipping

<400> SEQUENCE: 14
tctgacctgg acacagaggt tg                                                22

<210> SEQ ID NO 15
<211> LENGTH: 10
<212> TYPE: PRT
<213> ORGANISM: Artificial Sequence
<220> FEATURE:
<223> OTHER INFORMATION: Cell penetrating peptide

<400> SEQUENCE: 15

Arg Arg Arg Gln Arg Arg Lys Lys Arg Cys
 1               5                  10

<210> SEQ ID NO 16
<211> LENGTH: 12
<212> TYPE: PRT
<213> ORGANISM: Artificial Sequence
<220> FEATURE:
<223> OTHER INFORMATION: Cell penetrating peptide

<400> SEQUENCE: 16

Arg Arg Arg Arg Arg Arg Arg Arg Arg Phe Phe Cys
 1               5                  10
```

```
<210> SEQ ID NO 17
<211> LENGTH: 13
<212> TYPE: PRT
<213> ORGANISM: Artificial Sequence
<220> FEATURE:
<223> OTHER INFORMATION: Cell penetrating peptide
<220> FEATURE:
<221> NAME/KEY: MOD_RES
<222> LOCATION: 3, 6, 9, 12
<223> OTHER INFORMATION: Acp
<220> FEATURE:
<221> NAME/KEY: MOD_RES
<222> LOCATION: 13
<223> OTHER INFORMATION: bAla

<400> SEQUENCE: 17

Arg Arg Xaa Arg Arg Xaa Arg Arg Xaa Arg Arg Xaa Xaa
 1               5                  10

<210> SEQ ID NO 18
<211> LENGTH: 14
<212> TYPE: PRT
<213> ORGANISM: Artificial Sequence
<220> FEATURE:
<223> OTHER INFORMATION: Cell penetrating peptide
<220> FEATURE:
<221> NAME/KEY: MOD_RES
<222> LOCATION: 2, 5, 8, 11, 13
<223> OTHER INFORMATION: Acp
<220> FEATURE:
<221> NAME/KEY: MOD_RES
<222> LOCATION: 14
<223> OTHER INFORMATION: bAla

<400> SEQUENCE: 18

Arg Xaa Arg Arg Xaa Arg Arg Xaa Arg Arg Xaa Arg Xaa Xaa
 1               5                  10

<210> SEQ ID NO 19
<211> LENGTH: 14
<212> TYPE: PRT
<213> ORGANISM: Artificial Sequence
<220> FEATURE:
<223> OTHER INFORMATION: Cell penetrating peptide
<220> FEATURE:
<221> NAME/KEY: MOD_RES
<222> LOCATION: 1, 4, 7, 10, 13
<223> OTHER INFORMATION: Acp
<220> FEATURE:
<221> NAME/KEY: MOD_RES
<222> LOCATION: 14
<223> OTHER INFORMATION: bAla

<400> SEQUENCE: 19

Xaa Arg Arg Xaa Arg Arg Xaa Arg Arg Xaa Arg Arg Xaa Xaa
 1               5                  10

<210> SEQ ID NO 20
<211> LENGTH: 13
<212> TYPE: PRT
<213> ORGANISM: Artificial Sequence
<220> FEATURE:
<223> OTHER INFORMATION: Cell penetrating peptide
<220> FEATURE:
<221> NAME/KEY: MOD_RES
<222> LOCATION: 2, 4, 6, 8, 10, 12
<223> OTHER INFORMATION: Acp
<220> FEATURE:
<221> NAME/KEY: MOD_RES
<222> LOCATION: 13
<223> OTHER INFORMATION: bAla
```

```
<400> SEQUENCE: 20

Arg Xaa Arg Xaa Arg Xaa Arg Xaa Arg Xaa Arg Xaa Xaa
 1               5                  10

<210> SEQ ID NO 21
<211> LENGTH: 15
<212> TYPE: PRT
<213> ORGANISM: Artificial Sequence
<220> FEATURE:
<223> OTHER INFORMATION: Cell penetrating peptide
<220> FEATURE:
<221> NAME/KEY: MOD_RES
<222> LOCATION: 2, 4, 6, 8, 10, 12, 14
<223> OTHER INFORMATION: Acp
<220> FEATURE:
<221> NAME/KEY: MOD_RES
<222> LOCATION: 15
<223> OTHER INFORMATION: bAla

<400> SEQUENCE: 21

Arg Xaa Arg Xaa Arg Xaa Arg Xaa Arg Xaa Arg Xaa Arg Xaa Xaa
 1               5                  10                  15

<210> SEQ ID NO 22
<211> LENGTH: 17
<212> TYPE: PRT
<213> ORGANISM: Artificial Sequence
<220> FEATURE:
<223> OTHER INFORMATION: Cell penetrating peptide
<220> FEATURE:
<221> NAME/KEY: MOD_RES
<222> LOCATION: 2, 5, 8, 11, 14, 16
<223> OTHER INFORMATION: Acp
<220> FEATURE:
<221> NAME/KEY: MOD_RES
<222> LOCATION: 17
<223> OTHER INFORMATION: bAla

<400> SEQUENCE: 22

Arg Xaa Arg Arg Xaa Arg Arg Xaa Arg Arg Xaa Arg Arg Xaa Arg Xaa
 1               5                  10                  15

Xaa

<210> SEQ ID NO 23
<211> LENGTH: 14
<212> TYPE: PRT
<213> ORGANISM: Artificial Sequence
<220> FEATURE:
<223> OTHER INFORMATION: Cell penetrating peptide
<220> FEATURE:
<221> NAME/KEY: MOD_RES
<222> LOCATION: 2, 8, 13
<223> OTHER INFORMATION: Acp
<220> FEATURE:
<221> NAME/KEY: MOD_RES
<222> LOCATION: 5, 11, 14
<223> OTHER INFORMATION: bAla

<400> SEQUENCE: 23

Arg Xaa Arg Arg Xaa Arg Arg Xaa Arg Arg Xaa Arg Xaa Xaa
 1               5                  10

<210> SEQ ID NO 24
<211> LENGTH: 7
<212> TYPE: PRT
<213> ORGANISM: Artificial Sequence
<220> FEATURE:
<223> OTHER INFORMATION: Cell penetrating peptide

<400> SEQUENCE: 24
```

```
Arg Arg Arg Arg Arg Arg Gly
1               5

<210> SEQ ID NO 25
<211> LENGTH: 8
<212> TYPE: PRT
<213> ORGANISM: Artificial Sequence
<220> FEATURE:
<223> OTHER INFORMATION: Cell penetrating peptide

<400> SEQUENCE: 25

Arg Arg Arg Arg Arg Arg Arg Gly
1               5

<210> SEQ ID NO 26
<211> LENGTH: 9
<212> TYPE: PRT
<213> ORGANISM: Artificial Sequence
<220> FEATURE:
<223> OTHER INFORMATION: Cell penetrating peptide

<400> SEQUENCE: 26

Arg Arg Arg Arg Arg Arg Arg Arg Gly
1               5

<210> SEQ ID NO 27
<211> LENGTH: 11
<212> TYPE: PRT
<213> ORGANISM: Artificial Sequence
<220> FEATURE:
<223> OTHER INFORMATION: Cell penetrating peptide

<400> SEQUENCE: 27

Arg Arg Arg Arg Arg Gly Arg Arg Arg Arg Gly
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Cell penetrating peptide

<400> SEQUENCE: 28

Arg Arg Arg Arg Arg Phe Phe Arg Arg Arg Arg Gly
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Cell penetrating peptide

<400> SEQUENCE: 29

Arg Lys Lys Arg Arg Gln Arg Arg Arg Gly
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Cell penetrating peptide

<400> SEQUENCE: 30
```

Arg Arg Arg Gln Arg Arg Lys Lys Arg Gly
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Cell penetrating peptide
<220> FEATURE:
<221> NAME/KEY: MOD_RES
<222> LOCATION: 2, 8
<223> OTHER INFORMATION: Acp

<400> SEQUENCE: 31

Arg Xaa Arg Arg Gly Gly Arg Xaa Arg Arg Gly Gly
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Cell penetrating peptide
<220> FEATURE:
<221> NAME/KEY: MOD_RES
<222> LOCATION: 2, 6, 8, 12
<223> OTHER INFORMATION: Acp

<400> SEQUENCE: 32

Arg Xaa Arg Arg Arg Xaa Arg Xaa Arg Arg Arg Xaa Gly
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Cell penetrating peptide
<220> FEATURE:
<221> NAME/KEY: VARIANT
<222> LOCATION: 1, 3, 4, 7, 9, 10
<223> OTHER INFORMATION: Xaa = Lysine, Arginine or Arginine analog
<220> FEATURE:
<221> NAME/KEY: VARIANT
<222> LOCATION: 2, 8
<223> OTHER INFORMATION: Xaa = a neutral amino acid, -C(O)-(CHR)n-NH-,
      where n is 2 to 7 and R is H or methyl
<220> FEATURE:
<221> NAME/KEY: VARIANT
<222> LOCATION: 5, 6, 11, 12
<223> OTHER INFORMATION: Xaa = alpha-amino acid having a neutral aralkyl
      side chain

<400> SEQUENCE: 33

Xaa Xaa Xaa Xaa Xaa Xaa Xaa Xaa Xaa Xaa Xaa Xaa
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Cell penetrating peptide
<220> FEATURE:
<221> NAME/KEY: VARIANT
<222> LOCATION: 2, 6, 8, 12
<223> OTHER INFORMATION: Xaa = Gly or Acp

<400> SEQUENCE: 34

Arg Xaa Arg Arg Arg Xaa Arg Xaa Arg Arg Arg Xaa

```
<210> SEQ ID NO 35
<211> LENGTH: 9
<212> TYPE: PRT
<213> ORGANISM: Artificial Sequence
<220> FEATURE:
<223> OTHER INFORMATION: Cell penetrating peptide
<220> FEATURE:
<221> NAME/KEY: VARIANT
<222> LOCATION: 3, 5, 9
<223> OTHER INFORMATION: Xaa = Gly or Acp

<400> SEQUENCE: 35

Arg Arg Xaa Arg Xaa Arg Arg Arg Xaa
 1               5

<210> SEQ ID NO 36
<211> LENGTH: 4
<212> TYPE: PRT
<213> ORGANISM: Artificial Sequence
<220> FEATURE:
<223> OTHER INFORMATION: Synthetic peptide loop insert

<400> SEQUENCE: 36

Cys Gly Pro Cys
 1
```